United States Patent
Li

(10) Patent No.: US 9,556,447 B2
(45) Date of Patent: Jan. 31, 2017

(54) SOYBEAN HRP1 PROMOTER AND ITS USE IN TISSUE-SPECIFIC EXPRESSION OF TRANSGENIC GENES IN PLANTS

(71) Applicant: E.I. DU PONT DE NEMOURS AND COMPANY, Wilmington, DE (US)

(72) Inventor: Zhongsen Li, Hockessin, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 14/772,711

(22) PCT Filed: Mar. 12, 2014

(86) PCT No.: PCT/US2014/023848
§ 371 (c)(1),
(2) Date: Sep. 3, 2015

(87) PCT Pub. No.: WO2014/159477
PCT Pub. Date: Oct. 2, 2014

(65) Prior Publication Data
US 2015/0376631 A1    Dec. 31, 2015

Related U.S. Application Data

(60) Provisional application No. 61/781,036, filed on Mar. 14, 2013.

(51) Int. Cl.
*C12N 15/82*    (2006.01)

(52) U.S. Cl.
CPC ......... *C12N 15/823* (2013.01); *C12N 15/8234* (2013.01)

(58) Field of Classification Search
None
See application file for complete search history.

(56) References Cited

FOREIGN PATENT DOCUMENTS

WO    02/00904 A2    1/2002

OTHER PUBLICATIONS

Schmutz J. et al. Genome sequence of the palaaeopolyploid soybean. (2010) Nature; vol. 463; pp. 178-183.*
Hirokazu Hakozaki et al., Cloning and expression pattern of a novel microspore-specific gene encoding hypersensitive-induced response protein (LjHIR1) from the model legume, Lotus japonicus, Genes Genet Syst, 2004, pp. 307-310, vol. 79.
Qing-Hu Ma et al., Expression if Isopentenyl Transferase Gene Controlled by Seed-Specific Lectin Promoter in Transgenic Tobacco Influences Seed Development, J Plant Growth Regul, 2008, pp. 68-76, vol. 27.
H.-J. Quandt et al., Tissue-specific activity and light-dependent regulation of a soybean rbcS Promoter in transgenic tobacco plants monitored with the firefly luciferase gene, Plant Science, 1992, pp. 59-70, vol. 82.
Jeremy Schmutz et al., Genome sequence of the palaeopolyploid soybean, Nature, Jan. 14, 2010, pp. 178-183, vol. 463.
Database Accession No. FK437137, Jul. 2, 2008, XP-002727886.
Database Accession No. ED713268, Nov. 3, 2006, XP-002727887.
Database Accession No. Glyma02g02550, XP-002727888.
National Center for Biotechnology Information—Accession XM_003519030.1, Jan. 7, 2014.
International Search Report—PCT/US2014/023848—mailed Aug. 19, 2014.

* cited by examiner

*Primary Examiner* — Cathy Kingdon Worley

(57) ABSTRACT

The invention relates to gene expression regulatory sequences from soybean, specifically to the promoter of a soybean hypersensitive-induced response protein gene and fragments thereof and their use in promoting the expression of one or more heterologous nucleic acid fragments in a tissue-specific manner in plants. The invention further discloses compositions, polynucleotide constructs, transformed host cells, transgenic plants and seeds containing the recombinant construct with the promoter, and methods for preparing and using the same.

22 Claims, 10 Drawing Sheets

FIG. 8

Figure 1:
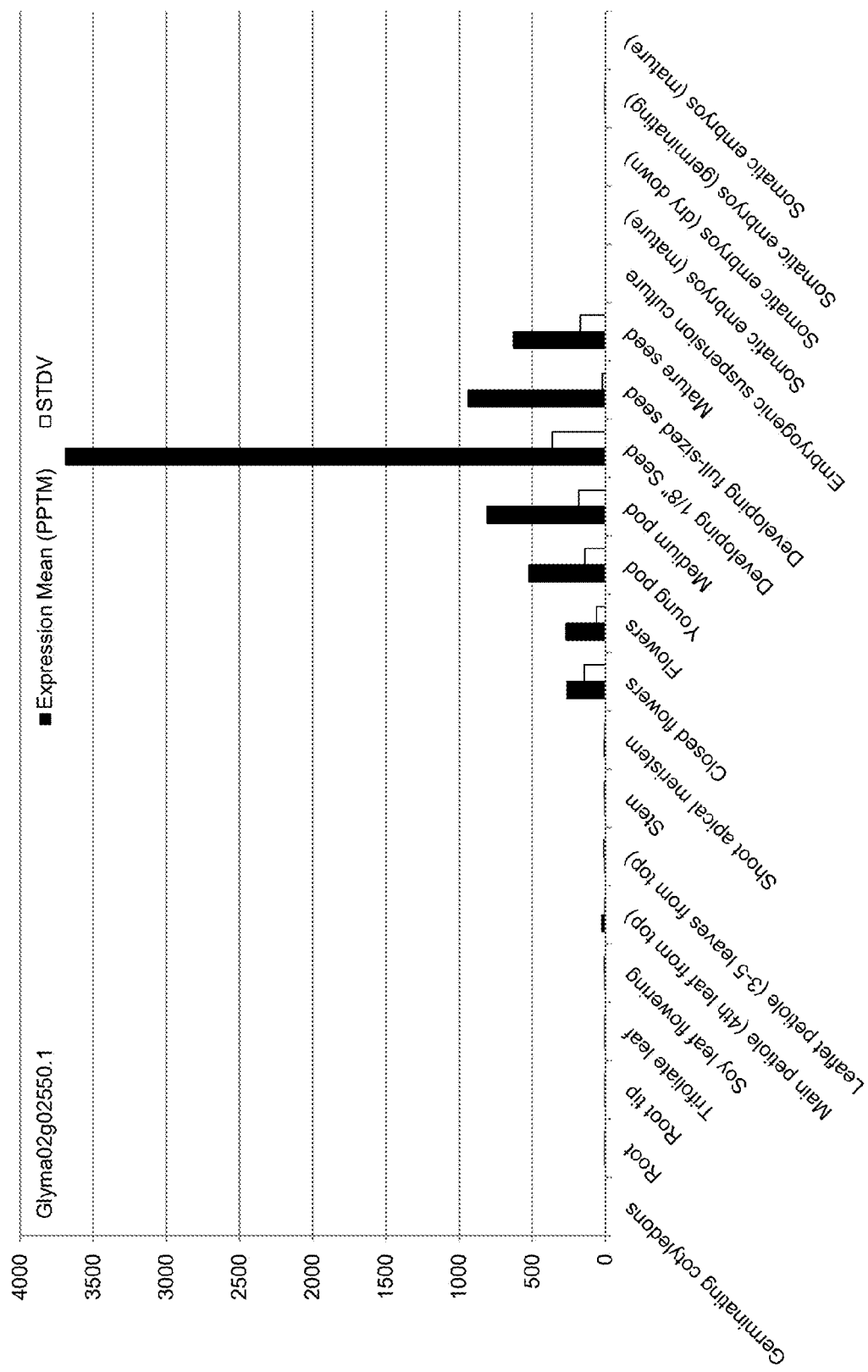

SOYBEAN HRP1 PROMOTER AND ITS USE IN TISSUE-SPECIFIC EXPRESSION OF TRANSGENIC GENES IN PLANTS

This application claims the benefit of U.S. Application No. 61/781,036, filed Mar. 14, 2013, the entire content of which is hereby incorporated by reference.

FIELD OF THE INVENTION

This invention relates to a plant promoter GM-HRP1 and fragments thereof and their use in altering expression of at least one heterologous nucleotide sequence in plants in a tissue-specific manner.

BACKGROUND OF THE INVENTION

Recent advances in plant genetic engineering have opened new doors to engineer plants to have improved characteristics or traits, such as plant disease resistance, insect resistance, herbicidal resistance, yield improvement, improvement of the nutritional quality of the edible portions of the plant, and enhanced stability or shelf-life of the ultimate consumer product obtained from the plants. Thus, a desired gene (or genes) with the molecular function to impart different or improved characteristics or qualities can be incorporated properly into the plant's genome. The newly integrated gene (or genes) coding sequence can then be expressed in the plant cell to exhibit the desired new trait or characteristic. It is important that appropriate regulatory signals be present in proper configurations in order to obtain the expression of the newly inserted gene coding sequence in the plant cell. These regulatory signals typically include a promoter region, a 5' non-translated leader sequence and a 3' transcription termination/polyadenylation sequence.

A promoter is a non-coding genomic DNA sequence, usually upstream (5') to the relevant coding sequence, to which RNA polymerase binds before initiating transcription. This binding aligns the RNA polymerase so that transcription will initiate at a specific transcription initiation site. The nucleotide sequence of the promoter determines the nature of the RNA polymerase binding and other related protein factors that attach to the RNA polymerase and/or promoter, and the rate of RNA synthesis.

It has been shown that certain promoters are able to direct RNA synthesis at a higher rate than others. These are called "strong promoters". Certain other promoters have been shown to direct RNA synthesis at higher levels only in particular types of cells or tissues and are often referred to as "tissue specific promoters", or "tissue-preferred promoters", if the promoters direct RNA synthesis preferentially in certain tissues (RNA synthesis may occur in other tissues at reduced levels). Since patterns of expression of a chimeric gene (or genes) introduced into a plant are controlled using promoters, there is an ongoing interest in the isolation of novel promoters that are capable of controlling the expression of a chimeric gene (or genes) at certain levels in specific tissue types or at specific plant developmental stages.

Although advances in technology provide greater success in transforming plants with chimeric genes, there is still a need for specific expression of such genes in desired plants. Often times it is desired to selectively express target genes in a specific tissue because of toxicity or efficacy concerns. For example, embryo tissue is a type of tissue where specific expression is desirable and there remains a need for promoters that preferably initiate transcription in embryo tissue. Promoters that initiate transcription preferably in embryo tissue control genes involved in embryo and seed development.

SUMMARY OF THE INVENTION

This invention concerns a recombinant DNA construct comprising an isolated polynucleotide comprising a promoter wherein said promoter comprises the nucleotide sequence set forth in SEQ ID NOs: 1, 2, 3, 4, 5, 6, 7, 8, 9 or 45 or said promoter comprises a functional fragment of the nucleotide sequence set forth in SEQ ID NOs: 1, 2, 3, 4, 5, 6, 7, 8, 9 or 45, or wherein said promoter comprises a nucleotide sequence having at least 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% sequence identity, based on the Clustal V method of alignment with pairwise alignment default parameters (KTUPLE=2, GAP PENALTY=5, WINDOW=4 and DIAGONALS SAVED=4), when compared to the nucleotide sequence of SEQ ID NOs: 1, 2, 3, 4, 5, 6, 7, 8, 9 or 45 operably linked to at least one heterologous sequence.

In a second embodiment, the invention concerns a recombinant DNA construct comprising an isolated polynucleotide comprising a promoter region of the plasma membrane intrinsic protein (HRP1) *Glycine max* gene as set forth in SEQ ID NO:1, wherein said promoter comprises a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 11511, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, or 1208 consecutive nucleotides, wherein the first nucleotide deleted is the cytosine nucleotide ['C'] at position 1 of SEQ ID NO:1, operably linked to at least one heterologous sequence. This invention also concerns a recombinant DNA construct of the embodiments disclosed herein, wherein the promoter is a tissue-specific promoter.

In a third embodiment, this invention concerns a recombinant DNA construct comprising at least one heterologous nucleotide sequence operably linked to the promoter of the disclosure.

In a fourth embodiment, this invention concerns a cell, plant, or seed comprising a recombinant DNA construct of the present disclosure.

In a fifth embodiment, this invention concerns plants comprising this recombinant DNA construct and seeds obtained from such plants.

In a sixth embodiment, this invention concerns a method of altering (increasing or decreasing) expression of at least one heterologous nucleic acid fragment in a plant cell which comprises:
  (a) transforming a plant cell with the recombinant expression construct described herein;
  (b) growing fertile mature plants from the transformed plant cell of step (a);
  (c) selecting plants containing the transformed plant cell wherein the expression of the heterologous nucleic acid fragment is increased or decreased.

In a seventh embodiment, this invention concerns a method for expressing a yellow fluorescent protein ZS-GREEN1 (GFP) in a host cell comprising:
  (a) transforming a host cell with a recombinant expression construct comprising at least one ZS-GREEN1 nucleic acid fragment operably linked to a promoter wherein said promoter consists essentially of the nucleotide sequence set forth in SEQ ID NOs:1, 2, 3, 4, 5, 6, 7, 8, 9 or 45; and
  (b) growing the transformed host cell under conditions that are suitable for expression of the recombinant DNA construct, wherein expression of the recombinant DNA construct results in production of increased levels of ZS-GREEN1 protein in the transformed host cell when compared to a corresponding nontransformed host cell.

In an eighth embodiment, this invention concerns a recombinant DNA construct comprising an isolated nucleic acid fragment comprising a plant hypersensitive-induced response protein (HRP1) gene promoter.

In a ninth embodiment, this invention concerns a method of altering a marketable plant trait. The marketable plant trait concerns genes and proteins involved in disease resistance, herbicide resistance, insect resistance, carbohydrate metabolism, fatty acid metabolism, amino acid metabolism, plant development, plant growth regulation, yield improvement, drought resistance, cold resistance, heat resistance, and salt resistance.

In a tenth embodiment, this invention concerns a recombinant DNA construct comprising an isolated polynucleotide linked to a heterologous nucleotide sequence. The heterologous nucleotide sequence encodes a protein involved in disease resistance, herbicide resistance, insect resistance; carbohydrate metabolism, fatty acid metabolism, amino acid metabolism, plant development, plant growth regulation, yield improvement, drought resistance, cold resistance, heat resistance, or salt resistance in plants.

BRIEF DESCRIPTION OF THE DRAWINGS AND SEQUENCE LISTINGS

The invention can be more fully understood from the following detailed description and the accompanying drawings and Sequence Listing that form a part of this application.

FIG. 1 is the relative expression of a soybean hypersensitive-induced response protein (HRP1) gene (PSO401672, Glyma02g02550.1) in twenty-one soybean tissues by Illumina (Solexa) digital gene expression dual-tag-based mRNA profiling. The gene expression profile indicates that the HRP1 gene is expressed specifically in flowers, pods, and seeds.

Figure 2:
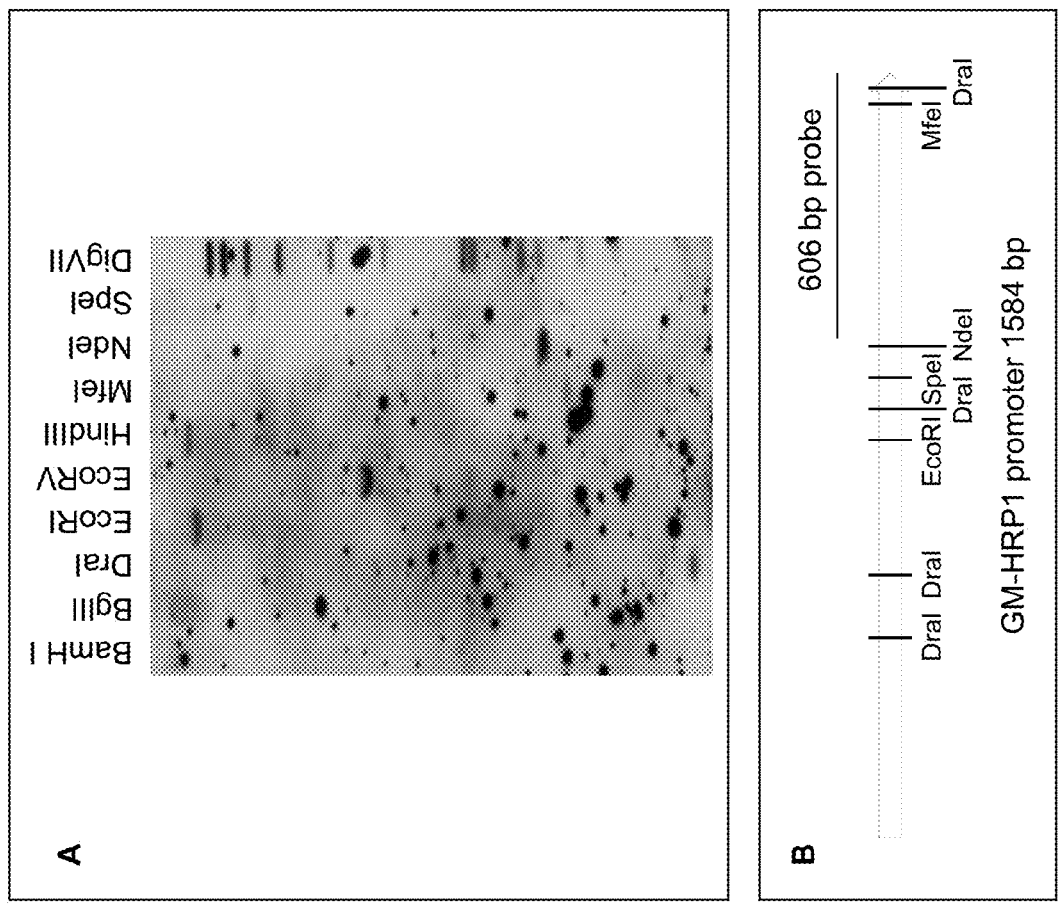

FIG. 2 (A) is HRP1 promoter copy number analysis by Southern. FIG. 2A is the image of a Southern blot hybridized with a 606 bp HRP1 promoter probe made with primers QC641-S5 and PSO382305Nco by PCR. FIG. 2B shows restriction enzyme recognitions sites in the HRP1 probe region.

Figure 3A:
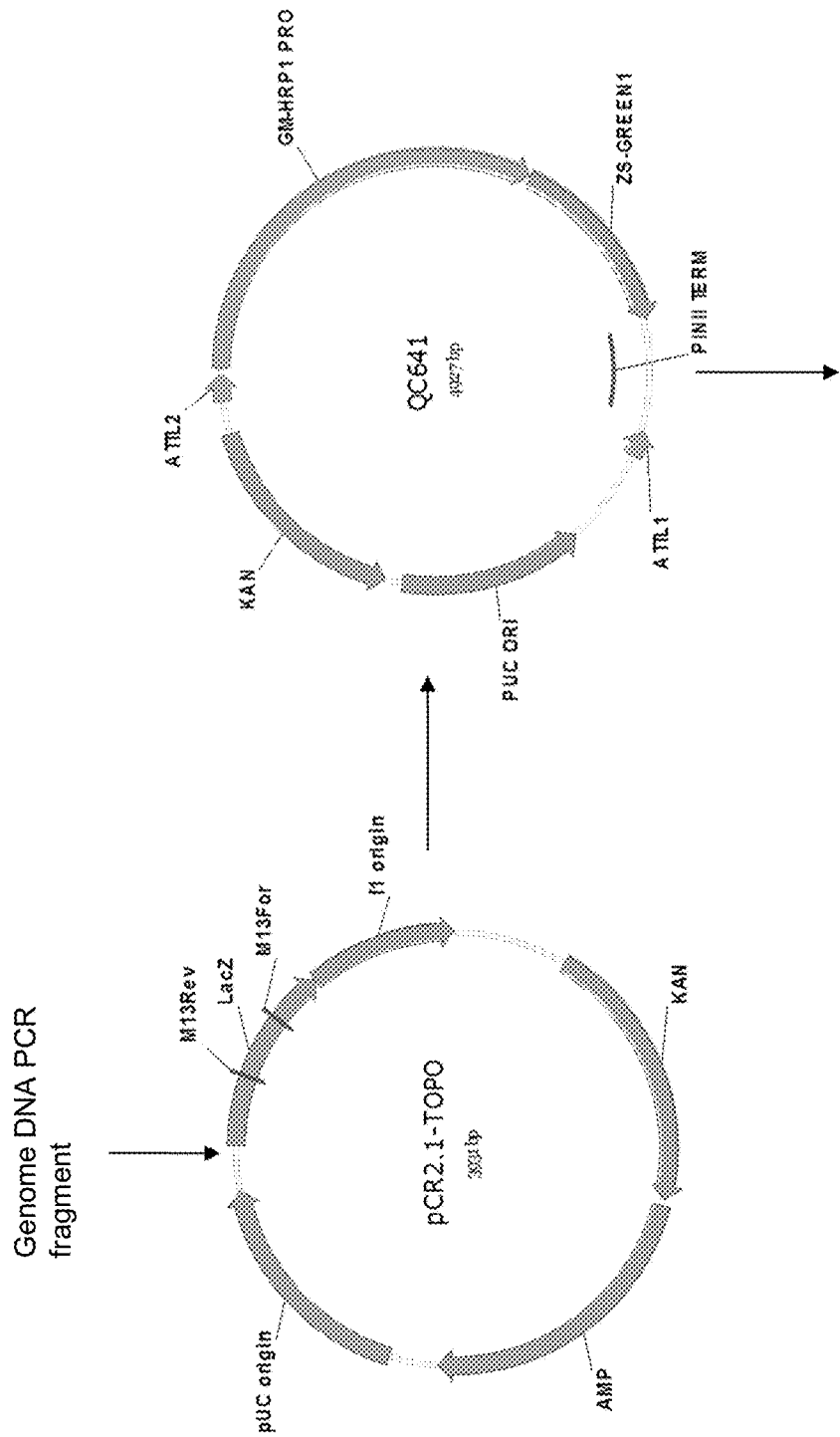
Figure 3B:
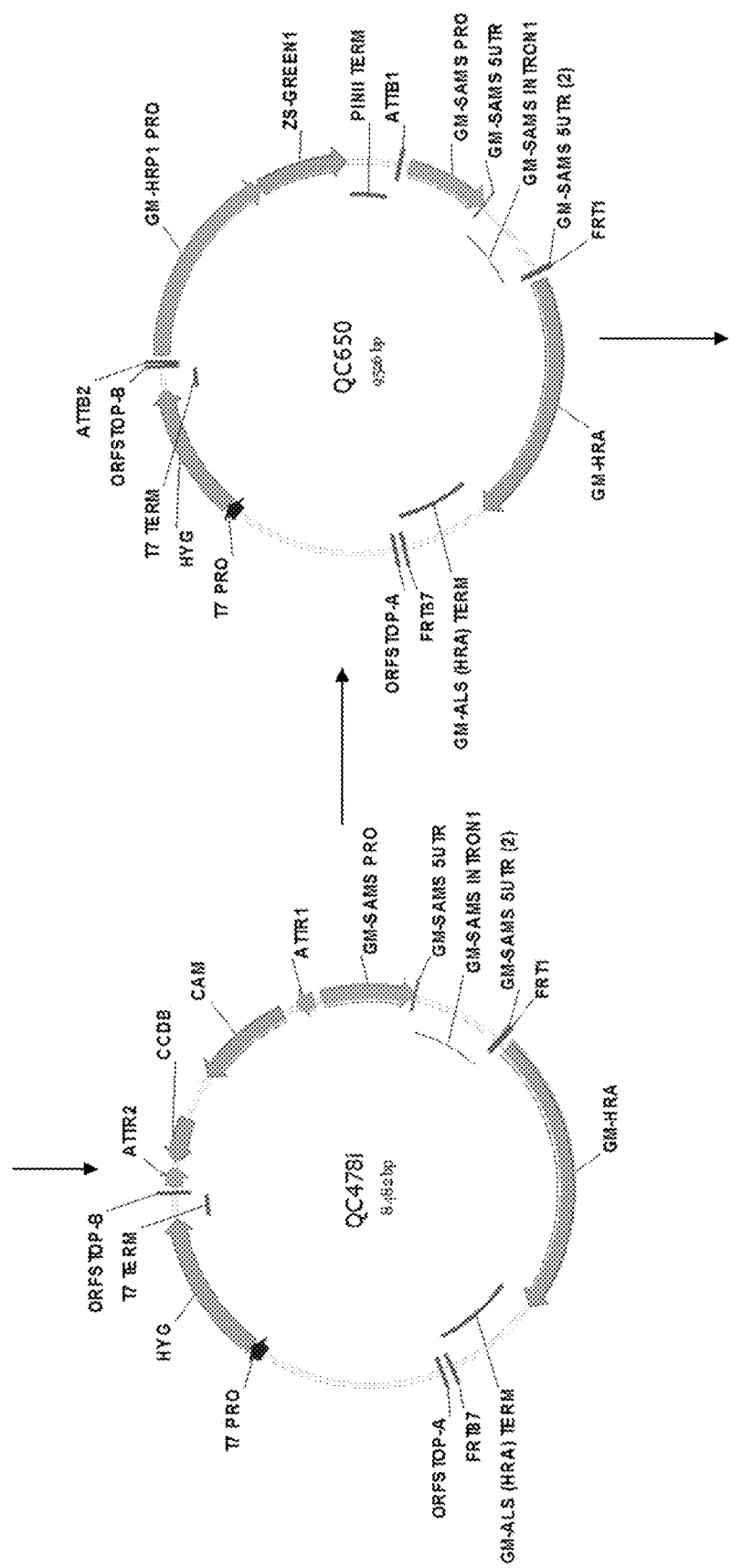

FIG. 3A-3B shows the maps of plasmids pCR2.1-TOPO, QC641, QC478i, and QC650. The 7012 bp AscI-AscI fragment of QC650 is used to produce transgenic soybean plants.

Figure 4A:
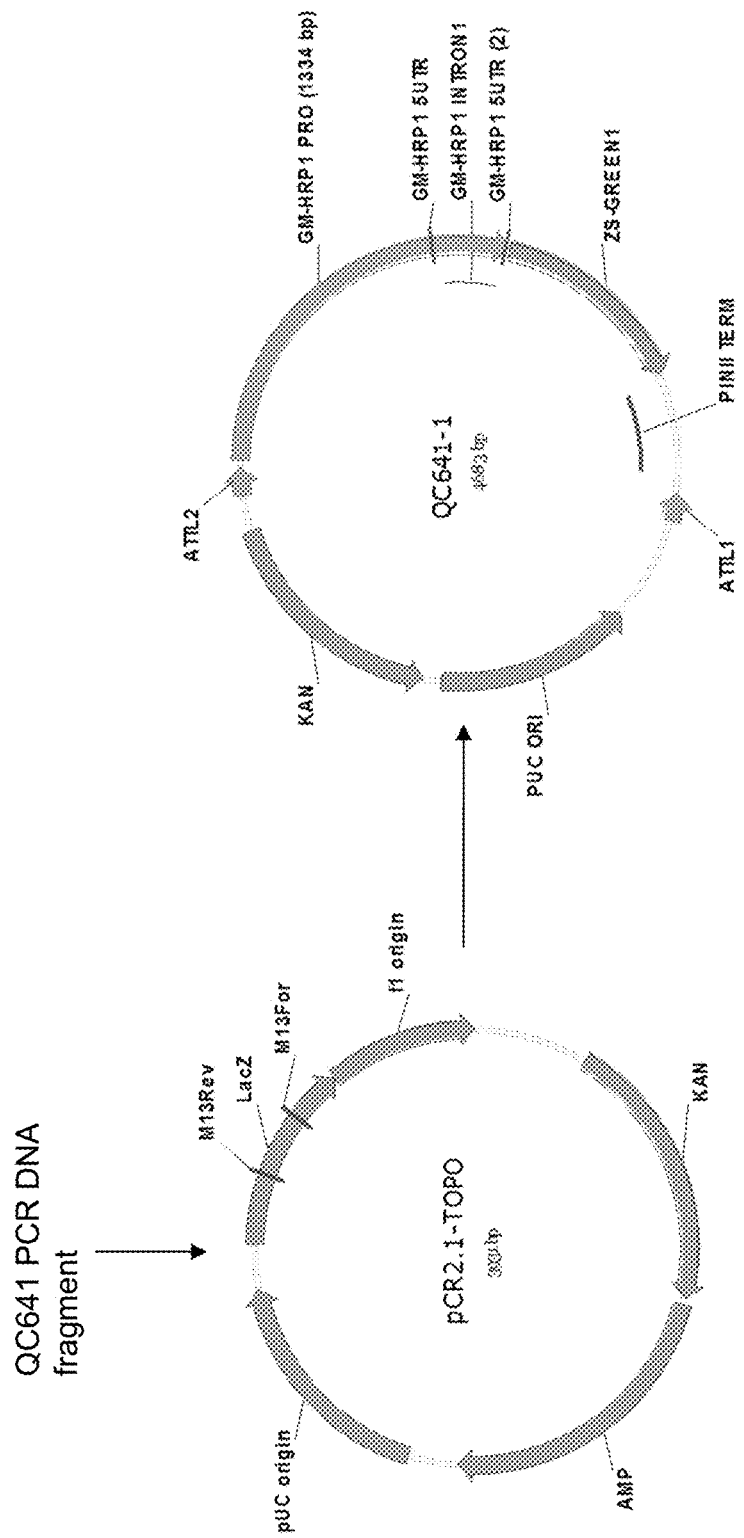
Figure 4B:
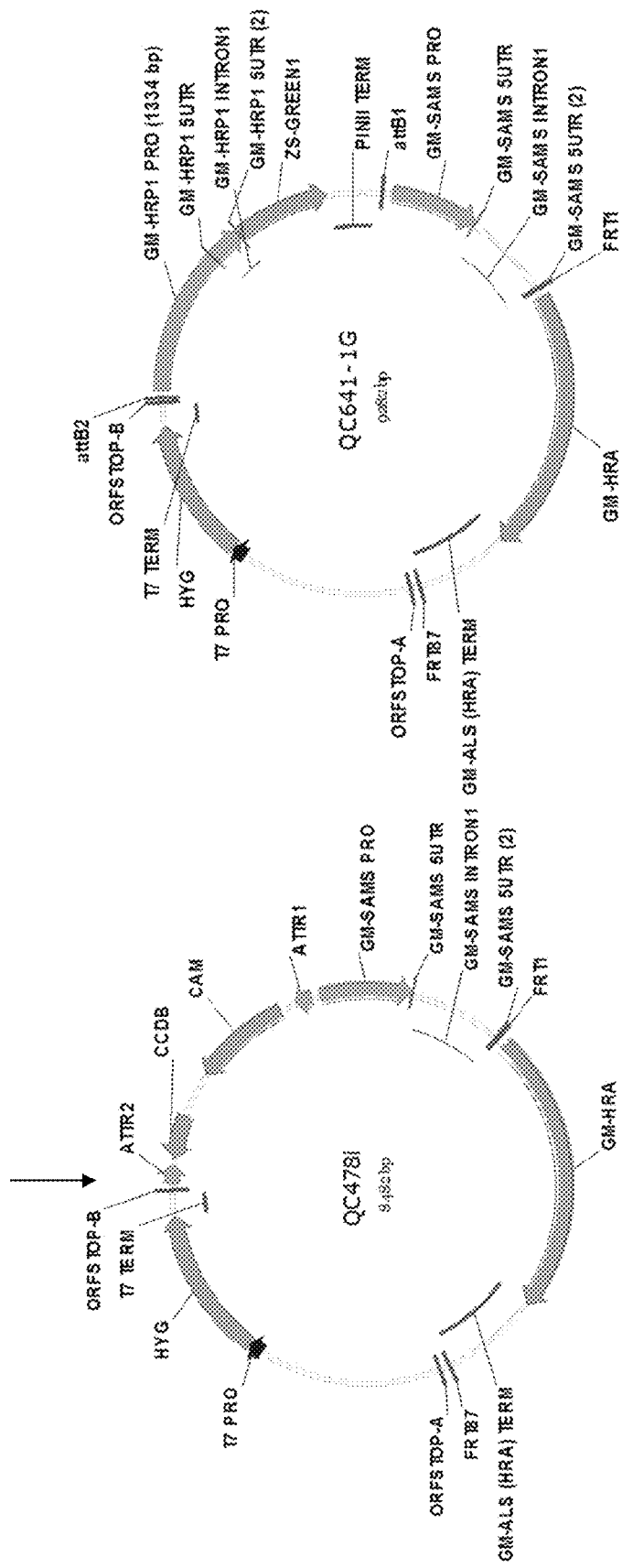

FIG. 4A-4B shows the maps of plasmids pCR2.1-TOPO, QC641-1, QC478i, and QC641-1G containing a truncated 1334 bp HRP1 promoter. Other promoter deletion constructs QC641-2G, QC641-3G, QC641-4G, QC641-5G, QC641-6G, QC641-7G, and QC641-8G containing the 1149, 930, 721, 606, 487, 376, and 1359 bp truncated HRP1 promoters, respectively, have the same map configuration, except for the truncated promoter sequences. The 1359 bp HRP1 promoter in QC641-8G has a 220 bp intron in the 5' UTR region removed.

Figure 5:
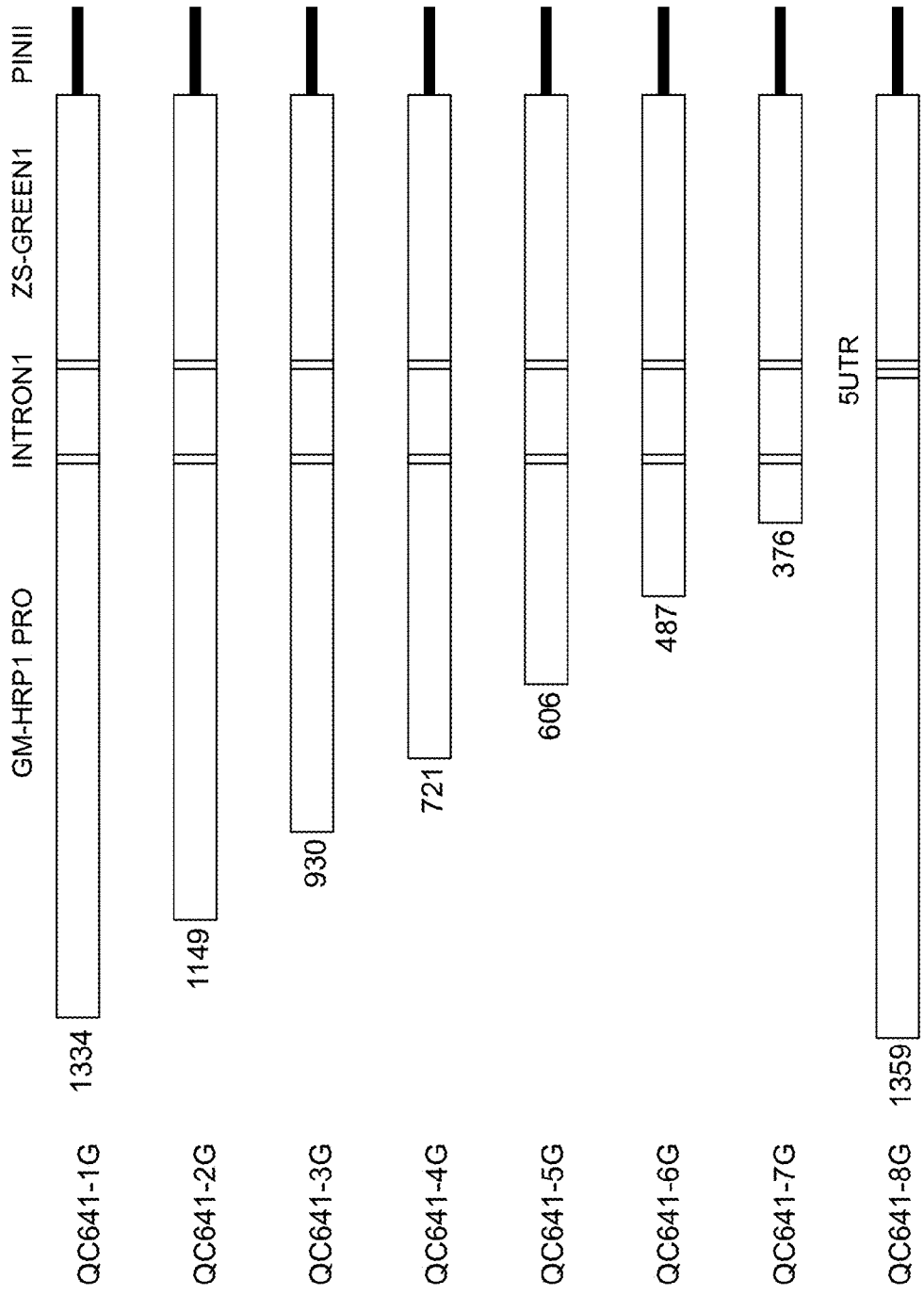

FIG. 5 is the schematic descriptions of the progressive truncations of the HRP1 promoter in constructs QC641-1G, QC641-2G, QC641-3G, QC641-4G, QC641-5G, QC641-6G, QC641-7G, and QC641-8G. The size of each promoter truncation including the 3' end NcoI cloning site is given at the left end of each drawing.

Figure 6:
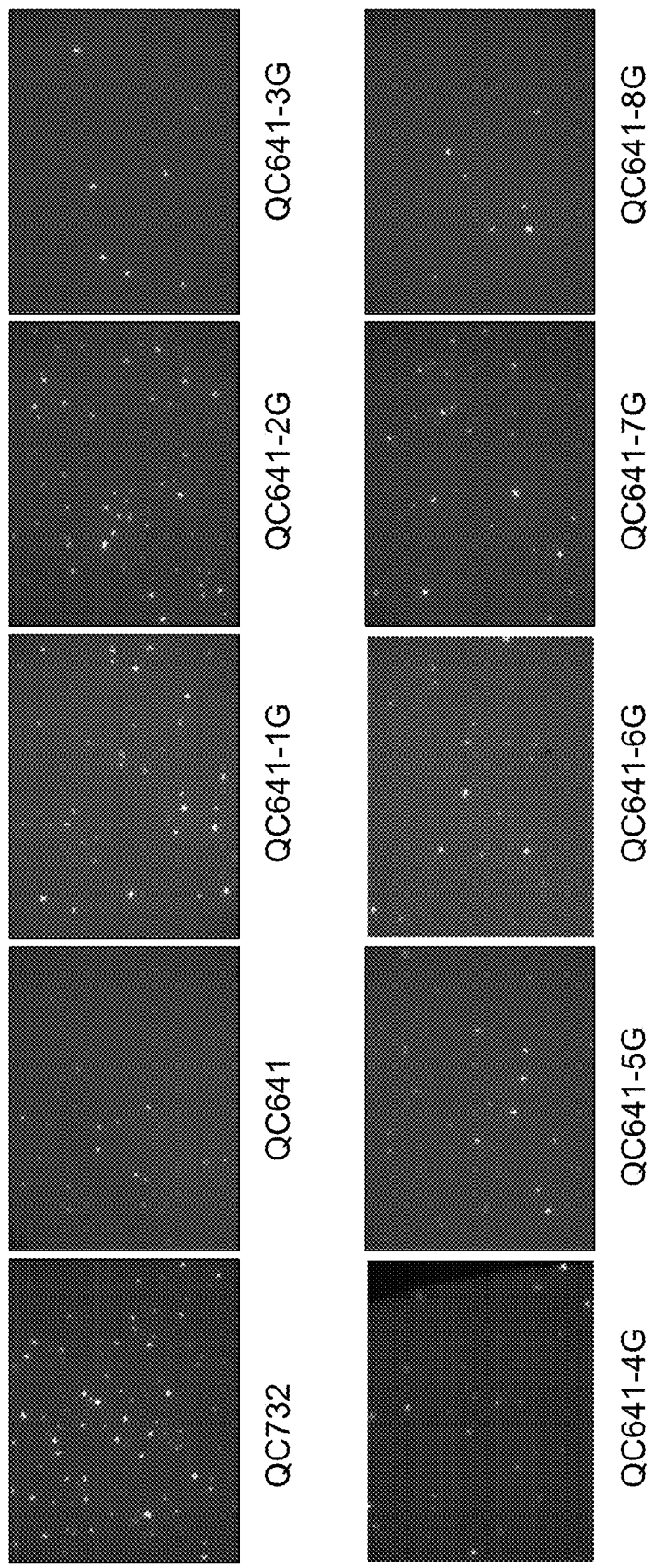

FIG. 6 is the transient expression of the fluorescent protein reporter gene ZS-GREEN1 in the cotyledons of germinating soybean seeds. The reporter gene is driven by the full length HRP1 promoter in QC641 or by progressively truncated HRP1 promoters in the transient expression constructs QC641-1G, QC641-2G, QC641-3G, QC641-4G, QC641-5G, QC641-6G, QC641-7G, and QC641-8G. DNA construct QC732 used as a positive control has a strong constitutive promoter GM-EF1A driving ZS-GREEN1 gene (U.S. Patent Application No. 20080313776).

FIG. 7A-7P shows the stable expression of the fluorescent protein reporter gene ZS-GREEN1 in different tissues of transgenic soybean plants containing a single copy of HRP1: GFP DNA of construct QC650, comprising the 1584 bp HRP1 promoter of SEQ ID NO:1. A: Embryonic callus, B: Developing somatic embryos, C: Flower bud, longitudinal section showing anthers and ovules, D: Pistil, longitudinal section showing fluorescent signals inside the ovules, E: Opening flower, longitudinal section showing ovules with fluorescent signals inside, F: Pistil, longitudinal section showing strong fluorescent signals inside the ovules, G: Open flower, longitudinal section showing anthers and ovules, H: Pistil, longitudinal section showing ovules of an open flower, fluorescent signals are concentrated at the micropylar end, I: Stamen and pistil from flower bud or open flower, J: Stemen from flower bud showing strong fluorescent signals in anthers, K: Very young pod, longitudinal section showing developing seeds with fluorescent signals concentrated at the micropylar end, L: R3 young pod showing developing seeds, M: R5 pod showing developing seeds, N: R5 seed, cross and longitudinal sections showing that the fluorescent signals are in seed coat, O: R6 pod showing a full size seed, P: Old seeds, cross section showing that the fluorescent signals are in seed coat.

Figure 8:
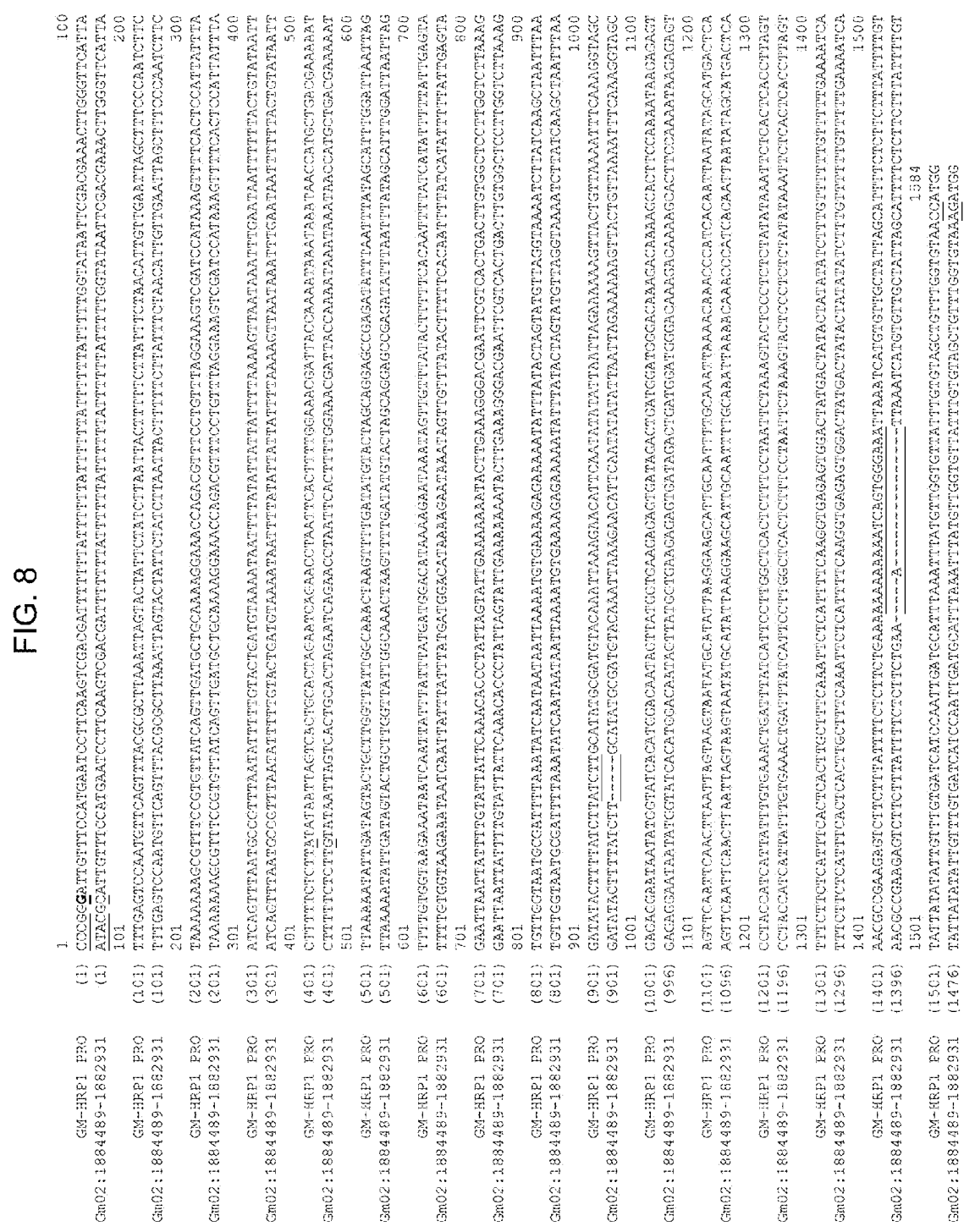

FIG. 8 shows a nucleotide alignment of SEQ ID NO: 1, comprising the HRP1promoter of the disclosure, and SEQ ID NO: 45, comprising a 1559 bp native soybean genomic DNA from Gm02:1884489-1882931 (Schmutz J. et al., Genome sequence of the palaeopolyploid soybean, Nature 463:178-183, 2010). Discrepant positions are underlined. The percent sequence identity between the two sequences based on the Clustal V method of alignment with pairwise alignment default parameters (KTUPLE=2, GAP PENALTY=5, WINDOW=4 and DIAGONALS SAVED=4) is given on the top right.

The sequence descriptions summarize the Sequence Listing attached hereto. The Sequence Listing contains one letter codes for nucleotide sequence characters and the single and three letter codes for amino acids as defined in the IUPAC-IUB standards described in *Nucleic Acids Research* 13:3021-3030 (1985) and in the *Biochemical Journal* 219 (2):345-373 (1984).

SEQ ID NO:1 is a 1584 bp (base pair) DNA sequence comprising the full length soybean HRP1 promoter flanked by XmaI (cccggg) and NcoI (ccatgg) restriction sites. Nucleotides 1314-1345 are a part of the 5' UTR (Un-Translated Region) sequence, nucleotides 1346-1565 represent an intron sequence in the 5' UTR, nucleotides 1566-1579 are a part of the 5' UTR.

SEQ ID NO:2 is a 1334 bp 5' end truncated form of the HRP1 promoter shown in SEQ ID NO:1 including a 3' end NcoI cloning site.

SEQ ID NO:3 is a 1149 bp 5' end truncated form of the HRP1 promoter shown in SEQ ID NO:1 including a 3' end NcoI cloning site.

SEQ ID NO:4 is a 930 bp 5' end truncated form of the HRP1 promoter shown in SEQ ID NO:1 including a 3' end NcoI cloning site.

SEQ ID NO:5 is a 721 bp 5' end truncated form of the HRP1 promoter shown in SEQ ID NO:1 including a 3' end NcoI cloning site.

SEQ ID NO:6 is a 606 4 bp 5' end truncated form of the HRP1 promoter shown in SEQ ID NO:1 including a 3' end NcoI cloning site.

SEQ ID NO:7 is a 487 bp 5' end truncated form of the HRP1 promoter shown in SEQ ID NO:1 including a 3' end NcoI cloning site.

SEQ ID NO:8 is a 376 bp 5' end truncated form of the HRP1 promoter shown in SEQ ID NO:1 including a 3' end NcoI cloning site.

SEQ ID NO:9 is a 1359 bp truncated form, with the 220 bp 5' UTR intron removed, of the HRP1 promoter shown in SEQ ID NO:1 including a 3' end NcoI cloning site.

SEQ ID NO:10 is an oligonucleotide primer used as a gene-specific sense primer in the PCR amplification of the full length HRP1 promoter in SEQ ID NO:1 when paired with SEQ ID NO:11. A restriction enzyme XmaI recognition site CCCGGG is included for subsequent cloning.

SEQ ID NO:11 is an oligonucleotide primer used as a gene-specific antisense primer in the PCR amplification of the full length HRP1 promoter in SEQ ID NO:1 when paired with SEQ ID NO:10, and in the PCR amplifications of the truncated HRP1 promoters in SEQ ID NOs:2, 3, 4, 5, 6, 7, or 8 when paired with SEQ ID NOs: 12, 13, 14, 15, 16, 17, or 18, respectively. A restriction enzyme NcoI recognition site CCATGG is included for subsequent cloning.

SEQ ID NO:12 is an oligonucleotide primer used as a sense primer in the PCR amplification of the truncated HRP1 promoter in SEQ ID NO:2 when paired with SEQ ID NO:11. A restriction enzyme XmaI recognition site CCCGGG is included for subsequent cloning.

SEQ ID NO:13 is an oligonucleotide primer used as a sense primer in the PCR amplification of the truncated HRP1 promoter in SEQ ID NO:3 when paired with SEQ ID NO:11. A restriction enzyme XmaI recognition site CCCGGG is included for subsequent cloning.

SEQ ID NO:14 is an oligonucleotide primer used as a sense primer in the PCR amplification of the truncated HRP1 promoter in SEQ ID NO:4 when paired with SEQ ID NO:11. A restriction enzyme XmaI recognition site CCCGGG is included for subsequent cloning.

SEQ ID NO:15 is an oligonucleotide primer used as a sense primer in the PCR amplification of the truncated HRP1 promoter in SEQ ID NO:5 when paired with SEQ ID NO:11. A restriction enzyme XmaI recognition site CCCGGG is included for subsequent cloning.

SEQ ID NO:16 is an oligonucleotide primer used as a sense primer in the PCR amplification of the truncated HRP1 promoter in SEQ ID NO:6 when paired with SEQ ID NO:11. A restriction enzyme XmaI recognition site CCCGGG is included for subsequent cloning.

SEQ ID NO:17 is an oligonucleotide primer used as a sense primer in the PCR amplification of the truncated HRP1 promoter in SEQ ID NO:7 when paired with SEQ ID NO:17. A restriction enzyme XmaI recognition site CCCGGG is included for subsequent cloning.

SEQ ID NO:18 is an oligonucleotide primer used as a sense primer in the PCR amplification of the truncated HRP1 promoter in SEQ ID NO:8 when paired with SEQ ID NO:11. A restriction enzyme XmaI recognition site CCCGGG is included for subsequent cloning.

SEQ ID NO:19 is an oligonucleotide primer used as a gene-specific antisense primer in the PCR amplification of the truncated HRP1 promoter in SEQ ID NO:9 when paired with SEQ ID NO:10. The 220 bp 5' UTR intron of the HRP1 promoter is removed by the PCR amplification. A restriction enzyme NcoI recognition site CCATGG is included for subsequent cloning.

SEQ ID NO:20 is the 1167 bp nucleotide sequence of the putative soybean hypersensitive-induced response protein HRP1 cDNA (PSO401672 corresponding to Glyma02g02550.1). Nucleotides 1 to 47 are the 5' untranslated sequence, nucleotides 48 to 50 are the translation initiation codon, nucleotides 48 to 908 are the polypeptide coding region, nucleotides 909 to 911 are the termination codon, and nucleotides 912 to 1167 are part of the 3' untranslated sequence.

SEQ ID NO:21 is the predicted 287 aa (amino acid) long peptide sequence translated from the coding region of the putative soybean hypersensitive-induced response protein HRP1 nucleotide sequence SEQ ID NO:20.

SEQ ID NO:22 is the 4927 bp sequence of plasmid QC641.

SEQ ID NO:23 is the 8482 bp sequence of plasmid QC478i.

SEQ ID NO:24 is the 9526 bp sequence of plasmid QC650.

SEQ ID NO:25 is the 4683 bp sequence of plasmid QC641-1.

SEQ ID NO:26 is the 9282 bp sequence of plasmid QC641-1G.

SEQ ID NO:27 is a sense primer used in quantitative PCR analysis of SAMS:HRA transgene copy numbers.

SEQ ID NO:28 is a FAM labeled fluorescent DNA oligo probe used in quantitative PCR analysis of SAMS:HRA transgene copy numbers.

SEQ ID NO:29 is an antisense primer used in quantitative PCR analysis of SAMS:HRA transgene copy numbers.

SEQ ID NO:30 is a sense primer used in quantitative PCR analysis of GM-HRP1:GFP transgene copy numbers.

SEQ ID NO:31 is a FAM labeled fluorescent DNA oligo probe used in quantitative PCR analysis of GM-HRP1:GFP transgene copy numbers.

SEQ ID NO:32 is an antisense primer used in quantitative PCR analysis of GM-HRP1:GFP transgene copy numbers.

SEQ ID NO:33 is a sense primer used as an endogenous control gene primer in quantitative PCR analysis of transgene copy numbers.

SEQ ID NO:34 is a VIC labeled DNA oligo probe used as an endogenous control gene probe in quantitative PCR analysis of transgene copy numbers.

SEQ ID NO:35 is an antisense primer used as an endogenous control gene primer in quantitative PCR analysis of transgene copy numbers.

SEQ ID NO:36 is the recombination site attL1 sequence in the GATEWAY® cloning system (Invitrogen, Carlsbad, Calif.).

SEQ ID NO:37 is the recombination site attL2 sequence in the GATEWAY® cloning system (Invitrogen).

SEQ ID NO:38 is the recombination site attR1 sequence in the GATEWAY® cloning system (Invitrogen).

SEQ ID NO:39 is the recombination site attR2 sequence in the GATEWAY® cloning system (Invitrogen).

SEQ ID NO:40 is the recombination site attB1 sequence in the GATEWAY® cloning system (Invitrogen).

SEQ ID NO:41 is the recombination site attB2 sequence in the GATEWAY® cloning system (Invitrogen).

SEQ ID NO:42 is the 1267 bp nucleotide sequence of the *Glycine max* hypersensitive-induced response protein 1-like gene (NCBI accession XM_003519030.1) similar to the HRP1 gene (PSO401672) sequence SEQ ID NO:20.

SEQ ID NO:43 is the 267 by 5' UTR region of GM-HRP1 promoter including the 47 by 5' UTR of PS401672 interrupted by a 220 by intron.

SEQ ID NO:44 is a 47 bp fragment of the 5' end untranslated region of the GM-HRP1 gene PSO401672.

SEQ ID NO: 45 is a 1559 bp fragment of native soybean genomic DNA Gm02:1884489-1882931 complementary strand sequence from cultivar "Williams82" (Schmutz J. et al. Nature 463: 178-183, 2010).

DETAILED DESCRIPTION OF THE INVENTION

The disclosure of all patents, patent applications, and publications cited herein are incorporated by reference in their entirety.

As used herein and in the appended claims, the singular forms "a", "an", and "the" include plural reference unless the context clearly dictates otherwise. Thus, for example, reference to "a plant" includes a plurality of such plants; reference to "a cell" includes one or more cells and equivalents thereof known to those skilled in the art, and so forth.

In the context of this disclosure, a number of terms shall be utilized.

An "isolated polynucleotide" refers to a polymer of ribonucleotides (RNA) or deoxyribonucleotides (DNA) that is single- or double-stranded, optionally containing synthetic, non-natural or altered nucleotide bases. An isolated polynucleotide in the form of DNA may be comprised of one or more segments of cDNA, genomic DNA or synthetic DNA.

The terms "polynucleotide", "polynucleotide sequence", "nucleic acid sequence", "nucleic acid fragment", and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A "soybean HRP1 promoter", "GM-HRP1 promoter" or "HRP1 promoter" are used interchangeably herein, and refer to the promoter of a putative Glycine max gene with significant homology to hypersensitive-induced response protein (HRP1) genes identified in various plant species including soybean that are deposited in National Center for Biotechnology Information (NCBI) database. The term "soybean HRP1 promoter" encompasses both a native soybean promoter and an engineered sequence comprising a fragment of the native soybean promoter with a DNA linker attached to facilitate cloning. A DNA linker may comprise a restriction enzyme site.

"Promoter" refers to a nucleic acid fragment capable of controlling transcription of another nucleic acid fragment. A promoter is capable of controlling the expression of a coding sequence or functional RNA. Functional RNA includes, but is not limited to, transfer RNA (tRNA) and ribosomal RNA (rRNA). The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. New promoters of various types useful in plant cells are constantly being discovered; numerous examples may be found in the compilation by Okamuro and Goldberg (Biochemistry of Plants 15:1-82 (1989)). It is further recognized that since in most cases the exact boundaries of regulatory sequences have not been completely defined, DNA fragments of some variation may have identical promoter activity.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Embryo-specific promoter" and "embryo-preferred promoter" are used interchangeably to refer to a promoter that is active during embryo development or expressed predominantly but not necessarily exclusively in embryo tissue.

"Developmentally regulated promoter" refers to a promoter whose activity is determined by developmental events.

"Constitutive promoter" refers to promoters active in all or most tissues or cell types of a plant at all or most developing stages. As with other promoters classified as "constitutive" (e.g. ubiquitin), some variation in absolute levels of expression can exist among different tissues or stages. The term "constitutive promoter" or "tissue-independent" are used interchangeably herein.

The HRP1 promoter nucleotide sequences and methods disclosed herein are useful in regulating tissue-specific expression of any heterologous nucleotide sequences in a host plant in order to alter the phenotype of a plant. The tissues in which the HRP1 promoter is specifically expressed include anther tapetum, ovule inner integument and nucellus, very young embryo, and seed coat.

A "heterologous nucleotide sequence" refers to a sequence that is not naturally occurring with the plant promoter sequence of the invention. While this nucleotide sequence is heterologous to the promoter sequence, it may be homologous, or native, or heterologous, or foreign, to the plant host. However, it is recognized that the instant promoters may be used with their native coding sequences to increase or decrease expression resulting in a change in phenotype in the transformed seed. The terms "heterologous nucleotide sequence", "heterologous sequence", "heterologous nucleic acid fragment", and "heterologous nucleic acid sequence" are used interchangeably herein.

Among the most commonly used promoters are the nopaline synthase (NOS) promoter (Ebert et al., Proc. Natl. Acad. Sci. U.S.A. 84:5745-5749 (1987)), the octapine synthase (OCS) promoter, caulimovirus promoters such as the cauliflower mosaic virus (CaMV) 19S promoter (Lawton et al., Plant Mol. Biol. 9:315-324 (1987)), the CaMV 35S promoter (Odell et al., Nature 313:810-812 (1985)), and the figwort mosaic virus 35S promoter (Sanger et al., Plant Mol. Biol. 14:433-43 (1990)), the light inducible promoter from the small subunit of rubisco, the Adh promoter (Walker et al., Proc. Natl. Acad. Sci. U.S.A. 84:6624-66280 (1987), the sucrose synthase promoter (Yang et al., Proc. Natl. Acad. Sci. U.S.A. 87:4144-4148 (1990)), the R gene complex promoter (Chandler et al., Plant Cell 1:1175-1183 (1989)), the chlorophyll a/b binding protein gene promoter, etc. Other commonly used promoters are, the promoters for the potato tuber ADPGPP genes, the sucrose synthase promoter, the granule bound starch synthase promoter, the glutelin gene promoter, the maize waxy promoter, Brittle gene promoter, and Shrunken 2 promoter, the acid chitinase gene promoter, and the zein gene promoters (15 kD, 16 kD, 19 kD, 22 kD, and 27 kD; Perdersen et al., Cell 29:1015-1026 (1982)). A plethora of promoters is described in PCT Publication No. WO 00/18963 published on Apr. 6, 2000, the disclosure of which is hereby incorporated by reference.

The present invention encompasses functional fragments of the promoter sequences disclosed herein.

A "functional fragment" refer to a portion or subsequence of the promoter sequence of the present invention in which the ability to initiate transcription or drive gene expression (such as to produce a certain phenotype) is retained. Fragments can be obtained via methods such as site-directed mutagenesis and synthetic construction. As with the provided promoter sequences described herein, the functional fragments operate to promote the expression of an operably linked heterologous nucleotide sequence, forming a recombinant DNA construct (also, a chimeric gene). For example, the fragment can be used in the design of recombinant DNA constructs to produce the desired phenotype in a transformed plant. Recombinant DNA constructs can be designed for use in co-suppression or antisense by linking a promoter fragment in the appropriate orientation relative to a heterologous nucleotide sequence.

A nucleic acid fragment that is functionally equivalent to the promoter of the present invention is any nucleic acid fragment that is capable of controlling the expression of a coding sequence or functional RNA in a similar manner to the promoter of the present invention.

In an embodiment of the present invention, the promoters disclosed herein can be modified. Those skilled in the art can create promoters that have variations in the polynucleotide sequence. The polynucleotide sequence of the promoters of the present invention as shown in SEQ ID NOS: 1-9, may be modified or altered to enhance their control characteristics. As one of ordinary skill in the art will appreciate, modification or alteration of the promoter sequence can also be made without substantially affecting the promoter function. The methods are well known to those of skill in the art. Sequences can be modified, for example by insertion, deletion, or replacement of template sequences in a PCR-based DNA modification approach.

A "variant promoter", as used herein, is the sequence of the promoter or the sequence of a functional fragment of a promoter containing changes in which one or more nucleotides of the original sequence is deleted, added, and/or substituted, while substantially maintaining promoter function. One or more base pairs can be inserted, deleted, or substituted internally to a promoter. In the case of a promoter fragment, variant promoters can include changes affecting the transcription of a minimal promoter to which it is operably linked. Variant promoters can be produced, for example, by standard DNA mutagenesis techniques or by chemically synthesizing the variant promoter or a portion thereof.

Methods for construction of chimeric and variant promoters of the present invention include, but are not limited to, combining control elements of different promoters or duplicating portions or regions of a promoter (see for example, U.S. Pat. Nos. 4,990,607; 5,110,732; and 5,097,025). Those of skill in the art are familiar with the standard resource materials that describe specific conditions and procedures for the construction, manipulation, and isolation of macromolecules (e.g., polynucleotide molecules and plasmids), as well as the generation of recombinant organisms and the screening and isolation of polynucleotide molecules.

In some aspects of the present invention, the promoter fragments can comprise a deletion at the 5'-terminus of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 11511, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207 or 1208 contiguous nucleotides of SEQ ID NO:1.

In other embodiments, the promoter fragments can comprise at least about 20 or at least about 50 contiguous nucleotides, or at least about 75 contiguous nucleotides, or at least about 100 contiguous nucleotides, or at least about 150 contiguous nucleotides, or at least about 200 contiguous nucleotides of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 or SEQ ID NO: 45. In another aspect of the present invention, the promoter fragments can comprise at least about 250 contiguous nucleotides, or at least about 300 contiguous nucleotides, or at least about 350 contiguous nucleotides, or at least about 400 contiguous nucleotides, or at least about 450 contiguous nucleotides, or at least about 500 contiguous nucleotides, or at least about 550 contiguous nucleotides, or at least about 600 contiguous nucleotides, or at least about 650 contiguous nucleotides, or at least about 700 contiguous nucleotides, or at least about 750 contiguous nucleotides, or at least about 800 contiguous nucleotides, or at least about 850 contiguous nucleotides, or at least about 900 contiguous nucleotides, or at least about 950 contiguous nucleotides, or at least about 1000 contiguous nucleotides, or at least about 1050 contiguous nucleotides, or at least about 1100 contiguous nucleotides, or at least about 1150 contiguous nucleotides, or at least about 1200 contiguous nucleotides of SEQ ID NO:1.

In another aspect, a promoter fragment is the nucleotide sequence set forth in SEQ ID NO:2, SEQ ID NO:3, SEQ ID NO:4, SEQ ID NO:5, SEQ ID NO:6, SEQ ID NO:7, SEQ ID NO:8, SEQ ID NO:9 or SEQ ID NO: 45. The nucleotides of such fragments will usually comprise the TATA recognition sequence of the particular promoter sequence. Such fragments may be obtained by use of restriction enzymes to cleave the naturally occurring promoter nucleotide sequences disclosed herein, by synthesizing a nucleotide sequence from the naturally occurring promoter DNA sequence, or may be obtained through the use of PCR technology. See particularly, Mullis et al., Methods Enzymol. 155:335-350 (1987), and Higuchi, R. In PCR Technology: Principles and Applications for DNA Amplifications; Erlich, H. A., Ed.; Stockton Press Inc.: New York, 1989.

The terms "full complement" and "full-length complement" are used interchangeably herein, and refer to a complement of a given nucleotide sequence, wherein the complement and the nucleotide sequence consist of the same number of nucleotides and are 100% complementary.

The terms "substantially similar" and "corresponding substantially" as used herein refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

The isolated promoter sequence of the present invention can be modified to provide a range of tissue-specific expression levels of the heterologous nucleotide sequence. Thus, less than the entire promoter regions may be utilized and the ability to drive expression of the coding sequence retained. However, it is recognized that expression levels of the mRNA may be decreased with deletions of portions of the promoter sequences. Likewise, the tissue-specific nature of expression may be changed.

Modifications of the isolated promoter sequences of the present invention can provide for a range of tissue-specific expression of the heterologous nucleotide sequence. Thus, they may be modified to be weak tissue-specific promoters or strong tissue-specific promoters. Generally, by "weak promoter" is intended a promoter that drives expression of a coding sequence at a low level. By "low level" is intended at levels about $\frac{1}{10,000}$ transcripts to about $\frac{1}{100,000}$ transcripts to about $\frac{1}{500,000}$ transcripts. Conversely, a strong promoter drives expression of a coding sequence at high level, or at about $\frac{1}{10}$ transcripts to about $\frac{1}{100}$ transcripts to about $\frac{1}{1,000}$ transcripts.

Moreover, the skilled artisan recognizes that substantially similar nucleic acid sequences encompassed by this invention are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the invention. Estimates of such homology are provided by either DNA-DNA or DNA-RNA hybridization under conditions of stringency as is well understood by those skilled in the art (Hames and Higgins, Eds.; In Nucleic Acid Hybridisation; IRL Press: Oxford, U. K., 1985). Stringency conditions can be adjusted to screen for moderately similar fragments, such as homologous sequences from distantly related organisms, to highly similar fragments, such as genes that duplicate functional enzymes from closely related organisms. Post-hybridization washes partially determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of stringent conditions uses higher temperatures in which the washes are identical to those above except for the temperature of the final two 30 min washes in 0.2× SSC, 0.5% SDS was increased to 60° C. Another set of highly stringent conditions uses two final washes in 0.1×SSC, 0.1% SDS at 65° C.

Preferred substantially similar nucleic acid sequences encompassed by this invention are those sequences that are 80% identical to the nucleic acid fragments reported herein or which are 80% identical to any portion of the nucleotide sequences reported herein. More preferred are nucleic acid fragments which are 90% identical to the nucleic acid sequences reported herein, or which are 90% identical to any portion of the nucleotide sequences reported herein. Most preferred are nucleic acid fragments which are 95% identical to the nucleic acid sequences reported herein, or which are 95% identical to any portion of the nucleotide sequences reported herein. It is well understood by one skilled in the art that many levels of sequence identity are useful in identifying related polynucleotide sequences. Useful examples of percent identities are those listed above, or also preferred is any integer percentage from 72% to 100%, such as 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100%.

In one embodiment, this invention concerns a recombinant DNA construct comprising an isolated polynucleotide comprising a promoter wherein said promoter comprises a nucleotide sequence having at least 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% sequence identity, based on the Clustal V method of alignment with pairwise alignment default parameters (KTUPLE=2, GAP PENALTY=5, WINDOW=4 and DIAGONALS SAVED=4) when compared to the nucleotide sequence of SEQ ID NO:1. As described in Example 2, comparison of SEQ ID NO:1 to a soybean cDNA library revealed that SEQ ID NOs: 1, 2, 3, 4, 5, 6, 7, 8, 9 and 43 comprise a 5' untranslated region (5'UTR) of at least 47 base pairs (SEQ ID NO:44) interrupted by a 220 bp intron in a total length of 267 bp (SEQ ID NO:45). It is known to one of skilled in the art that a 5' UTR region can be altered (deletion or substitutions of bases) or replaced by an alternative 5'UTR while maintaining promoter activity.

This 5'UTR region represents (267/1584)*100=16.9% of SEQ ID NO:1, (267/1334)*100=20.0% of SEQ ID NO:2, (267/1149)*100=23.2% of SEQ ID NO:3, (267/930)*10=28.7% of SEQ ID NO:4, (267/721)*100=37.0% of SEQ ID NO:5, (267/606)*100=44.0% of SEQ ID NO:6, (267/487)*100=54.8% of SEQ ID NO:7, (267/376)*100=71.01% of SEQ ID NO:8, and (47/1359 with the 220 bp intron deleted)*100=3.4% of SEQ ID NO:9 respectively, indicating that an isolated polynucleotide of 83.1% sequence identity to SEQ ID NO:1, or 80.0% sequence identity to SEQ ID NO:2, or 76.8% sequence identity to SEQ ID NO:3, or 71.3% sequence identity to SEQ ID NO:4, or 63.0% % sequence identity to SEQ ID NO:5, or 66.0% sequence identity to SEQ ID NO:6, or 45.2% sequence identity to SEQ ID NO:7, or 29% sequence identity to SEQ ID NO:8, or 96.6% sequence identity to SEQ ID NO:9 can be generated while maintaining promoter activity. Alternatively, the 220 bp 5' UTR intron may be a critical part of the HRP1 promoter that cannot be removed without compromising HRP1 promoter activity.

A "substantially homologous sequence" refers to variants of the disclosed sequences such as those that result from site-directed mutagenesis, as well as synthetically derived sequences. A substantially homologous sequence of the present invention also refers to those fragments of a particular promoter nucleotide sequence disclosed herein that operate to promote the tissue-specific expression of an operably linked heterologous nucleic acid fragment. These promoter fragments will comprise at least about 20 contiguous nucleotides, preferably at least about 50 contiguous nucleotides, more preferably at least about 75 contiguous nucleotides, even more preferably at least about 100 contiguous nucleotides of the particular promoter nucleotide sequence disclosed herein. The nucleotides of such fragments will usually comprise the TATA recognition sequence of the particular promoter sequence. Such fragments may be obtained by use of restriction enzymes to cleave the naturally occurring promoter nucleotide sequences disclosed herein; by synthesizing a nucleotide sequence from the naturally occurring promoter DNA sequence; or may be obtained through the use of PCR technology. See particularly, Mullis et al., Methods Enzymol. 155:335-350 (1987), and Higuchi, R. In PCR Technology: Principles and Applications for DNA Amplifications; Erlich, H. A., Ed.; Stockton Press Inc.: New York, 1989. Again, variants of these promoter fragments, such as those resulting from site-directed mutagenesis, are encompassed by the compositions of the present invention.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp (1989) CABIOS. 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Alternatively, the Clustal W method of alignment may be used. The Clustal W method of alignment (described by Higgins and Sharp, CABIOS. 5:151-153 (1989); Higgins, D. G. et al., Comput. Appl. Biosci. 8:189-191 (1992)) can be found in the MegAlign™ v6.1 program of the LASERGENE® bioinformatics computing suite (DNASTAR® Inc., Madison, Wis.). Default parameters for multiple alignment correspond to GAP PENALTY=10, GAP LENGTH PENALTY=0.2, Delay Divergent Sequences=30%, DNA Transition Weight=0.5, Protein Weight Matrix=Gonnet Series, DNA Weight Matrix=IUB. For pairwise alignments the default parameters are Alignment=Slow-Accurate, Gap Penalty=10.0, Gap Length=0.10, Protein Weight Matrix=Gonnet 250 and DNA Weight Matrix=IUB. After alignment of the sequences using the Clustal W program, it is possible to obtain "percent identity" and "divergence" values by viewing the "sequence distances" table in the same program.

In one embodiment the % sequence identity is determined over the entire length of the molecule (nucleotide or amino acid).

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F. et al., J. Mol. Biol. 215:403-410 (1993)) and Gapped Blast (Altschul, S. F. et al., Nucleic Acids Res. 25:3389-3402 (1997)). BLASTN refers to a BLAST program that compares a nucleotide query sequence against a nucleotide sequence database.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "recombinant expression construct", which are used interchangeably, refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

An "intron" is an intervening sequence in a gene that is transcribed into RNA but is then excised in the process of generating the mature mRNA. The term is also used for the excised RNA sequences. An "exon" is a portion of the sequence of a gene that is transcribed and is found in the mature messenger RNA derived from the gene, but is not necessarily a part of the sequence that encodes the final gene product.

The "translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., Molecular Biotechnology 3:225 (1995)).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., Plant Cell 1:671-680 (1989).

"RNA transcript" refers to a product resulting from RNA polymerase-catalyzed transcription of a DNA sequence. When an RNA transcript is a perfect complementary copy of a DNA sequence, it is referred to as a primary transcript or it may be a RNA sequence derived from posttranscriptional processing of a primary transcript and is referred to as a mature RNA. "Messenger RNA" ("mRNA") refers to RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded by using the Klenow fragment of DNA polymerase I. "Sense" RNA refers to RNA transcript that includes mRNA and so can be translated into protein within a cell or in vitro. "Antisense RNA" refers to a RNA transcript that is complementary to all or part of a target primary transcript or mRNA and that blocks expression or transcripts accumulation of a target gene (U.S. Pat. No. 5,107,065). The complementarity of an antisense RNA may be with any part of the specific gene transcript, i.e. at the 5' non-coding sequence, 3' non-coding sequence, introns, or the coding sequence. "Functional RNA" refers to antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The terms "initiate transcription", "initiate expression", "drive transcription", and "drive expression" are used interchangeably herein and all refer to the primary function of a promoter. As detailed throughout this disclosure, a promoter is a non-coding genomic DNA sequence, usually upstream (5') to the relevant coding sequence, and its primary function is to act as a binding site for RNA polymerase and initiate transcription by the RNA polymerase. Additionally, there is "expression" of RNA, including functional RNA, or the expression of polypeptide for operably linked encoding nucleotide sequences, as the transcribed RNA ultimately is translated into the corresponding polypeptide.

The term "expression", as used herein, refers to the production of a functional end-product e.g., an mRNA or a protein (precursor or mature).

The term "expression cassette" as used herein, refers to a discrete nucleic acid fragment into which a nucleic acid sequence or fragment can be moved.

Expression or overexpression of a gene involves transcription of the gene and translation of the mRNA into a precursor or mature protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression or transcript accumulation of identical or substantially similar foreign or endogenous genes (U.S. Pat. No. 5,231,020). The mechanism of cosuppression may be at the DNA level (such as DNA methylation), at the transcriptional level, or at posttranscriptional level.

Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al., Plant J. 16:651-659 (1998); and Gura, Nature 404:804-808 (2000)). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication No. WO 99/53050 published on Oct. 21, 1999; and PCT Publication No. WO 02/00904 published on Jan. 3, 2002). This increases the frequency of co-suppression in the recovered transgenic plants. Another variation describes the use of plant viral sequences to direct the suppression, or "silencing", of proximal mRNA encoding sequences (PCT Publication No. WO 98/36083 published on Aug. 20, 1998). Genetic and molecular evidences have been obtained suggesting that dsRNA mediated mRNA cleavage may have been the conserved mechanism underlying these gene silencing phenomena (Elmayan et al., Plant Cell 10:1747-1757 (1998); Galun, In Vitro Cell. Dev. Biol. Plant 41(2):113-123 (2005); Pickford et al, Cell. Mol. Life Sci. 60(5):871-882 (2003)).

As stated herein, "suppression" refers to a reduction of the level of enzyme activity or protein functionality (e.g., a phenotype associated with a protein) detectable in a transgenic plant when compared to the level of enzyme activity or protein functionality detectable in a non-transgenic or wild type plant with the native enzyme or protein. The level of enzyme activity in a plant with the native enzyme is referred to herein as "wild type" activity. The level of protein functionality in a plant with the native protein is referred to herein as "wild type" functionality. The term "suppression" includes lower, reduce, decline, decrease, inhibit, eliminate and prevent. This reduction may be due to a decrease in translation of the native mRNA into an active enzyme or functional protein. It may also be due to the transcription of the native DNA into decreased amounts of mRNA and/or to rapid degradation of the native mRNA. The term "native enzyme" refers to an enzyme that is produced naturally in a non-transgenic or wild type cell. The terms "non-transgenic" and "wild type" are used interchangeably herein.

"Altering expression" refers to the production of gene product(s) in transgenic organisms in amounts or proportions that differ significantly from the amount of the gene product(s) produced by the corresponding wild-type organisms (i.e., expression is increased or decreased).

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation. Host organisms containing the transformed nucleic acid fragments are referred to as "transgenic" organisms.

"Transient transformation" refers to the introduction of a nucleic acid fragment into the nucleus, or DNA-containing organelle, of a host organism resulting in gene expression without genetically stable inheritance.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

The terms "monocot" and "monocotyledonous plant" are used interchangeably herein. A monocot of the current invention includes the Gramineae.

The terms "dicot" and "dicotyledonous plant" are used interchangeably herein. A dicot of the current invention includes the following families: Brassicaceae, Leguminosae, and Solanaceae.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

"Transient expression" refers to the temporary expression of often reporter genes such as β-glucuronidase (GUS), fluorescent protein genes ZS-GREEN1, ZS-YELLOW1 N1, AM-CYAN1, DS-RED in selected certain cell types of the host organism in which the transgenic gene is introduced temporally by a transformation method. The transformed materials of the host organism are subsequently discarded after the transient gene expression assay.

Standard recombinant DNA and molecular cloning techniques used herein are well known in the art and are described more fully in Sambrook, J. et al., In Molecular Cloning: A Laboratory Manual; 2$^{nd}$ ed.; Cold Spring Harbor Laboratory Press: Cold Spring Harbor, N. Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In Current Protocols in Molecular Biology; John Wiley and Sons: New York, 1990 (hereinafter "Ausubel et al., 1990").

"PCR" or "Polymerase Chain Reaction" is a technique for the synthesis of large quantities of specific DNA segments, consisting of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps comprises a cycle.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "recombinant DNA construct" or "recombinant expression construct" is used interchangeably and refers to a discrete polynucleotide into which a nucleic acid sequence or fragment can be moved. Preferably, it is a plasmid vector or a fragment thereof comprising the promoters of the present invention. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., EMBO J. 4:2411-2418 (1985); De Almeida et al., Mol. Gen. Genetics 218:78-86 (1989)), and thus that multiple events must be screened in order to obtain lines displaying the desired expression level and pattern. Such screening may be accomplished by PCR and Southern analysis of DNA, RT-PCR and Northern analysis of mRNA expression, Western analysis of protein expression, or phenotypic analysis.

Various changes in phenotype are of interest including, but not limited to, modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic characteristics and traits such as yield and heterosis increase, the choice of genes for transformation will change accordingly. General categories of genes of interest include, but are not limited to, those genes involved in information, such as zinc fingers, those involved in communication, such as kinases, and those involved in housekeeping, such as heat shock proteins. More specific categories of transgenes, for example, include, but are not limited to, genes encoding important traits for agronomics, insect resistance, disease resistance, herbicide resistance, sterility, grain or seed characteristics, and commercial products. Genes of interest include, generally, those involved in oil, starch, carbohydrate, or nutrient metabolism as well as those affecting seed size, plant development, plant growth regulation, and yield improvement. Plant development and growth regulation also refer to the development and growth regulation of various parts of a plant, such as the flower, seed, root, leaf and shoot.

Other commercially desirable traits are genes and proteins conferring cold, heat, salt, and drought resistance.

Disease and/or insect resistance genes may encode resistance to pests that have great yield drag such as for example, anthracnose, soybean mosaic virus, soybean cyst nematode, root-knot nematode, brown leaf spot, Downy mildew, purple seed stain, seed decay and seedling diseases caused commonly by the fungi—*Pythium* sp., *Phytophthora* sp., *Rhizoctonia* sp., *Diaporthe* sp. Bacterial blight caused by the bacterium *Pseudomonas syringae* pv. *Glycinea*. Genes conferring insect resistance include, for example, *Bacillus thuringiensis* toxic protein genes (U.S. Pat. Nos. 5,366,892; 5,747,450; 5,737,514; 5,723,756; 5,593,881; and Geiser et al (1986) Gene 48:109); lectins (Van Damme et al. (1994) Plant Mol. Biol. 24:825); and the like.

Herbicide resistance traits may include genes coding for resistance to herbicides that act to inhibit the action of acetolactate synthase (ALS), in particular the sulfonylurea-type herbicides (e.g., the acetolactate synthase ALS gene containing mutations leading to such resistance, in particular the S4 and/or HRA mutations). The ALS-gene mutants encode resistance to the herbicide chlorsulfuron. Glyphosate acetyl transferase (GAT) is an N-acetyltransferase from *Bacillus licheniformis* that was optimized by gene shuffling for acetylation of the broad spectrum herbicide, glyphosate, forming the basis of a novel mechanism of glyphosate tolerance in transgenic plants (Castle et al. (2004) *Science* 304, 1151-1154).

Antibiotic resistance genes include, for example, neomycin phosphotransferase (npt) and hygromycin phosphotransferase (hpt). Two neomycin phosphotransferase genes are used in selection of transformed organisms: the neomycin phosphotransferase I (nptI) gene and the neomycin phosphotransferase II (nptII) gene. The second one is more widely used. It was initially isolated from the transposon Tn5 that was present in the bacterium strain *Escherichia coli* K12. The gene codes for the aminoglycoside 3'-phosphotransferase (denoted aph(3')-II or NPTII) enzyme, which inactivates by phosphorylation a range of aminoglycoside antibiotics such as kanamycin, neomycin, geneticin and paroromycin. NPTII is widely used as a selectable marker for plant transformation. It is also used in gene expression and regulation studies in different organisms in part because N-terminal fusions can be constructed that retain enzyme activity. NPTII protein activity can be detected by enzymatic assay. In other detection methods, the modified substrates, the phosphorylated antibiotics, are detected by thin-layer chromatography, dot-blot analysis or polyacrylamide gel electrophoresis. Plants such as maize, cotton, tobacco, *Ara-* bidopsis, flax, soybean and many others have been successfully transformed with the nptII gene.

The hygromycin phosphotransferase (denoted hpt, hph or aphIV) gene was originally derived from *Escherichia coli*. The gene codes for hygromycin phosphotransferase (HPT), which detoxifies the aminocyclitol antibiotic hygromycin B. A large number of plants have been transformed with the hpt gene and hygromycin B has proved very effective in the selection of a wide range of plants, including monocotyledonous. Most plants exhibit higher sensitivity to hygromycin B than to kanamycin, for instance cereals. Likewise, the hpt gene is used widely in selection of transformed mammalian cells. The sequence of the hpt gene has been modified for its use in plant transformation. Deletions and substitutions of amino acid residues close to the carboxy (C)-terminus of the enzyme have increased the level of resistance in certain plants, such as tobacco. At the same time, the hydrophilic C-terminus of the enzyme has been maintained and may be essential for the strong activity of HPT. HPT activity can be checked using an enzymatic assay. A non-destructive callus induction test can be used to verify hygromycin resistance.

Genes involved in plant growth and development have been identified in plants. One such gene, which is involved in cytokinin biosynthesis, is isopentenyl transferase (IPT). Cytokinin plays a critical role in plant growth and development by stimulating cell division and cell differentiation (Sun et al. (2003), Plant Physiol. 131: 167-176).

Calcium-dependent protein kinases (CDPK), a family of serine-threonine kinase found primarily in the plant kingdom, are likely to function as sensor molecules in calcium-mediated signaling pathways. Calcium ions are important second messengers during plant growth and development (Harper et al. Science 252, 951-954 (1993); Roberts et al. Curr. Opin. Cell Biol. 5, 242-246 (1993); Roberts et al. Annu. Rev. Plant Mol. Biol. 43, 375-414 (1992)).

Nematode responsive protein (NRP) is produced by soybean upon the infection of soybean cyst nematode. NRP has homology to a taste-modifying glycoprotein miraculin and the NF34 protein involved in tumor formation and hyper response induction. NRP is believed to function as a defense-inducer in response to nematode infection (Tenhaken et al. BMC Bioinformatics 6:169 (2005)).

The quality of seeds and grains is reflected in traits such as levels and types of fatty acids or oils, saturated and unsaturated, quality and quantity of essential amino acids, and levels of carbohydrates. Therefore, commercial traits can also be encoded on a gene or genes that could increase for example methionine and cysteine, two sulfur containing amino acids that are present in low amounts in soybeans. Cystathionine gamma synthase (CGS) and serine acetyl transferase (SAT) are proteins involved in the synthesis of methionine and cysteine, respectively.

Other commercial traits can encode genes to increase for example monounsaturated fatty acids, such as oleic acid, in oil seeds. Soybean oil for example contains high levels of polyunsaturated fatty acids and is more prone to oxidation than oils with higher levels of monounsaturated and saturated fatty acids. High oleic soybean seeds can be prepared by recombinant manipulation of the activity of oleoyl 12-desaturase (Fad2). High oleic soybean oil can be used in applications that require a high degree of oxidative stability, such as cooking for a long period of time at an elevated temperature.

Raffinose saccharides accumulate in significant quantities in the edible portion of many economically significant crop species, such as soybean (*Glycine max* L. Merrill), sugar beet (*Beta vulgaris*), cotton (*Gossypium hirsutum* L.), canola (*Brassica* sp.) and all of the major edible leguminous crops including beans (*Phaseolus* sp.), chick pea (*Cicer arietinum*), cowpea (*Vigna unguiculata*), mung bean (*Vigna radiata*), peas (*Pisum sativum*), lentil (*Lens culinaris*) and lupine (*Lupinus* sp.). Although abundant in many species, raffinose saccharides are an obstacle to the efficient utilization of some economically important crop species.

Down regulation of the expression of the enzymes involved in raffinose saccharide synthesis, such as galactinol synthase for example, would be a desirable trait.

In certain embodiments, the present invention contemplates the transformation of a recipient cell with more than one advantageous transgene. Two or more transgenes can be supplied in a single transformation event using either distinct transgene-encoding vectors, or a single vector incorporating two or more gene coding sequences. Any two or more transgenes of any description, such as those conferring herbicide, insect, disease (viral, bacterial, fungal, and nematode), or drought resistance, oil quantity and quality, or those increasing yield or nutritional quality may be employed as desired.

Hypersensitive-induced response proteins (HIR) are a gene family found in barley, wheat, rice, Lotus japonicas (Rostoks et al., Theor. Appl. Genet. 107:1094-1101 (2003); Yu et al., Gene 407:193-198 (2008); Zhou et al., BMC Plant Biol. 10:290 (2010); Hakozaki et al., Genes Genet. Syst. 79:307-310 (2004)). They are also identified based on sequence homology by genome sequencing projects in *Glycine max, Zea mays, Vitis vinifera, Ricinus communis, Cucumis sativus, Medicago truncatula, Sorghum bicolor, Populus trichocarpa, Brachypodium distachyon* etc. HIR proteins contain the stomatin/prohibitinglotillin/HflK/C (SPFH) domain (also known as the prohibitin (PHB) domain or band 7 domain) and are involved in N-terminal protein myristoylation. They are localized to a variety of cellular membranes, including plasma membrane, Golgi, mitochondria, endoplasmic reticulum, and lipid droplets and have been implicated in cell functions such as ion channel regulation, microdomain formation, membrane protein chaperoning, vesicle trafficking, and membrane-cytoskeletal connection. Some members of the HIR gene family are transcriptionally induced in cells undergoing hypersensitive response (HR), a programmed cell death phenomenon thought to prevent biotrophic pathogens from spreading (Qi et al., J Biol Chem. 286:31297-307 (2011)). It is demonstrated herein that the soybean hypersensitive-induced response protein gene promoter GM-HRP1 can, in fact, be used as a tissue-specific promoter to drive expression of transgenes in plants, and that such promoter can be isolated and used by one skilled in the art.

This invention concerns a recombinant DNA construct comprising an isolated nucleic acid fragment comprising a tissue-specific hypersensitive-induced response protein gene HRP1 promoter. This invention also concerns a recombinant DNA construct comprising an isolated nucleic acid fragment comprising a promoter wherein said promoter consists essentially of the nucleotide sequence set forth in SEQ ID NO:1, or a recombinant DNA construct comprising an isolated polynucleotide comprising a promoter wherein said promoter comprises the nucleotide sequence set forth in SEQ ID NOs: 1, 2, 3, 4, 5, 6, 7, 8, 9 or 45 or a functional fragment of SEQ ID NOs: 1, 2, 3, 4, 5, 6, 7, 8, 9 or 45.

The expression patterns of HRP1 gene and its promoter are set forth in Examples 1-7.

The promoter activity of the soybean genomic DNA fragment SEQ ID NO:1 upstream of the HRP1 protein coding sequence was assessed by linking the fragment to a green fluorescence reporter gene, ZS-GREEN1 (GFP) (Tsien, Annu. Rev. Biochem. 67:509-544 (1998); Matz et al., Nat. Biotechnol. 17:969-973 (1999)), transforming the promoter:GFP expression cassette into soybean, and analyzing GFP expression in various cell types of the transgenic plants (see Example 6 and 7). GFP expression was detected specifically in certain tissues of the transgenic plants. These results indicated that the nucleic acid fragment contained a tissue-specific promoter.

It is clear from the disclosure set forth herein that one of ordinary skill in the art could perform the following procedure:

1) operably linking the nucleic acid fragment containing the HRP1 promoter sequence to a suitable reporter gene; there are a variety of reporter genes that are well known to those skilled in the art, including the bacterial GUS gene, the firefly luciferase gene, and the cyan, green, red, and yellow fluorescent protein genes; any gene for which an easy and reliable assay is available can serve as the reporter gene.

2) transforming a chimeric HRP1 promoter:reporter gene expression cassette into an appropriate plant for expression of the promoter. There are a variety of appropriate plants which can be used as a host for transformation that are well known to those skilled in the art, including the dicots, Arabidopsis, tobacco, soybean, oilseed rape, peanut, sunflower, safflower, cotton, tomato, potato, cocoa and the monocots, corn, wheat, rice, barley and palm.

3) testing for expression of the HRP1 promoter in various cell types of transgenic plant tissues, e.g., leaves, roots, flowers, seeds, transformed with the chimeric HRP1 promoter:reporter gene expression cassette by assaying for expression of the reporter gene product.

In another aspect, this invention concerns a recombinant DNA construct comprising at least one heterologous nucleic acid fragment operably linked to any promoter, or combination of promoter elements, of the present invention. Recombinant DNA constructs can be constructed by operably linking the nucleic acid fragment of the invention HRP1 promoter or a fragment that is substantially similar and functionally equivalent to any portion of the nucleotide sequence set forth in SEQ ID NOs: 1, 2, 3, 4, 5, 6, 7, 8, 9 or 45 to a heterologous nucleic acid fragment. Any heterologous nucleic acid fragment can be used to practice the invention. The selection will depend upon the desired application or phenotype to be achieved. The various nucleic acid sequences can be manipulated so as to provide for the nucleic acid sequences in the proper orientation. It is believed that various combinations of promoter elements as described herein may be useful in practicing the present invention.

In another aspect, this invention concerns a recombinant DNA construct comprising at least one acetolactate synthase (ALS) nucleic acid fragment operably linked to HRP1 promoter, or combination of promoter elements, of the present invention. The acetolactate synthase gene is involved in the biosynthesis of branched chain amino acids in plants and is the site of action of several herbicides including sulfonyl urea. Expression of a mutated acetolactate synthase gene encoding a protein that can no longer bind the herbicide will enable the transgenic plants to be resistant to the herbicide (U.S. Pat. Nos. 5,605,011, 5,378,824). The mutated acetolactate synthase gene is also widely used in plant transformation to select transgenic plants.

In another embodiment, this invention concerns host cells comprising either the recombinant DNA constructs of the invention as described herein or isolated polynucleotides of the disclosure as described herein. Examples of host cells which can be used to practice the invention include, but are not limited to, yeast, bacteria, and plants.

Plasmid vectors comprising the instant recombinant expression construct can be constructed. The choice of plasmid vector is dependent upon the method that will be used to transform host cells. The skilled artisan is well aware of the genetic elements that must be present on the plasmid vector in order to successfully transform, select and propagate host cells containing the chimeric gene.

Methods for transforming dicots, primarily by use of Agrobacterium tumefaciens, and obtaining transgenic plants have been published, among others, for cotton (U.S. Pat. Nos. 5,004,863, 5,159,135); soybean (U.S. Pat. Nos. 5,569,834, 5,416,011); Brassica (U.S. Pat. No. 5,463,174); peanut (Cheng et al., Plant Cell Rep. 15:653-657 (1996), McKently et al., Plant Cell Rep. 14:699-703 (1995)); papaya (Ling et al., Bio/technology 9:752-758 (1991)); and pea (Grant et al., Plant Cell Rep. 15:254-258 (1995)). For a review of other commonly used methods of plant transformation see Newell, C. A., Mol. Biotechnol. 16:53-65 (2000). One of these methods of transformation uses Agrobacterium rhizogenes (Tepfler, M. and Casse-Delbart, F., Microbiol. Sci. 4:24-28 (1987)). Transformation of soybeans using direct delivery of DNA has been published using PEG fusion (PCT Publication No. WO 92/17598), electroporation (Chowrira et al., Mol. Biotechnol. 3:17-23 (1995); Christou et al., Proc. Natl. Acad. Sci. U.S.A. 84:3962-3966 (1987)), microinjection, or particle bombardment (McCabe et al., Biotechnology 6:923-926 (1988); Christou et al., Plant Physiol. 87:671-674 (1988)).

There are a variety of methods for the regeneration of plants from plant tissues. The particular method of regeneration will depend on the starting plant tissue and the particular plant species to be regenerated. The regeneration, development and cultivation of plants from single plant protoplast transformants or from various transformed explants is well known in the art (Weissbach and Weissbach, Eds.; In Methods for Plant Molecular Biology; Academic Press, Inc.: San Diego, Calif., 1988). This regeneration and growth process typically includes the steps of selection of transformed cells, culturing those individualized cells through the usual stages of embryonic development or through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant DNA fragments and recombinant expression constructs and the screening and isolating of clones, (see for example, Sambrook, J. et al., In Molecular Cloning: A Laboratory Manual; $2^{nd}$ ed.; Cold Spring Harbor Laboratory Press: Cold Spring Harbor, N. Y., 1989; Maliga et al., In Methods in Plant Molecular Biology; Cold Spring Harbor Press, 1995; Birren et al., In Genome Analysis: Detecting Genes, 1; Cold Spring Harbor: New York, 1998; Birren et al., In Genome Analysis: Analyzing DNA, 2; Cold Spring Harbor: New York, 1998; Clark, Ed., In Plant Molecular Biology: A Laboratory Manual; Springer: New York, 1997).

The skilled artisan will also recognize that different independent transformation events will result in different levels and patterns of expression of the chimeric genes (Jones et al., EMBO J. 4:2411-2418 (1985); De Almeida et al., Mol. Gen. Genetics 218:78-86 (1989)). Thus, multiple events must be screened in order to obtain lines displaying the desired expression level and pattern. Such screening may be accomplished by Northern analysis of mRNA expression, Western analysis of protein expression, or phenotypic analysis. Also of interest are seeds obtained from transformed plants displaying the desired gene expression profile.

Tissue-specific expression of chimeric genes in anther tapetum, ovule inner integument and nucellus, very young embryo, and seed coat makes the HRP1 promoter of the instant invention especially useful when such tissue-specific specific expression of a target heterologous nucleic acid fragment is required.

Another general application of the HRP1 promoter of the invention is to construct chimeric genes that can be used to reduce expression of at least one heterologous nucleic acid fragment in a plant cell. To accomplish this, a chimeric gene designed for gene silencing of a heterologous nucleic acid fragment can be constructed by linking the fragment to the HRP1 promoter of the present invention. (See U.S. Pat. No. 5,231,020, and PCT Publication No. WO 99/53050 published on Oct. 21, 1999, PCT Publication No. WO 02/00904 published on Jan. 3, 2002, and PCT Publication No. WO 98/36083 published on Aug. 20, 1998, for methodology to block plant gene expression via cosuppression.) Alternatively, a chimeric gene designed to express antisense RNA for a heterologous nucleic acid fragment can be constructed by linking the fragment in reverse orientation to the HRP1 promoter of the present invention. (See U.S. Pat. No. 5,107,065 for methodology to block plant gene expression via antisense RNA.) Either the cosuppression or antisense chimeric gene can be introduced into plants via transformation. Transformants wherein expression of the heterologous nucleic acid fragment is decreased or eliminated are then selected.

This invention also concerns a method of altering (increasing or decreasing) the expression of at least one heterologous nucleic acid fragment in a plant cell which comprises:
  (a) transforming a plant cell with the recombinant expression construct described herein;
  (b) growing fertile mature plants from the transformed plant cell of step (a);
  (c) selecting plants containing a transformed plant cell wherein the expression of the heterologous nucleic acid fragment is increased or decreased.

Transformation and selection can be accomplished using methods well-known to those skilled in the art including, but not limited to, the methods described herein.

Non-limiting examples of methods and compositions disclosed herein are as follows:
1. A recombinant DNA construct comprising:
  (a) a nucleotide sequence comprising any of the sequences set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO: 45; or,
  (b) a full-length complement of (a); or,
  (c) a nucleotide sequence comprising a sequence having at least 72% sequence identity, based on the Clustal V method of alignment with pairwise alignment default parameters (KTUPLE=2, GAP PENALTY=5, WINDOW=4 and DIAGONALS SAVED=4), when compared to the nucleotide sequence of (a);
  operably linked to at least one heterologous sequence, wherein said nucleotide sequence is a promoter.
2. The recombinant DNA construct of embodiment 1, wherein the promoter is a tissue-specific promoter.
3. The recombinant DNA construct of embodiment 1, wherein the nucleotide sequence of (c) has at least 95% identity, based on the Clustal V method of alignment with pairwise alignment default parameters (KTUPLE=2, GAP PENALTY=5, WINDOW=4 and DIAGONALS SAVED=4), when compared to the sequence set forth in SEQ ID NO:1.
4. The recombinant DNA construct of embodiment 1, wherein the nucleotide sequence is SEQ ID NO: 45.
5. A recombinant DNA construct comprising a promoter region of the HRP1 *Glycine max* gene as set forth in SEQ ID NO:1, wherein said promoter region comprises a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 11311, 1132, 1133, 1134, 1135, 1136, 1137, 1138, 1139, 1140, 1141, 1142, 1143, 1144, 1145, 1146, 1147, 1148, 1149, 1150, 11511, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, or 1208 consecutive nucleotides, wherein the first nucleotide deleted is the cytosine nucleotide ['C'] at position 1 of SEQ ID NO:1, operably linked to at least one heterologous sequence.

6. A vector comprising the recombinant DNA construct of embodiment 1.

7. A cell comprising the recombinant DNA construct of embodiment 1.

8. The cell of embodiment 7, wherein the cell is a plant cell.

9. A transgenic plant having stably incorporated into its genome the recombinant DNA construct of embodiment 1.

10. The transgenic plant of embodiment 9 wherein said plant is a dicot plant.

11. The transgenic plant of embodiment 10 wherein the plant is soybean.

12. A transgenic seed produced by the transgenic plant of embodiment 9 wherein the transgenic seed comprises the recombinant DNA construct of embodiment 1.

13. The recombinant DNA construct according to embodiment 1, wherein the at least one heterologous nucleotide sequence codes for a gene selected from the group consisting of: a reporter gene, a selection marker, a disease resistance conferring gene, a herbicide resistance conferring gene, an insect resistance conferring gene; a gene involved in carbohydrate metabolism, a gene involved in fatty acid metabolism, a gene involved in amino acid metabolism, a gene involved in plant development, a gene involved in plant growth regulation, a gene involved in yield improvement, a gene involved in drought resistance, a gene involved in cold resistance, a gene involved in heat resistance and a gene involved in salt resistance in plants.

14. The recombinant DNA construct according to embodiment 1, wherein the at least one heterologous nucleotide sequence encodes a protein selected from the group consisting of: a reporter protein, a selection marker, a protein conferring disease resistance, protein conferring herbicide resistance, protein conferring insect resistance; protein involved in carbohydrate metabolism, protein involved in fatty acid metabolism, protein involved in amino acid metabolism, protein involved in plant development, protein involved in plant growth regulation, protein involved in yield improvement, protein involved in drought resistance, protein involved in cold resistance, protein involved in heat resistance and protein involved in salt resistance in plants.

15. A method of expressing a coding sequence or a functional RNA in a plant comprising:
  a) introducing the recombinant DNA construct of embodiment 6 into the plant, wherein the at least one heterologous nucleotide sequence comprises a coding sequence or encodes a functional RNA;
  b) growing the plant of step a); and
  c) selecting a plant displaying expression of the coding sequence or the functional RNA of the recombinant DNA construct.

16. A method of transgenically altering a marketable plant trait, comprising:
  a) introducing a recombinant DNA construct of embodiment 1 into the plant;
  b) growing a fertile, mature plant resulting from step a); and
  c) selecting a plant expressing the at least one heterologous nucleotide sequence in at least one plant tissue based on the altered marketable trait.

17. The method of embodiment 16 wherein the marketable trait is selected from the group consisting of: disease resistance, herbicide resistance, insect resistance carbohydrate metabolism, fatty acid metabolism, amino acid metabolism, plant development, plant growth regulation, yield improvement, drought resistance, cold resistance, heat resistance, and salt resistance.

18. A method for altering expression of at least one heterologous nucleic acid fragment in plant comprising:
    (a) transforming a plant cell with the recombinant DNA construct of embodiment 1;
    (b) growing fertile mature plants from transformed plant cell of step (a); and
    (c) selecting plants containing the transformed plant cell wherein the expression of the heterologous nucleic acid fragment is increased or decreased.

19. The method of Embodiment 18 wherein the plant is a soybean plant.

20. A method for expressing a green fluorescent protein ZS-GREEN1 in a host cell comprising:
    (a) transforming a host cell with the recombinant DNA construct of embodiment 1; and,
    (b) growing the transformed host cell under conditions that are suitable for expression of the recombinant DNA construct, wherein expression of the recombinant DNA construct results in production of increased levels of ZS-GREEN1 protein in the transformed host cell when compared to a corresponding non-transformed host cell.

22. A plant stably transformed with a recombinant DNA construct comprising a soybean tissue-specific promoter and a heterologous nucleic acid fragment operably linked to said tissue-specific promoter, wherein said tissue-specific promoter is a capable of controlling expression of said heterologous nucleic acid fragment in a plant cell, and further wherein said tissue-specific promoter comprises any of the sequences set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO: 45.

EXAMPLES

The present invention is further defined in the following Examples, in which parts and percentages are by weight and degrees are Celsius, unless otherwise stated. Sequences of promoters, cDNA, adaptors, and primers listed in this invention all are in the 5' to 3' orientation unless described otherwise. Techniques in molecular biology were typically performed as described in Ausubel, F. M. et al., In Current Protocols in Molecular Biology; John Wiley and Sons: New York, 1990 or Sambrook, J. et al., In Molecular Cloning: A Laboratory Manual; $2^{nd}$ ed.; Cold Spring Harbor Laboratory Press: Cold Spring Harbor, N. Y., 1989 (hereinafter "Sambrook et al., 1989"). It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Identification of Soybean Tissue-specific Promoter Candidate Genes

Soybean expression sequence tags (EST) were generated by sequencing randomly selected clones from cDNA libraries constructed from different soybean tissues. Multiple EST sequences could often be found with different lengths representing the different regions of the same soybean gene. If more EST sequences representing the same gene are frequently found from a tissue-specific cDNA library such as a flower library than from a leaf library, there is a possibility that the represented gene could be a flower preferred gene candidate. Likewise, if similar numbers of ESTs for the same gene were found in various libraries constructed from different tissues, the represented gene could be a constitutively expressed gene. Multiple EST sequences representing the same soybean gene were compiled electronically based on their overlapping sequence homology into a unique full length sequence representing the gene. These assembled unique gene sequences were accumulatively collected in Pioneer Hi-Bred Intl proprietary searchable databases.

To identify Tissue-specific promoter candidate genes, searches were performed to look for gene sequences that were found exclusively or at much higher frequencies in a tissue of interest than in other tissues. For example, a gene frequently found in flower but not in other tissues such as leaf, root, embryo, pod, may be flower promoter candidate. One unique gene PSO401672 (also known as PSO38230 in an earlier version database of assembled unique gene sequences) was identified in the search to be a moderate early developing seed-specific promoter gene candidate. PSO401672 cDNA sequence (SEQ ID NO:20) as well as its putative translated protein sequence (SEQ ID NO:21) were used to search National Center for Biotechnology Information (NCBI) databases. Both PSO401672 nucleotide and amino acid sequences were found to have high homology to a soybean hypersensitive-induced response protein 1-like (NCBI accession XM_003519030.1).

Solexa digital gene expression dual-tag-based mRNA profiling using the Illumina (Genome Analyzer) GA2 machine is a restriction enzyme site anchored tag-based technology, in this regard similar to Mass Parallel Signature Sequence transcript profiling technique (MPSS), but with two key differences (Morrissy et al., Genome Res. 19:1825-1835 (2009); Brenner et al., Proc. Natl. Acad. Sci. USA 97:1665-70 (2000)). Firstly, not one but two restriction enzymes were used, DpnII and NlaI, the combination of which increases gene representation and helps moderate expression variances. The aggregate occurrences of all the resulting sequence reads emanating from these DpnII and NlaI sites, with some repetitive tags removed computationally were used to determine the overall gene expression levels. Secondly, the tag read length used here is 21 nucleotides, giving the Solexa tag data higher gene match fidelity than the shorter 17-mers used in MPSS. Soybean mRNA global gene expression profiles are stored in a Pioneer proprietary database TDExpress (Tissue Development Expression Browser). Candidate genes with different expression patterns can be searched, retrieved, and further evaluated.

The hypersensitive-induced response protein gene PSO401672 (HRP1) corresponds to predicted gene Glyma02g02550.1 in the soybean genome, sequenced by the DOE-JGI Community Sequencing Program consortium (Schmutz J, et al., Nature 463:178-183 (2010)). The HRP1 expression profiles in twenty one tissues were retrieved from the TDExpress database using the gene ID Glyma02g02550.1 and presented as parts per ten millions (PPTM) averages of three experimental repeats (FIG. 1). The HRP1 gene is expressed the highest in young developing seeds and several folds lower in older developing seeds, flowers, young and medium pods. No HRP1 expression is detected in root, leaf, stem, or somatic embryos. HRP1 was thus selected as a young developing seed-specific candidate gene from which to clone a moderate early embryo-specific promoter.

Example 2

Isolation of Soybean HRP1 Promoter

The PSO401672 cDNA sequence was BLAST searched against the soybean genome sequence database sequence (Schmutz J, et al., Nature 463:178-183 (2010)) to identify corresponding genomic DNA. The ~1.5 kb sequence upstream of the PSO401672 start codon ATG was selected as HRP1 promoter to be amplified by PCR (polymerase chain reaction). The primers shown in SEQ ID NO:10 and 11 were then designed to amplify by PCR the putative full length 1584 bp HRP1 promoter from soybean genomic DNA (SEQ ID NO:1). SEQ ID NO:9 contains a recognition site for the restriction enzyme XmaI. SEQ ID NO:11 contains a recognition site for the restriction enzyme NcoI. The 2 bp "AG" proceeding the ATG start codon of PSO401672 cDNA (SEQ ID NO:20) were removed by the PCR cloining. The XmaI and NcoI sites were included for subsequent cloning.

PCR cycle conditions were 94° C. for 4 minutes; 35 cycles of 94° C. for 30 seconds, 60° C. for 1 minute, and 68° C. for 2 minutes; and a final 68° C. for 5 minutes before holding at 4° C. using the Platinum high fidelity Taq DNA polymerase (Invitrogen). The PCR reaction was resolved using agarose gel electrophoresis to identify the right size PCR product representing the ~1.6 Kb HRP1 promoter. The PCR fragment was first cloned into pCR2.1-TOPO vector by TA cloning (Invitrogen). Several clones containing the ~1.6 Kb DNA insert were sequenced and only one clone with the correct HRP1 promoter sequence was selected for further cloning. The plasmid DNA of the selected clone was digested with XmaI and NcoI restriction enzymes to move the HRP1 promoter upstream of the ZS-GREEN1 (GFP) fluorescent reporter gene in QC641 (FIG. 3A, SEQ ID NO:19). Construct QC641 contains the recombination sites AttL1 and AttL2 (SEQ ID NO:36 and 37) to qualify as a GATEWAY® cloning entry vector (Invitrogen). The 1584 bp sequence upstream of the HRP1 gene PSO401672 start codon ATG including the XmaI and NcoI sites is herein designated as soybean HRP1 promoter GM-HRP1 PRO of SEQ ID NO:1.

Comparison of PSO401672 cDNA sequence SEQ ID NO:20 to soybean genome sequences revealed that SEQ ID NO:20 comprised a 5' untranslated region (5' UTR) of at least 47 base pairs (SEQ ID NO:44) and a 220 bp intron dividing the 5'UTR region into two segments in corresponding genomic DNA sequence (SEQ ID NO:45). The first 45 bp of the 47 bp 5' UTR and the 5' UTR 220 bp intron are included in HRP1 promoter at its 3' end (SEQ ID NO:1). It is known to one of skilled in the art that a 5' UTR region can be altered (deletion or substitutions of bases) or replaced by an alternative 5' UTR while maintaining promoter activity.

Example 3

HRP1 Promoter Copy Number Analysis

Southern hybridization analysis was performed to examine whether additional copies or sequences with significant similarity to the HRP1 promoter exist in the soybean genome. Soybean 'Jack' wild type genomic DNA was digested with nine different restriction enzymes, BamHI, BgIII, DraI, EcoRI, EcoRV, HindIII, MfeI, NdeI, and SpeI and distributed in a 0.7% agarose gel by electrophoresis. The DNA was blotted onto Nylon membrane and hybridized at 60° C. with digoxigenin labeled HRP1 promoter DNA probe in Easy-Hyb Southern hybridization solution, and then sequentially washed 10 minutes with 2×SSC/0.1% SDS at room temperature and 3×10 minutes at 65° C. with 0.1× SSC/0.1% SDS according to the protocol provided by the manufacturer (Roche Applied Science, Indianapolis, Ind.). The HRP1 promoter probe was labeled by PCR using the DIG DNA labeling kit (Roche Applied Science) with primers HRP1-S5 (SEQ ID NO:16) and PSO382305Nco (SEQ ID NO:11) and QC641 plasmid DNA (SEQ ID NO:22) as the template to make a 606 bp long probe covering the 3' half of the HRP1 promoter (FIG. 2B).

Two of the nine restriction enzymes MfeI and DraI would cut the 606 bp HRP1 promoter probe region each once at the 3' end resulting 54 bp and 43 bp 3' portion of the HRP1 probe, respectively, which might be too short to hybridize stably to the genomic target sequence. A single HRP1 promoter fragment corresponding to the 5' portions of the 606 bp HRIP1 probe upstream of the MfeI or DraI restriction sites would be readily detected by Southern hybridization (FIG. 2B). Since DraI would also cut the HRPI promoter shortly upstream of the HRP1 probe region, a 720 bp DraI band was expected. None of the other seven restriction enzymes BamHI, BgIII, EcoRI, EcoRV, HindIII, NdeI, and SpeI would cut the HRP1 promoter probe region. Therefore, only one band would be expected to be hybridized for each of the nine digestions if only one copy of HRP1 promoter sequence exists in soybean genome (FIG. 2B). The observation that only one band was detected in each digestion with the nine enzymes suggested that there is only one copy of the HRP1 promoter sequence in soybean genome (FIG. 2A). The DIGVII molecular markers used on the Southern blot are 8576, 7427, 6106, 4899, 3639, 2799, 1953, 1882, 1515, 1482, 1164, 992, 718 and 710 bp.

Since the whole soybean genome sequence is now publically available (Schmutz J, et al., Nature 463:178-183 (2010)), the HRP1 promoter copy numbers can also be evaluated by searching the soybean genome with the 1584 bp promoter sequence (SEQ ID NO:1). Consistent with above Southern analysis, only one sequence Gm02: 1884489-1882931 matching the HRP1 promoter sequence 1-1584 bp in complementary orientation with some mismatches and small deletions in the middle was identified (FIG. 8). The mismatches and small deletions are probably due to the difference between the cultivars Williams 82 used in the soybean genome sequence project and Jack used in the HRP1 promoter cloning. The 5' end 6 bp and 3' end 6 bp of the 1584 bp HRP1 promoter may not match the genomic Gm02 sequence since they are artificially added XmaI and NcoI sites. No other sequences with significant homology to the HRP1 promoter sequence was found in soybean genome.

FIG. 8 shows a nucleotide sequence alignment of SEQ ID NO: 1, comprising the full length HRP1 promoter of the disclosure, and SEQ ID NO: 45, comprising a 1559bp native soybean genomic DNA from Gm02:1884489-1882931 (Schmutz J. et al., Nature 463:178-183, 2010). As shown in the figure, the HRP1 promoter of SEQ ID NO:1 is 97.9% identical to SEQ ID NO: 45, based on the Clustal Vmethod of alignment with pairwise alignment default parameters (KTUPLE=2, GAP PENALTY=5, WINDOW=4 and DIAGONALS SAVED=4). Based on the data described in Examples 1- 7, it is believed that SEQ ID NO: 45 has promoter activity.

Example 4

HRP1:GFP Reporter Gene Constructs and Soybean Transformation

The HRP1:GFP cassette was moved from DNA construct QC641 (SEQ ID NO:22) into a GATEWAY® destination vector QC478i (SEQ ID NO:23) by LR Clonase® (Invitrogen) mediated DNA recombination between the attL1 and attL2 recombination sites (SEQ ID NO:36, and 37, respectively) in QC641 and the attR1-attR2 recombination sites (SEQ ID NO:38, and 39, respectively) in QC478i to make the final transformation construct QC650 (SEQ ID NO:24; FIG. 3B).

Since the GATEWAY® destination vector QC478i already contains a soybean transformation selectable marker gene SAMS:HRA, the resulting DNA construct QC650 has the HRP1:GFP gene expression cassette linked to the SAMS:HRA cassette (FIG. 3B). Two 21 bp recombination sites attB1 and attB2 (SEQ ID NO:40, and 41, respectively) were newly created recombination sites resulting from DNA recombination between attL1 and attR1, and between attL2 and attR2, respectively. The 7012 bp DNA fragment containing the linked HRP1:GFP and SAMS:HRA expression cassettes was isolated from plasmid QC650 (SEQ ID NO:24) with AscI digestion, separated from the vector backbone fragment by agarose gel electrophoresis, and purified from the gel with a DNA gel extraction kit (QIAGEN®, Valencia, Calif.). The purified DNA fragment was transformed to soybean cultivar Jack by the method of particle gun bombardment (Klein et al., Nature 327:70-73 (1987); U.S. Pat. No. 4,945,050) as described in detail below to study the HRP1 promoter activity in stably transformed soybean plants.

The same methodology as outlined above for the HRP1:GFP expression cassette construction and transformation can be used with other heterologous nucleic acid sequences encoding for example a reporter protein, a selection marker, a protein conferring disease resistance, protein conferring herbicide resistance, protein conferring insect resistance; protein involved in carbohydrate metabolism, protein involved in fatty acid metabolism, protein involved in amino acid metabolism, protein involved in plant development, protein involved in plant growth regulation, protein involved in yield improvement, protein involved in drought resistance, protein involved in cold resistance, protein involved in heat resistance and salt resistance in plants.

Soybean somatic embryos from the Jack cultivar were induced as follows. Cotyledons (~3 mm in length) were dissected from surface sterilized, immature seeds and were cultured for 6-10 weeks in the light at 26° C. on a Murashige and Skoog (MS) media containing 0.7% agar and supplemented with 10 mg/ml 2,4-D (2,4-Dichlorophenoxyacetic acid). Globular stage somatic embryos, which produced secondary embryos, were then excised and placed into flasks containing liquid MS medium supplemented with 2,4-D (10 mg/ml) and cultured in the light on a rotary shaker. After repeated selection for clusters of somatic embryos that multiplied as early, globular staged embryos, the soybean embryogenic suspension cultures were maintained in 35 ml liquid media on a rotary shaker, 150 rpm, at 26° C. with fluorescent lights on a 16:8 hour day/night schedule. Cultures were subcultured every two weeks by inoculating approximately 35 mg of tissue into 35 ml of the same fresh liquid MS medium.

Soybean embryogenic suspension cultures were then transformed by the method of particle gun bombardment using a DuPont Biolistic™ PDS1000/HE instrument (Bio-Rad Laboratories, Hercules, Calif.). To 50 μl of a 60 mg/ml 1.0 mm gold particle suspension were added (in order): 30 μl of 30 ng/μl QC589 DNA fragment HRP1:GFP+SAMS:HRA, 20 μl of 0.1 M spermidine, and 25 μl of 5 M $CaCl_2$. The particle preparation was then agitated for 3 minutes, spun in a centrifuge for 10 seconds and the supernatant removed. The DNA-coated particles were then washed once in 400 μl 100% ethanol and resuspended in 45 μl of 100% ethanol. The DNA/particle suspension was sonicated three times for one second each. Then 5 μl of the DNA-coated gold particles was loaded on each macro carrier disk.

Approximately 300-400 mg of a two-week-old suspension culture was placed in an empty 60×15 mm Petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded once. Following bombardment, the tissue was divided in half and placed back into liquid media and cultured as described above.

Five to seven days post bombardment, the liquid media was exchanged with fresh media containing 100 ng/ml chlorsulfuron as selection agent. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each clonally propagated culture was treated as an independent transformation event and subcultured in the same liquid MS media supplemented with 2,4-D (10 mg/ml) and 100 ng/ml chlorsulfuron selection agent to increase mass. The embryogenic suspension cultures were then transferred to agar solid MS media plates without 2,4-D supplement to allow somatic embryos to develop. A sample of each event was collected at this stage for quantitative PCR analysis.

Cotyledon stage somatic embryos were dried-down (by transferring them into an empty small Petri dish that was seated on top of a 10 cm Petri dish containing some agar gel to allow slow dry down) to mimic the last stages of soybean seed development. Dried-down embryos were placed on germination solid media and transgenic soybean plantlets were regenerated. The transgenic plants were then transferred to soil and maintained in growth chambers for seed production.

Genomic DNA were extracted from somatic embryo samples and analyzed by quantitative PCR using a 7500 real time PCR system (Applied Biosystems, Foster City, Calif.) with gene-specific primers and FAM-labeled fluorescence probes to check copy numbers of both the SAMS:HRA expression cassette and the HRP1:GFP expression cassette. The qPCR analysis was done in duplex reactions with a heat shock protein (HSP) gene as the endogenous controls and a transgenic DNA sample with a known single copy of SAMS: HRA or GFP transgene as the calibrator. The endogenous control HSP probe was labeled with VIC and the target gene SAMS:HRA or GFP probe was labeled with FAM for the simultaneous detection of both fluorescent probes (Applied Biosystems). PCR reaction data were captured and analyzed using the sequence detection software provided with the 7500 real time PCR system and the gene copy numbers were calculated using the relative quantification methodology (Applied Biosystems).

The primers and probes used in the qPCR analysis are listed below.
SAMS forward primer: SEQ ID NO:27
FAM labeled ALS probe: SEQ ID NO:28
ALS reverse primer: SEQ ID NO:29
GFP forward primer: SEQ ID NO:30
FAM labeled GFP probe: SEQ ID NO:31
GFP reverse primer: SEQ ID NO:32
HSP forward primer: SEQ ID NO:33
VIC labeled HSP probe: SEQ ID NO:34
HSP reverse primer: SEQ ID NO:35

Only transgenic soybean events containing 1 or 2 copies of both the SAMS:HRA expression cassette and the HRP1: GFP expression cassette were selected for further gene expression evaluation and seed production (see Table 1). Events negative for GFP qPCR or with more than 2 copies for the SAMS:HRA qPCR were not further followed. GFP expressions were not detected on somatic embryos and are described in detail in EXAMPLE 7.

TABLE 1

Relative transgene copy numbers and GFP expression of HRP1:GFP transgenic plants

| Event ID | GFP expression | GFP qPCR | SAMS:HRA qPCR |
|---|---|---|---|
| 9493.4.1 | – | 1.4 | 1.3 |
| 9493.7.1 | – | 2.5 | 1.2 |
| 9493.7.4 | +/– | 3.2 | 0.6 |
| 9493.7.5 | – | 1.9 | 1.1 |
| 9493.7.6 | – | 1.1 | 0.5 |
| 9493.7.7 | – | 0.9 | 0.4 |
| 9493.7.10 | – | 0.8 | 1.3 |
| 9493.7.12 | – | 1.6 | 1.4 |
| 9493.7.16 | – | 0.9 | 0.6 |
| 9493.8.1 | – | 2.9 | 1.4 |
| 9493.8.6 | – | 1.0 | 0.6 |
| 9493.8.7 | – | 1.6 | 1.2 |
| 9493.8.8 | – | 0.7 | 0.7 |
| 9493.9.3 | – | 0.7 | 0.7 |
| 9493.9.5 | – | 0.9 | 0.7 |
| 9493.9.6 | – | 1.0 | 1.1 |
| 9493.9.8 | – | 0.9 | 0.5 |
| 9493.9.11 | – | 1.5 | 0.6 |
| 9493.9.12 | – | 1.5 | 1.1 |
| 9493.9.13 | – | 1.6 | 1.1 |

Example 5

Construction of HRP1 Promoter Deletion Constructs

To define the transcriptional elements controlling the HRP1 promoter activity, seven 5' unidirectional deletion fragments 1334 bp, 1149 bp, 930 bp, 721 bp, 606 bp, 487 bp, and 376 bp in length corresponding to SEQ ID NO:2, 3, 4, 5, 6, 7, and 8, respectively, were made by PCR amplification from the full length soybean HRP1 promoter contained in the original construct QC641 (FIG. 3A). The 3' end restriction site NcoI sequence CCATGG is counted in the promoter lengths. The same antisense primer PSO382305Nco (SEQ ID NO:11) was used in the amplification by PCR of all the seven HRP1 promoter fragments (SEQ ID NOs: 2, 3, 4, 5, 6, 7, and 8) by pairing with different sense primers SEQ ID NOs:12, 13, 14, 15, 16, 17, and 18, respectively. Another 1359 bp fragment (SEQ ID NO:9) with the 220 bp 5' UTR intron removed was similarly made using primers PSO382305Xma and HRP1 Nco (SEQ ID NO:10, 19). Each of the PCR amplified promoter DNA fragments was cloned back into the GATEWAY® cloning ready vector QC641 at XmaI and NcoI sites to replace the full length HRP1 promoter and confirmed by sequencing. The map of construct QC641-1 (SEQ ID NO:25) containing the 1334 bp HRP1 promoter fragment (SEQ ID NO:2) is shown in FIG. 4A. The maps of constructs QC641-2, 3, 4, 5, 6, 7, and 8 containing the truncated HRP1 promoter fragments SEQ ID NOs: 3, 4, 5, 6, 7, 8, and 9 are similar to QC641-1 map and are not showed. Each HRP1:GFP cassette was subsequently cloned into a GATEWAY® destination vector QC478i (SEQ ID NO:23) by GATEWAY® LR Clonase® reaction (Invitrogen) upstream of the SAMS:HRA cassette (see the example map QC641-1G in FIG. 4B and SEQ ID NO:26). A 21 bp GATEWAY® recombination site attB1 (SEQ ID NO:40) was left between the HRP1:GFP reporter gene cassette and the SAMS:HRA selectable marker gene cassette as a result of the GATEWAY® cloning process. The maps and sequences of constructs QC641-2G, 3G, 4G, 5G, 6G, 7G, and 8G containing the HRP1 promoter fragments SEQ ID NOs:3, 4, 5, 6, 7, 8, and 9 are similar to QC641-1G map and are not showed.

The HRP1:GFP promoter deletion constructs were delivered into germinating soybean cotyledons by gene gun bombardment for transient gene expression study. A similar construct QC732 with a soybean constitutive promoter GM-EF1A PRO (U.S. Patent Application No. 20080313776) driving GFP expression was used as positive control (FIG. 4C). The eight HRP1 promoter fragments analyzed are schematically described in FIG. 5 with the 5' UTR and 5' UTR intron depicted.

Example 6

Transient Expression Analysis of HRP1:GFP Constructs

The constructs containing the full length and truncated HRP1 promoter fragments QC641, QC641-1G, 2G, 3G, 4G, 5G, 6G, 7G, and 8G were tested by transiently expressing the ZS-GREEN1 (GFP) reporter gene in germinating soybean cotyledons. Soybean seeds were rinsed with 10% TWEEN® 20 in sterile water, surface sterilized with 70% ethanol for 2 minutes and then by 6% sodium hypochloride for 15 minutes. After rinsing the seeds were placed on wet filter paper in Petri dish to germinate for 4-6 days under light at 26° C. Green cotyledons were excised and placed inner side up on a 0.7% agar plate containing Murashige and Skoog media for particle gun bombardment. The DNA and gold particle mixtures were prepared similarly as described in EXAMPLE 4 except with more DNA (100 ng/µl). The bombardments were also carried out under similar parameters as described in EXAMPLE 4. GFP expression was checked under a Leica MZFLIII stereo microscope equipped with UV light source and appropriate light filters (Leica Microsystems Inc., Bannockburn, Ill.) and pictures were taken approximately 24 hours after bombardment with 8× magnification using a Leica DFC500 camera with settings as 0.60 gamma, 1.0 gain, 0.70 saturation, 61 color hue, 56 color saturation, and 0.51 second exposure.

The full length HRP1 promoter construct QC641 had weaker fluorescence signals in transient expression assay compared to the positive control QC732 by showing fewer and smaller yellow dots in red background. Each dot represented a single cotyledon cell which appeared larger if the fluorescence signal was strong or smaller if the fluorescence signal was weak even under the same magnification (FIG. 6). Deletion constructs QC641-1G and 2G had some more yellow dots while the other deletion constructs QC641-3G, 4G, 5G, 6G, 7G had similar yellow dots as the full length promoter construct QC641 (FIG. 6), indicating that these promoter fragments including the shortest 376 bp HRP1 promoter in QC641-7G are all similarly functional. Deletion of the 220 bp 5' UTR intron did not significantly change the promoter function as indicated by the similar yellow dots in the intron-less promoter construct QC641-8G.

The data clearly indicate that all deletion constructs are functional as a promoter and as such SEQ ID NOs: 2, 3, 4, 5, 6, 7, 8, 9 are all functional fragments of SEQ ID NO:1.

Example 7

HRP1:GFP Expression in Stable Transgenic Soybean Plants

The stable expression of the fluorescent protein reporter gene ZS-GREEN1 (GFP) driven by the full length HRP1 promoter (SEQ ID NO:1) in transgenic soybean plants is shown in FIG. 7A-P.

ZS-GREEN1 (GFP) gene expression was tested at different stages of transgenic plant development for yellow fluorescence emission under a Leica MZFLIII stereo microscope equipped with appropriate fluorescent light filters. Green fluorescence was detected in embryogenic callus during the suspension culture period of soybean transformation (FIG. 7A). The negative section of a positive embryo cluster emitted weak red color due to auto fluorescence from the chlorophyll contained in soybean green tissues including embryos. The reddish green fluorescence indicated that the GFP expression was moderate since everything would be bright green if the GFP gene was driven by a strong promoter. Shortly afterwards, GFP expression was no longer detected in differentiating somatic embryos placed on solid medium and throughout all later stages of somatic embryo development (FIG. 7B).

Figure 7:
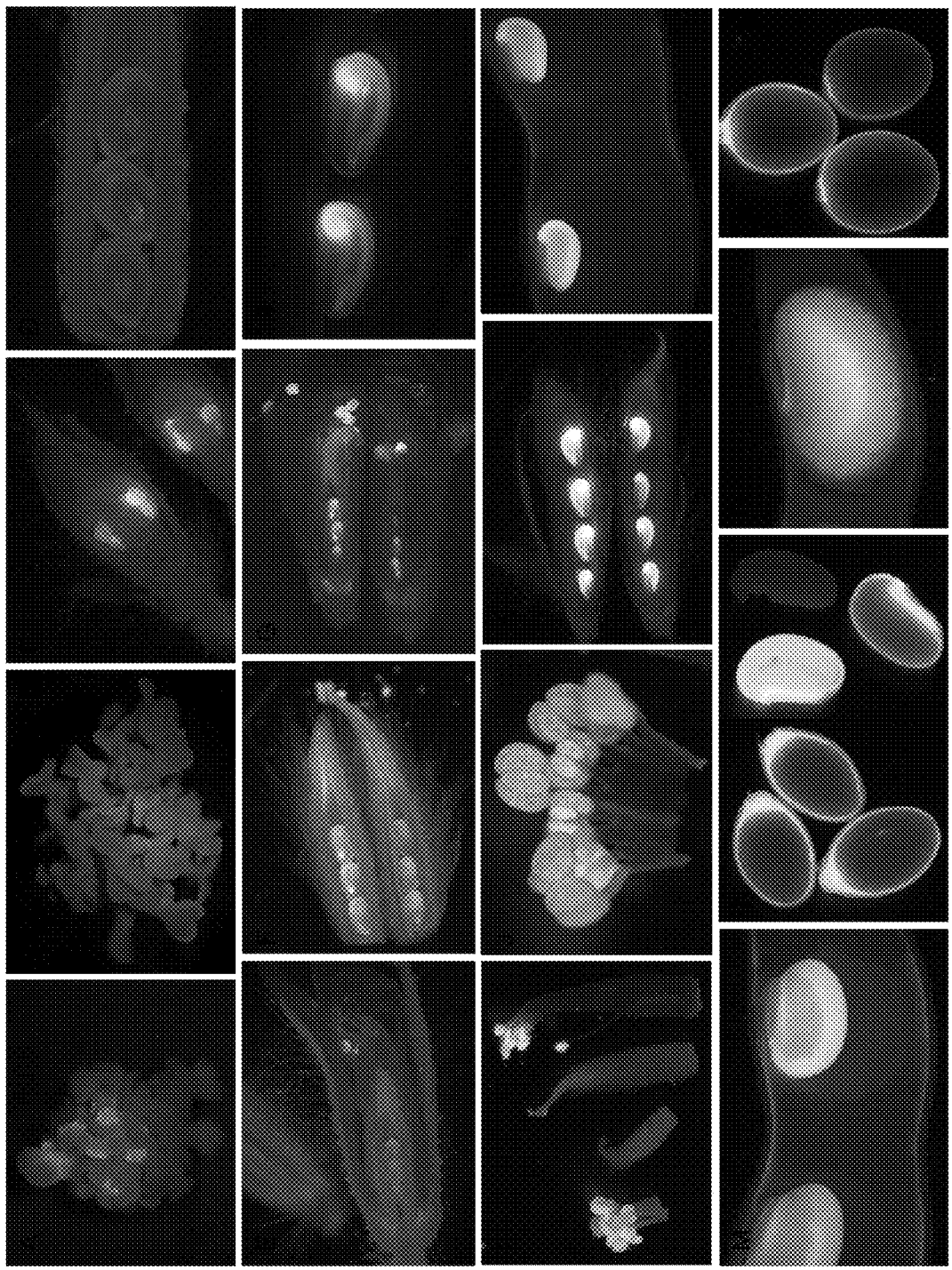

When transgenic plants regenerated, GFP expression was not detected in any vegetative tissues including leaf, leaf petiole, root, stem, etc., which are not shown. Negative controls for most tissue types displayed in FIG. 7 are also not shown though any green tissue such as leaf or stem negative for GFP expression would look red and any white tissue such as root and petal would look dull yellowish under the GFP fluorescent light filter. GFP expression was detected again when in flower buds when the transgenic plants went in reproduction stage.

A soybean flower consists of five sepals, five petals including one standard large upper petal, two large side petals, and two small lower petals called kneel to enclose ten stamens and one pistil. The pistil consists of a stigma, a style, and an ovary in which there are 2-4 ovules. A stamen consists of a filament, and an anther on its tip. The filaments of nine of the stamens are fused and elevated as a single structure with a posterior stamen remaining separate. Pollen grains reside inside anther chambers and are released during pollination the day before the fully opening of the flower. Fluorescence signals were detected specifically in anthers, part of style, and in the inside of ovules of both flower buds and open flowers. No fluorescence signals were detected in other parts of the flower such as sepals, petals, filament, or ovary wall (FIG. 7C-J). Fluorescing internal structures of flower bud ovules, open flower ovules, and flower bud anthers are obvious in close-up pictures (FIGS. 7D, H, and J).

Strong fluorescence signals were detected in young developing seeds and moderately in the lining of pod coats of the HRP1:GFP transgenic plants from young R3 pod of ~5 mm long, to full R4 pod of ~20 mm long (FIG. 7K-M). Fluorescence signals were concentrated in the micropylar end of developing seeds in very young pods that still have some wilting sepals and petals attached (FIGS. 7H, and K). The fluorescence signals were then distributed more evenly in older developing seeds (FIG. 7L-P). Indeed, the fluorescent signals were only detected in the seed coat of older seeds rather than in embryos when they were dissected (FIGS. 7N, and P). The seed and pod development stages were defined according to descriptions in Fehr and Caviness, IWSRBC 80:1-12 (1977).

In conclusion, HRP1:GFP expression was detected strongly but only in specific tissues during flower and seed development indicating that the soybean HRP1 promoter is a strong tissue-specific promoter with very unique expression patterns.

What is claimed is:

1. A recombinant DNA construct comprising:
   (a) a nucleotide sequence comprising any of the sequences set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO: 45; or,
   (b) a full-length complement of (a); or,
   (c) a nucleotide sequence comprising a sequence having at least 97% sequence identity, based on the Clustal V method of alignment with pairwise alignment default parameters (KTUPLE=2, GAP PENALTY=5, WINDOW=4 and DIAGONALS SAVED=4), when compared to the nucleotide sequence of (a);
   operably linked to at least one heterologous sequence, wherein said nucleotide sequence is a tissue-specific promoter.

2. A recombinant DNA construct comprising a fragment of SEQ ID NO:1 having at least 350 consecutive nucleotides of SEQ ID NO:1 wherein said fragment is a tissue-specific promoter and wherein said fragment is operably linked to at least one heterologous nucleotide sequence.

3. The recombinant DNA construct of claim 1, wherein the nucleotide sequence of (c) has at least 97% identity, based on the Clustal V method of alignment with pairwise alignment default parameters (KTUPLE=2, GAP PENALTY=5, WINDOW=4 and DIAGONALS SAVED=4), when compared to the sequence set forth in SEQ ID NO:1.

4. The recombinant DNA construct of claim 1, wherein the nucleotide sequence is SEQ ID NO: 45.

5. A recombinant DNA construct comprising a promoter region of the HRP1 *Glycine max* gene as set forth in SEQ ID NO:1, wherein said promoter region comprises a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 11511, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, or 1208 consecutive nucleotides, wherein the first nucleotide deleted is the cytosine nucleotide ['C'] at position 1 of SEQ ID NO:1, operably linked to at least one heterologous sequence.

6. A vector comprising the recombinant DNA construct of claim 1.

7. A cell comprising the recombinant DNA construct of claim 1.

8. The cell of claim 7, wherein the cell is a plant cell.

9. A transgenic plant having stably incorporated into its genome the recombinant DNA construct of claims 1 or 2.

10. The transgenic plant of claim 9 wherein said plant is a dicot plant.

11. The transgenic plant of claim 10 wherein the plant is soybean.

12. A transgenic seed produced by the transgenic plant of claim 9 wherein the transgenic seed comprises the recombinant DNA construct.

13. The recombinant DNA construct according to claim 1, wherein the at least one heterologous nucleotide sequence comprises a nucleotide sequence selected from the group consisting of: a reporter nucleotide sequence, a selection marker nucleotide sequence, a disease resistance conferring nucleotide sequence, a herbicide resistance conferring nucleotide sequence, an insect resistance conferring nucleotide sequence; a nucleotide sequence involved in carbohydrate metabolism, a nucleotide sequence involved in fatty acid metabolism, a nucleotide sequence involved in amino acid metabolism, a nucleotide sequence involved in plant development, a nucleotide sequence involved in plant growth regulation, a nucleotide sequence involved in yield improvement, a nucleotide sequence involved in drought resistance, a nucleotide sequence involved in cold resistance, a nucleotide sequence involved in heat resistance and a nucleotide sequence involved in salt resistance in plants.

14. The recombinant DNA construct according to claim 1, wherein the at least one heterologous nucleotide sequence encodes a protein selected from the group consisting of: a reporter protein, a selection marker, a protein conferring disease resistance, protein conferring herbicide resistance, protein conferring insect resistance; protein involved in carbohydrate metabolism, protein involved in fatty acid metabolism, protein involved in amino acid metabolism, protein involved in plant development, protein involved in plant growth regulation, protein involved in yield improvement, protein involved in drought resistance, protein involved in cold resistance, protein involved in heat resistance and protein involved in salt resistance in plants.

15. A method of expressing a coding sequence or a functional RNA in a plant comprising:
  a) introducing the recombinant DNA construct of claim 1 into at least one plant cell, wherein the at least one heterologous nucleotide sequence comprises a coding sequence or encodes a functional RNA;
  b) growing at least one plant from the at least one plant cell of step a); and,
  c) selecting a plant displaying expression of the coding sequence or the functional RNA of the recombinant DNA construct.

16. A method of transgenically altering a marketable plant trait, comprising:
  a) introducing the recombinant DNA construct of claim 1 into at least one plant cell;
  b) growing at least one fertile, mature plant from the at least one plant cell of step a); and,
  c) selecting a plant expressing the at least one heterologous nucleotide sequence in at least one plant tissue based on the altered trait.

17. The method of claim 16 wherein the trait is selected from the group consisting of: disease resistance, herbicide resistance, insect resistance carbohydrate metabolism, fatty acid metabolism, amino acid metabolism, plant development, plant growth regulation, yield improvement, drought resistance, cold resistance, heat resistance, and salt resistance.

18. A method for altering expression of at least one heterologous nucleic acid fragment in a plant comprising:
  (a) transforming at least one plant cell with the recombinant DNA construct of claim 1;
  (b) growing at least one fertile mature plant from transformed plant cell of step (a); and,
  (c) selecting a plant containing the transformed plant cell wherein the expression of the heterologous nucleic acid fragment is increased or decreased.

19. The method of claim 18 wherein the plant is a soybean plant.

20. A method for expressing a green fluorescent protein in a host cell comprising:
  (a) transforming a host cell with the recombinant DNA construct of claim 1; and,
  (b) growing the transformed host cell under conditions that are suitable for expression of the recombinant DNA construct, wherein expression of the recombinant DNA construct results in production of increased levels of green fluorescent protein in the transformed host cell when compared to a corresponding non-transformed host cell.

21. A plant stably transformed with a recombinant DNA construct comprising a soybean tissue-specific promoter and a heterologous nucleic acid fragment operably linked to said tissue-specific promoter, wherein said tissue-specific promoter is capable of controlling expression of said heterologous nucleic acid fragment in a plant cell, and further wherein said tissue-specific promoter comprises any of the sequences set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO: 45.

22. The recombinant DNA construct of claim 2 wherein the fragment is contained within a polynucleotide having at least 72% identify to SEQ ID NO: 1.

* * * * *

SEQUENCE LISTING

```
<160> NUMBER OF SEQ ID NOS: 45

<210> SEQ ID NO 1
<211> LENGTH: 1584
<212> TYPE: DNA
<213> ORGANISM: Glycine max

<400> SEQUENCE: 1
cccgggattg tttccatgaa tccttcaagt cgacgatttt tttattttt atttttatt      60 ttttatttt ggtataattc gacgaaactt gggttcatta tttgagtcca atgttcagtt    120
tacgcgctta aattagtact attctatctt aattacttt tcttatttct aacattgttg     180
```

| | |
|---|---:|
| aattagcttt cccaatcttc taaaaaaagc gtttccgtgt tatcagttga tgctgcaaaa | 240 |
| ggaaaccaga cgtttcctgt ttaggaaagt cgatccataa agttttcact ccattattta | 300 |
| atcagtttaa tgccgtttaa tattttgta ctgatgtaaa ataatttat attattattt | 360 |
| taaaagttaa taaatttgaa taattttta ctgtataatt ctttttctct tatataatta | 420 |
| gtcactgcac tagaatcaga acctaattca cttttggaaa cgattaccaa aataaataaa | 480 |
| taaccatgct gacgaaaaat ttaaaaatat tgatagtact gcttggttat tggcaaacta | 540 |
| agttttgata tgtactagca ggagccgaga tatttaattt atagcatttg gattaattag | 600 |
| ttttgtggta agaaataatc aattatttat ttatgatgga cataaaagaa taaatagttg | 660 |
| tttatacttt ttcacaattt tatcatattt ttattgagta gaattaatta ttttgtatta | 720 |
| ttcaaacacc ctattagtat tgaaaaaaat acttgaaagg gacgaattcg tcactgactt | 780 |
| gtggctcctt ggtcttaaag tgttggtaat gcgattttaa atatcaataa taattaaaat | 840 |
| gtgaaaagag aaaatatttt atactagtat gttaggtaaa atcttatcaa gctaatttaa | 900 |
| gatatacttt tatcttatct tgcatatgcg atgtacaaat taaagaacat tcaatatata | 960 |
| ttaattagaa aaaagttact gttaaaattt caaaggtagc gagaggaata atatggtatc | 1020 |
| acatggacaa tagttatggt gaagagagtg atagactgat ggatgggaca aagacaaaag | 1080 |
| cacttccaaa ataagagagt agttcaattc aacttaatta gtaagtaata tgcatattaa | 1140 |
| ggaagcattg caatttttgca aattaaaaca aacccatcac aattaatata gcatgactca | 1200 |
| cctaccatca ttatttgtga aactgattta tcattccttg gctcactctt tcctaattct | 1260 |
| aaagtactcc ctctctatat aaattctcac tcacccttagt tttcttctca tttcactcac | 1320 |
| ttgctttcaa attctcattt tcaaggtgag agtggactat gactatacta tatatctttg | 1380 |
| ttttttgttt ttgaaaatca aacgccgaag agtcttcttt attttctctt ctgaaaaaaa | 1440 |
| aaaaatcagt gggaaattaa atcatgtgtt gctattagca ttttctcttc tttattttgt | 1500 |
| tattatatat tgtttgtgat catccaattg atgcatttaa atttatgttg gtgttatttg | 1560 |
| tgtagctgtt tggtgtaacc atgg | 1584 |

<210> SEQ ID NO 2
<211> LENGTH: 1334
<212> TYPE: DNA
<213> ORGANISM: Glycine max

<400> SEQUENCE: 2

| | |
|---|---:|
| cgttcctgt ttaggaaagt cgatccataa agttttcact ccattattta atcagtttaa | 60 |
| tgccgtttaa tattttgta ctgatgtaaa ataatttat attattattt taaaagttaa | 120 |
| taaatttgaa taattttta ctgtataatt ctttttctct tatataatta gtcactgcac | 180 |
| tagaatcaga acctaattca cttttggaaa cgattaccaa aataaataaa taaccatgct | 240 |
| gacgaaaaat ttaaaaatat tgatagtact gcttggttat tggcaaacta agttttgata | 300 |
| tgtactagca ggagccgaga tatttaattt atagcatttg gattaattag ttttgtggta | 360 |
| agaaataatc aattatttat ttatgatgga cataaaagaa taaatagttg tttatacttt | 420 |
| ttcacaattt tatcatattt ttattgagta gaattaatta ttttgtatta ttcaaacacc | 480 |
| ctattagtat tgaaaaaaat acttgaaagg gacgaattcg tcactgactt gtggctcctt | 540 |
| ggtcttaaag tgttggtaat gcgattttaa atatcaataa taattaaaat gtgaaaagag | 600 |
| aaaatatttt atactagtat gttaggtaaa atcttatcaa gctaatttaa gatatacttt | 660 |
| tatcttatct tgcatatgcg atgtacaaat taaagaacat tcaatatata ttaattagaa | 720 |

```
aaaagttact gttaaaattt caaaggtagc gagaggaata atatggtatc acatggacaa      780
tagttatggt gaagagagtg atagactgat ggatgggaca aagacaaaag cacttccaaa      840
ataagagagt agttcaattc aacttaatta gtaagtaata tgcatattaa ggaagcattg      900
caattttgca aattaaaaca aacccatcac aattaatata gcatgactca cctaccatca      960
ttatttgtga aactgattta tcattccttg gctcactctt tcctaattct aaagtactcc     1020
ctctctatat aaattctcac tcaccttagt tttcttctca tttcactcac ttgctttcaa     1080
attctcattt tcaaggtgag agtggactat gactatacta tatatctttg ttttttgttt     1140
ttgaaaatca aacgccgaag agtcttcttt attttctctt ctgaaaaaaa aaaaatcagt     1200
gggaaattaa atcatgtgtt gctattagca ttttctcttc tttattttgt tattatatat     1260
tgtttgtgat catccaattg atgcatttaa atttatgttg gtgttatttg tgtagctgtt     1320
tggtgtaacc atgg                                                       1334

<210> SEQ ID NO 3
<211> LENGTH: 1149
<212> TYPE: DNA
<213> ORGANISM: Glycine max

<400> SEQUENCE: 3
tcagaaccta attcactttt ggaaacgatt accaaaataa ataaataacc atgctgacga       60
aaaatttaaa aatattgata gtactgcttg gttattggca aactaagttt tgatatgtac      120
tagcaggagc cgagatattt aatttatagc atttggatta attagttttg tggtaagaaa      180
taatcaatta tttatttatg atggacataa aagaataaat agttgtttat acttttcac      240 aatttttatca tatttttatt gagtagaatt aattattttg tattattcaa acaccctatt      300
agtattgaaa aaaatacttg aaagggacga attcgtcact gacttgtggc tccttggtct      360
taaagtgttg gtaatgcgat tttaaatatc aataataatt aaaatgtgaa agagaaaaa      420 tatttatact agtatgttag gtaaaatctt atcaagctaa tttaagatat acttttatct      480
tatcttgcat atgcgatgta caaattaaag aacattcaat atatattaat tagaaaaaag      540
ttactgttaa aatttcaaag gtagcgagag gaataatatg gtatcacatg gacaatagtt      600
atggtgaaga gagtgataga ctgatggatg ggacaaagac aaaagcactt ccaaataag      660 agagtagttc aattcaactt aattagtaag taatatgcat attaaggaag cattgcaatt      720
ttgcaaatta aacaaaccc atcacaatta atatagcatg actcacctac catcattatt      780
tgtgaaactg atttatcatt ccttggctca ctcttcctca ttctaaagt actccctctc      840 tatataaatt ctcactcacc ttagtttct tctcatttca ctcacttgct ttcaaattct      900
cattttcaag gtgagagtgg actatgacta tactatat ctttgttttt tgttttgaa      960 aatcaaacgc cgaagagtct tctttatttt ctcttctgaa aaaaaaaa tcagtgggaa     1020 attaaatcat gtgttgctat tagcattttc tcttctttat tttgttatta tatattgttt     1080
gtgatcatcc aattgatgca tttaaattta tgttggtgtt atttgtgtag ctgtttggtg     1140
taaccatgg                                                             1149

<210> SEQ ID NO 4
<211> LENGTH: 930
<212> TYPE: DNA
<213> ORGANISM: Glycine max

<400> SEQUENCE: 4
```

```
tagttgttta tacttttttca caatttttatc atatttttat tgagtagaat taattatttt      60
gtattattca aacaccctat tagtattgaa aaaaatactt gaaagggacg aattcgtcac       120
tgacttgtgg ctccttggtc ttaaagtgtt ggtaatgcga ttttaaatat caataataat       180
taaaatgtga aaagagaaaa atatttatac tagtatgtta ggtaaaatct tatcaagcta       240
atttaagata tacttttatc ttatcttgca tatgcgatgt acaaattaaa gaacattcaa       300
tatatattaa ttagaaaaaa gttactgtta aaatttcaaa ggtagcgaga ggaataatat       360
ggtatcacat ggacaatagt tatggtgaag agagtgatag actgatggat gggacaaaga       420
caaaagcact tccaaaataa gagagtagtt caattcaact taattagtaa gtaatatgca       480
tattaaggaa gcattgcaat tttgcaaatt aaaacaaacc catcacaatt aatatagcat       540
gactcaccta ccatcattat ttgtgaaact gatttatcat tccttggctc actctttcct       600
aattctaaag tactccctct ctatataaat tctcactcac cttagttttc ttctcatttc       660
actcacttgc tttcaaattc tcattttcaa ggtgagagtg gactatgact atactatata       720
tctttgtttt ttgttttttga aaatcaaacg ccgaagagtc ttctttattt tctcttctga     780
aaaaaaaaaa atcagtggga aattaaatca tgtgttgcta ttagcatttt ctcttcttta      840
ttttgttatt atatattgtt tgtgatcatc caattgatgc atttaaattt atgttggtgt      900
tatttgtgta gctgtttggt gtaaccatgg                                       930

<210> SEQ ID NO 5
<211> LENGTH: 721
<212> TYPE: DNA
<213> ORGANISM: Glycine max

<400> SEQUENCE: 5
ctagtatgtt aggtaaaatc ttatcaagct aatttaagat atactttat cttatcttgc        60 atatgcgatg tacaaattaa agaacattca atatatatta attagaaaaa agttactgtt      120
aaaatttcaa aggtagcgag aggaataata tggtatcaca tggacaatag ttatggtgaa      180
gagagtgata gactgatgga tgggacaaag acaaaagcac ttccaaaata agagagtagt      240
tcaattcaac ttaattagta agtaatatgc atattaagga agcattgcaa ttttgcaaat     300
taaaacaaac ccatcacaat taatatagca tgactcacct accatcatta tttgtgaaac      360
tgatttatca ttccttggct cactctttcc taattctaaa gtactccctc tctatataaa      420
ttctcactca ccttagtttt cttctcattt cactcacttg ctttcaaatt ctcattttca      480
aggtgagagt ggactatgac tatactatat atctttgttt tttgttttg aaaatcaaac       540 gccgaagagt cttctttatt ttctcttctg aaaaaaaaaa atcagtggg aaattaaatc       600 atgtgttgct attagcattt tctcttcttt attttgttat tatatattgt tgtgatcat       660 ccaattgatg catttaaatt tatgttggtg ttatttgtgt agctgtttgg tgtaaccatg      720
g                                                                      721

<210> SEQ ID NO 6
<211> LENGTH: 606
<212> TYPE: DNA
<213> ORGANISM: Glycine max

<400> SEQUENCE: 6
ctgttaaaat ttcaaaggta gcgagaggaa taatatggta tcacatggac aatagttatg       60
gtgaagagag tgatagactg atggatggga caaagacaaa agcacttcca aaataagaga      120
gtagttcaat tcaacttaat tagtaagtaa tatgcatatt aaggaagcat tgcaattttg      180
```

```
caaattaaaa caaacccatc acaattaata tagcatgact cacctaccat cattatttgt    240
gaaactgatt tatcattcct tggctcactc tttcctaatt ctaaagtact ccctctctat    300
ataaattctc actcacctta gttttcttct catttcactc acttgctttc aaattctcat    360
tttcaaggtg agagtggact atgactatac tatatatctt tgttttttgt ttttgaaaat    420
caaacgccga agagtcttct ttattttctc ttctgaaaaa aaaaaaatca gtgggaaatt    480
aaatcatgtg ttgctattag catttctct tctttatttt gttattatat attgtttgtg     540
atcatccaat tgatgcattt aaatttatgt tggtgttatt tgtgtagctg tttggtgtaa    600
ccatgg                                                               606

<210> SEQ ID NO 7
<211> LENGTH: 487
<212> TYPE: DNA
<213> ORGANISM: Glycine max

<400> SEQUENCE: 7
agtagttcaa ttcaacttaa ttagtaagta atatgcatat taaggaagca ttgcaatttt    60
gcaaattaaa acaaacccat cacaattaat atagcatgac tcacctacca tcattatttg    120
tgaaactgat ttatcattcc ttggctcact cttttcctaat tctaaagtac tccctctcta   180
tataaattct cactcacctt agttttcttc tcatttcact cacttgcttt caaattctca    240
ttttcaaggt gagagtggac tatgactata ctatatatct ttgttttttg tttttgaaaa    300
tcaaacgccg aagagtcttc tttattttct cttctgaaaa aaaaaaaatc agtgggaaat    360
taaatcatgt gttgctatta gcattttctc ttctttattt tgttattata tattgtttgt    420
gatcatccaa ttgatgcatt taaatttatg ttggtgttat tgtgtagct gtttggtgta     480 accatgg                                                              487

<210> SEQ ID NO 8
<211> LENGTH: 376
<212> TYPE: DNA
<213> ORGANISM: Glycine max

<400> SEQUENCE: 8
cattatttgt gaaactgatt tatcattcct tggctcactc tttcctaatt ctaaagtact    60
ccctctctat ataaattctc actcacctta gttttcttct catttcactc acttgctttc    120
aaattctcat tttcaaggtg agagtggact atgactatac tatatatctt tgttttttgt    180
ttttgaaaat caaacgccga agagtcttct ttattttctc ttctgaaaaa aaaaaaatca    240
gtgggaaatt aaatcatgtg ttgctattag catttctct tctttatttt gttattatat     300
attgtttgtg atcatccaat tgatgcattt aaatttatgt tggtgttatt tgtgtagctg    360
tttggtgtaa ccatgg                                                    376

<210> SEQ ID NO 9
<211> LENGTH: 1359
<212> TYPE: DNA
<213> ORGANISM: Glycine max

<400> SEQUENCE: 9
attgtttcca tgaatccttc aagtcgacga tttttttatt tttttatttt ttatttttta    60
tttttggtat aattcgacga aacttgggtt cattatttga gtccaatgtt cagtttacgc    120
gcttaaatta gtactattct atcttaatta ctttttctta tttctaacat tgttgaatta    180
```

```
gctttcccaa tcttctaaaa aaagcgtttc cgtgttatca gttgatgctg caaaaggaaa      240
ccagacgttt cctgtttagg aaagtcgatc cataaagttt tcactccatt atttaatcag      300
tttaatgccg tttaatattt ttgtactgat gtaaaataat tttatattat tattttaaaa      360
gttaataaat ttgaataatt ttttactgta taattctttt tctcttatat aattagtcac      420
tgcactagaa tcagaaccta attcactttt ggaaacgatt accaaaataa ataaataacc      480
atgctgacga aaaatttaaa aatattgata gtactgcttg gttattggca aactaagttt      540
tgatatgtac tagcaggagc cgagatattt aatttatagc atttggatta attagttttg      600
tggtaagaaa taatcaatta tttatttatg atggacataa aagaaataaa agttgtttat      660 acttttcac aattttatca tatttttatt gagtagaatt aattattttg tattattcaa       720
acaccctatt agtattgaaa aaaatacttg aaagggacga attcgtcact gacttgtggc      780
tccttggtct taaagtgttg gtaatgcgat tttaaatatc aataataatt aaaatgtgaa      840
aagagaaaaa tatttatact agtatgttag gtaaaatctt atcaagctaa tttaagatat      900
acttttatct tatcttgcat atgcgatgta caaattaaag aacattcaat atatattaat      960
tagaaaaaag ttactgttaa aatttcaaag gtagcgagag gaataatatg gtatcacatg     1020
gacaatagtt atggtgaaga gagtgataga ctgatggatg ggacaaagac aaaagcactt     1080
ccaaaataag agagtagttc aattcaactt aattagtaag taatatgcat attaaggaag     1140
cattgcaatt ttgcaaatta aaacaaaccc atcacaatta atatagcatg actcacctac     1200
catcattatt tgtgaaactg atttatcatt ccttggctca ctctttccta attctaaagt     1260
actccctctc tatataaatt ctcactcacc ttagttttct tctcatttca ctcacttgct     1320
ttcaaattct cattttcaag ctgtttggtg taaccatgg                            1359

<210> SEQ ID NO 10
<211> LENGTH: 32
<212> TYPE: DNA
<213> ORGANISM: Artificial sequence
<220> FEATURE:
<223> OTHER INFORMATION: Primer, PSO382305Xma

<400> SEQUENCE: 10
cccgggattg tttccatgaa tccttcaagt cg                                     32

<210> SEQ ID NO 11
<211> LENGTH: 35
<212> TYPE: DNA
<213> ORGANISM: Artificial sequence
<220> FEATURE:
<223> OTHER INFORMATION: Primer, PSO382305Nco

<400> SEQUENCE: 11
ccatggttac accaaacagc tacacaaata acacc                                  35

<210> SEQ ID NO 12
<211> LENGTH: 32
<212> TYPE: DNA
<213> ORGANISM: Artificial sequence
<220> FEATURE:
<223> OTHER INFORMATION: Primer, HRP1-S1

<400> SEQUENCE: 12
cccgggcgtt tcctgtttag gaaagtcgat cc                                     32

<210> SEQ ID NO 13
<211> LENGTH: 33
```

<212> TYPE: DNA
<213> ORGANISM: Artificial sequence
<220> FEATURE:
<223> OTHER INFORMATION: Primer, HRP1-S2

<400> SEQUENCE: 13
cccgggtcag aacctaattc acttttggaa acg                                    33

<210> SEQ ID NO 14
<211> LENGTH: 42
<212> TYPE: DNA
<213> ORGANISM: Artificial sequence
<220> FEATURE:
<223> OTHER INFORMATION: Primer, HRP1-S3

<400> SEQUENCE: 14
cccgggtagt tgtttatact ttttcacaat tttatcatat tt                          42

<210> SEQ ID NO 15
<211> LENGTH: 44
<212> TYPE: DNA
<213> ORGANISM: Artificial sequence
<220> FEATURE:
<223> OTHER INFORMATION: Primer, HRP1-S4

<400> SEQUENCE: 15
cccgggctag tatgttaggt aaaatcttat caagctaatt taag                        44

<210> SEQ ID NO 16
<211> LENGTH: 34
<212> TYPE: DNA
<213> ORGANISM: Artificial sequence
<220> FEATURE:
<223> OTHER INFORMATION: Primer, HRP1-S5

<400> SEQUENCE: 16
cccgggctgt taaaatttca aaggtagcga gagg                                   34

<210> SEQ ID NO 17
<211> LENGTH: 43
<212> TYPE: DNA
<213> ORGANISM: Artificial sequence
<220> FEATURE:
<223> OTHER INFORMATION: Primer, HRP1-S6

<400> SEQUENCE: 17
cccggggagt agttcaattc aacttaatta gtaagtaata tgc                         43

<210> SEQ ID NO 18
<211> LENGTH: 38
<212> TYPE: DNA
<213> ORGANISM: Artificial sequence
<220> FEATURE:
<223> OTHER INFORMATION: Primer, HRP1-S7

<400> SEQUENCE: 18
cccgggcatt atttgtgaaa ctgatttatc attccttg                               38

<210> SEQ ID NO 19
<211> LENGTH: 47
<212> TYPE: DNA
<213> ORGANISM: Artificial sequence
<220> FEATURE:
<223> OTHER INFORMATION: Primer, HRP1Nco

<400> SEQUENCE: 19

```
ccatggttac accaaacagc ttgaaaatga gaatttgaaa gcaagtg                    47
```

<210> SEQ ID NO 20
<211> LENGTH: 1167
<212> TYPE: DNA
<213> ORGANISM: Glycine max

<400> SEQUENCE: 20

```
cactcacttg ctttcaaatt ctcattttca agctgtttgg tgtaaagatg ggacaagtgc     60
ttggttgtgt tcaagtgaag cagtcaactg tagccgtcaa ggaatgtttc gggaagtacg    120
atgatgttct tcaacctggt tgccattttg tgccatggtg tcttggctgc ggtgtggctg    180
gtgtcctttc tacgcgtgtc atgcagctaa gtcttcgttg tgaaactaag acaaaggaca    240
atgtgtttgt taatgtggtt gcctcaatcc aatatcgagc attggcagaa aaggcatcag    300
atgcttacta caaactcacc aataccaaag cacagataca atcctatgtc tttgatgtta    360
tcagagctac tgttccaaag atggaacttg atgctgtttt tgagcagaag aacacaattg    420
caaaagcagt ggacgaagaa cttgggaagg ctatgtcagc atatgggtac gagatagttc    480
agactcttat tgtggatatt gtgccggatg agcatgtgaa gaaagccatg aatgagatta    540
atgctgctgc aagattgagg gtggctacaa acgacaaagc tgaagcagag aaaataatgc    600
agataaagcg agcagaaggg gatgcagaat caaagtacct agcaggcctt ggagtttctc    660
gtcagcgcca agccatagtt gatgggctaa gagacagtgt tctagcattt tctggtaatg    720
tgcctggaac atcatcaaag gatatcatgg acatggttct catgactcaa tattttgaca    780
caatgaagga gattggtgca tcctccaaat ccaatgctgt tttcattcca catggacctg    840
gtgctgtgag tgatgttgct tcacaagtaa ggaatggtct tctccaagga aatgcaacaa    900
cagagtcttg aagacataca catatatcat cataccatga tttcctcctc caggcacttg    960
tagtttagct ttgcaactaa atctttatat atgctactat tatgaatcat ccatggcaag   1020
ttggcaacta atgccttcta tatgtatatg gtcttcctaa tcaaccatgg caactttctt   1080
aattttatcc actattatga atcttcaact tttatgatat ctcattaaat ataatataat   1140
tacatacccca cgcgtatgca tgatttc                                      1167
```

<210> SEQ ID NO 21
<211> LENGTH: 287
<212> TYPE: PRT
<213> ORGANISM: Glycine max

<400> SEQUENCE: 21

```
Met Gly Gln Val Leu Gly Cys Val Gln Val Lys Gln Ser Thr Val Ala
1               5                   10                  15

Val Lys Glu Cys Phe Gly Lys Tyr Asp Asp Val Leu Gln Pro Gly Cys
            20                  25                  30

His Phe Val Pro Trp Cys Leu Gly Cys Gly Val Ala Gly Val Leu Ser
        35                  40                  45

Thr Arg Val Met Gln Leu Ser Leu Arg Cys Glu Thr Lys Thr Lys Asp
    50                  55                  60

Asn Val Phe Val Asn Val Val Ala Ser Ile Gln Tyr Arg Ala Leu Ala
65                  70                  75                  80

Glu Lys Ala Ser Asp Ala Tyr Tyr Lys Leu Thr Asn Thr Lys Ala Gln
                85                  90                  95

Ile Gln Ser Tyr Val Phe Asp Val Ile Arg Ala Thr Val Pro Lys Met
            100                 105                 110
```

-continued

```
Glu Leu Asp Ala Val Phe Glu Gln Lys Asn Thr Ile Ala Lys Ala Val
    115                 120                 125

Asp Glu Glu Leu Gly Lys Ala Met Ser Ala Tyr Gly Tyr Glu Ile Val
130                 135                 140

Gln Thr Leu Ile Val Asp Ile Val Pro Asp Glu His Val Lys Lys Ala
145                 150                 155                 160

Met Asn Glu Ile Asn Ala Ala Arg Leu Arg Val Ala Thr Asn Asp
                165                 170                 175

Lys Ala Glu Ala Glu Lys Ile Met Gln Ile Lys Arg Ala Glu Gly Asp
                180                 185                 190

Ala Glu Ser Lys Tyr Leu Ala Gly Leu Gly Val Ser Arg Gln Arg Gln
    195                 200                 205

Ala Ile Val Asp Gly Leu Arg Asp Ser Val Leu Ala Phe Ser Gly Asn
    210                 215                 220

Val Pro Gly Thr Ser Ser Lys Asp Ile Met Asp Met Val Leu Met Thr
225                 230                 235                 240

Gln Tyr Phe Asp Thr Met Lys Glu Ile Gly Ala Ser Ser Lys Ser Asn
                245                 250                 255

Ala Val Phe Ile Pro His Gly Pro Gly Ala Val Ser Asp Val Ala Ser
                260                 265                 270

Gln Val Arg Asn Gly Leu Leu Gln Gly Asn Ala Thr Thr Glu Ser
    275                 280                 285

<210> SEQ ID NO 22
<211> LENGTH: 4927
<212> TYPE: DNA
<213> ORGANISM: Artificial sequence
<220> FEATURE:
<223> OTHER INFORMATION: Plasmid, QC641

<400> SEQUENCE: 22
ccgggattgt tccatgaat ccttcaagtc gacgattttt ttatttttta ttttttattt      60 tttattttg gtataattcg acgaaacttg ggttcattat ttgagtccaa tgttcagttt     120
acgcgcttaa attagtacta ttctatctta attacttttt cttatttcta acattgttga    180
attagctttc ccaatcttct aaaaaaagcg tttccgtgtt atcagttgat gctgcaaaag    240
gaaaccagac gtttcctgtt taggaaagtc gatccataaa gttttcactc cattatttaa    300
tcagtttaat gccgtttaat attttgtac tgatgtaaaa aatttttata ttattatttt    360
aaaagttaat aaatttgaat aattttttac tgtataattc ttttctctt atataattag    420 tcactgcact agaatcagaa cctaattcac ttttggaaac gattaccaaa ataaataaat    480
aaccatgctg acgaaaaatt taaaaatatt gatagtactg cttggttatt ggcaaactaa    540
gttttgatat gtactagcag gagccgagat atttaattta tagcatttgg attaattagt    600
tttgtggtaa gaaataatca attatttatt tatgatggac ataaaagaat aaatagttgt    660
ttatactttt tcacaatttt atcatatttt tattgagtag aattaattat tttgtattat    720
tcaaacaccc tattagtatt gaaaaaata cttgaaaggg acgaattcgt cactgacttg    780
tggctccttg gtcttaaagt gttggtaatg cgatttttaaa tatcaataat aattaaaatg    840 tgaaagaga aaaatattta tactagtatg ttaggtaaaa tcttatcaag ctaatttaag    900
atatactttt atcttatctt gcatatgcga tgtacaaatt aaagaacatt caatatatat    960
taattagaaa aaagttactg ttaaaatttc aaaggtagcg agaggaataa tatggtatca   1020
catggacaat agttatggtg aagagagtga tagactgatg gatgggacaa agacaaaagc   1080
```

```
acttccaaaa taagagagta gttcaattca acttaattag taagtaatat gcatattaag    1140
gaagcattgc aattttgcaa attaaaacaa acccatcaca attaatatag catgactcac    1200
ctaccatcat tatttgtgaa actgatttat cattccttgg ctcactcttt cctaattcta    1260
aagtactccc tctctatata aattctcact caccttagtt ttcttctcat ttcactcact    1320
tgctttcaaa ttctcatttt caaggtgaga gtggactatg actatactat atatctttgt    1380
tttttgtttt tgaaaatcaa acgccgaaga gtcttcttta ttttctcttc tgaaaaaaaa    1440
aaaatcagtg ggaaattaaa tcatgtgttg ctattagcat tttctcttct ttattttgtt    1500
attatatatt gtttgtgatc atccaattga tgcatttaaa tttatgttgg tgttatttgt    1560
gtagctgttt ggtgtaacca tggcccagtc caagcacggc ctgaccaagg agatgaccat    1620
gaagtaccgc atggagggct gcgtggacgg ccacaagttc gtgatcaccg gcgagggcat    1680
cggctacccc ttcaagggca agcaggccat caacctgtgc gtggtggagg gcggcccctt    1740
gcccttcgcc gaggacatct tgtccgccgc cttcatgtac ggcaaccgcg tgttcaccga    1800 gtaccccag acatcgtcg actacttcaa gaactcctgc cccgccggct acacctggga    1860 ccgctcctc ctgttcgagg acggcgccgt gtgcatctgc aacgccgaca tcaccgtgag    1920
cgtggaggag aactgcatgt accacgagtc caagttctac ggcgtgaact tccccgccga    1980
cggccccgtg atgaagaaga tgaccgacaa ctgggagccc tcctgcgaga agatcatccc    2040
cgtgcccaag cagggcatct tgaagggcga cgtgagcatg tacctgctgc tgaaggacgg    2100
tggccgcttg cgctgccagt tcgacaccgt gtacaaggcc aagtccgtgc ccgcaagat    2160 gcccgactgg cacttcatcc agcacaagct gacccgcgag gaccgcagcg acgccaagaa    2220
ccagaagtgg cacctgaccg agcacgccat cgcctccggc tccgccttgc cctccggact    2280
cagatctcga ctagagtcga acctagactt gtccatcttc tggattggcc aacttaatta    2340
atgtatgaaa taaaaggatg cacacatagt gacatgctaa tcactataat gtgggcatca    2400
aagttgtgtg ttatgtgtaa ttactagtta tctgaataaa agagaaagag atcatccata    2460
tttcttatcc taaatgaatg tcacgtgtct ttataattct ttgatgaacc agatgcattt    2520
cattaaccaa atccatatac atataaatat taatcatata taattaatat caattgggtt    2580
agcaaaacaa atctagtcta ggtgtgtttt gcgaattcta gtggccggcc cagctgatat    2640
ccatcacact ggcggccgca ctcgactgaa ttggttccgg cgccagcctg cttttttgta    2700
caaagttggc attataaaaa agcattgctt atcaatttgt tgcaacgaac aggtcactat    2760
cagtcaaaat aaaatcatta tttgggggccc gagcttaagt aactaactaa caggaagagt    2820
ttgtagaaac gcaaaaggc catccgtcag gatggccttc tgcttagttt gatgcctggc    2880
agtttatggc gggcgtcctg cccgccaccc tccgggccgt tgcttcacaa cgttcaaatc    2940
cgctcccggc ggatttgtcc tactcaggag agcgttcacc gacaaacaac agataaaacg    3000
aaaggcccag tcttccgact gagcctttcg ttttatttga tgcctggcag ttccctactc    3060
tcgcttagta gttagacgtc cccgagatcc atgctagcgg taatacggtt atccacagaa    3120 tcagggata acgcaggaaa gaacatgtga gcaaaaggcc agcaaaggcc aggaaccgt    3180 aaaaaggccg cgttgctggc gttttccat aggctccgcc ccctgacga gcatcacaaa    3240 aatcgacgct caagtcagag gtggcgaaac ccgacaggac tataaagata ccaggcgttt    3300 cccctggaa gctccctcgt gcgctctcct gttccgaccc tgccgcttac cggatacctg    3360 tccgccttc tcccttcggg aagcgtggcg ctttctcata gctcacgctg taggtatctc    3420
agttcggtgt aggtcgttcg ctccaagctg ggctgtgtgc acgaaccccc cgttcagccc    3480
```

```
gaccgctgcg ccttatccgg taactatcgt cttgagtcca acccggtaag acacgactta    3540
tcgccactgg cagcagccac tggtaacagg attagcagag cgaggtatgt aggcggtgct    3600
acagagttct tgaagtggtg gcctaactac ggctacacta agaacagt   atttggtatc    3660 tgcgctctgc tgaagccagt taccttcgga aaaagagttg gtagctcttg atccggcaaa    3720
caaaccaccg ctggtagcgg tggtttttt  gtttgcaagc agcagattac gcgcagaaaa    3780
aaaggatctc aagaagatcc tttgatcttt tctacggggt ctgacgctca gtggaacggg    3840
gcccaatctg aataatgtta caaccaatta accaattctg attagaaaaa ctcatcgagc    3900
atcaaatgaa actgcaattt attcatatca ggattatcaa taccatattt ttgaaaaagc    3960
cgtttctgta atgaaggaga aaactcaccg aggcagttcc ataggatggc aagatcctgg    4020
tatcggtctg cgattccgac tcgtccaaca tcaatacaac ctattaattt ccctcgtca    4080 aaaataaggt tatcaagtga aaatcacca  tgagtgacga ctgaatccgg tgagaatggc    4140
aaaagtttat gcattctttt ccagacttgt tcaacaggcc agccattacg ctcgtcatca    4200
aaatcactcg catcaaccaa accgttattc attcgtgatt gcgcctgagc gagacgaaat    4260
acgcgatcgc tgttaaaagg acaattacaa acaggaatcg aatgcaaccg cgcaggaac    4320 actgccagcg catcaacaat attttcacct gaatcaggat attcttctaa tacctggaat    4380 gctgttttc  cggggatcgc agtggtgagt aaccatgcat catcaggagt acggataaaa    4440
tgcttgatgg tcggaagagg cataaattcc gtcagccagt ttagtctgac catctcatct    4500
gtaacatcat tggcaacgct acctttgcca tgtttcagaa acaactctgg cgcatcgggc    4560
ttcccataca agcgatagat tgtcgcacct gattgcccga cattatcgcg agcccattta    4620
tacccatata aatcagcatc catgttggaa tttaatcgcg gcctcgacgt ttcccgttga    4680
atatggctca taacaccct  tgtattactg tttatgtaag cagacagttt tattgttcat    4740
gatgatatat ttttatcttg tgcaatgtaa catcagagat tttgagacac gggccagagc    4800
tgcagctgga tggcaaataa tgattttatt ttgactgata gtgacctgtt cgttgcaaca    4860
aattgataag caatgctttc ttataatgcc aactttgtac aagaaagctg ggtctagata    4920
tctcgac                                                              4927
```

<210> SEQ ID NO 23  
<211> LENGTH: 8482  
<212> TYPE: DNA  
<213> ORGANISM: Artificial sequence  
<220> FEATURE:  
<223> OTHER INFORMATION: Plasmid, QC478i

<400> SEQUENCE: 23

```
atcgaaccac tttgtacaag aaagctgaac gagaaacgta aaatgatata aatatcaata     60
tattaaatta gattttgcat aaaaaacaga ctacataata ctgtaaaaca caacatatcc    120
agtcactatg gtcgacctgc agactggctg tgtataaggg agcctgacat ttatattccc    180
cagaacatca ggttaatggc gtttttgatg tcattttcgc ggtggctgag atcagccact    240
tcttccccga taacggagac cggcacactg gccatatcgg tggtcatcat gcgccagctt    300
tcatccccga tatgcaccac cgggtaaagt tcacggggga ctttatctga cagcagacgt    360
gcactggcca gggggatcac catccgtcgc ccgggcgtgt caataatatc actctgtaca    420
tccacaaaca gacgataacg gctctctctt ttataggtgt aaaccttaaa ctgcatttca    480
ccagcccctg ttctcgtcag caaaagagcc gttcatttca ataaaccggg cgacctcagc    540
```

```
catcccttcc tgattttccg ctttccagcg ttcggcacgc agacgacggg cttcattctg    600
catggttgtg cttaccagac cggagatatt gacatcatat atgccttgag caactgatag    660
ctgtcgctgt caactgtcac tgtaatacgc tgcttcatag catacctctt tttgacatac    720
ttcgggtata catatcagta tatattctta taccgcaaaa atcagcgcgc aaatacgcat    780
actgttatct ggcttttagt aagccggatc ctctagatta cgccccgcct gccactcatc    840
gcagtactgt tgtaattcat taagcattct gccgacatgg aagccatcac aaacggcatg    900
atgaacctga atcgccagcg gcatcagcac cttgtcgcct tgcgtataat atttgcccat    960
ggtgaaaacg ggggcgaaga agttgtccat attggccacg tttaaatcaa aactggtgaa   1020
actcacccag ggattggctg agacgaaaaa catattctca ataaacccct tagggaaata   1080
ggccaggttt tcaccgtaac acgccacatc ttgcgaatat atgtgtagaa actgccggaa   1140
atcgtcgtgg tattcactcc agagcgatga aaacgtttca gtttgctcat ggaaaacggt   1200
gtaacaaggg tgaacactat cccatatcac cagctcaccg tctttcattg ccatacggaa   1260
ttccggatga gcattcatca ggcgggcaag aatgtgaata aaggccggat aaaacttgtg   1320 cttattttc tttacggtct ttaaaaaggc cgtaatatcc agctgaacgg tctggttata   1380
ggtacattga gcaactgact gaaatgcctc aaaatgttct ttacgatgcc attgggatat   1440
atcaacggtg gtatatccag tgatttttt ctccatttta gcttccttag ctcctgaaaa   1500
tctcgacgga tcctaactca aaatccacac attatacgag ccggaagcat aaagtgtaaa   1560
gcctggggtg cctaatgcgg ccgccatagt gactggatat gttgtgtttt acagtattat   1620
gtagtctgtt tttatgcaa atctaattt aatatattga tatttatatc attttacgtt   1680
tctcgttcag ctttttttgta caaacttgtt tgataaacac tagtaacggc cgccagtgtg   1740
ctggaattcg cccttcccaa gctttgctct agatcaaact cacatccaaa cataacatgg   1800
atatcttcct taccaatcat actaattatt ttgggttaaa tattaatcat tattttaag   1860 atattaatta agaaattaaa agatttttta aaaaaatgta taaaattata ttattcatga   1920
tttttcatac atttgatttt gataataaat atattttttt taatttctta aaaaatgttg   1980
caagacactt attagacata gtcttgttct gtttacaaaa gcattcatca tttaatacat   2040 taaaaatat ttaatactaa cagtagaatc ttcttgtgag tggtgtggga gtaggcaacc   2100
tggcattgaa acgagagaaa gagagtcaga accagaagac aaataaaaag tatgcaacaa   2160
acaaatcaaa atcaaagggc aaaggctggg gttggctcaa ttggttgcta cattcaattt   2220
tcaactcagt caacggttga gattcactct gacttcccca atctaagccg cggatgcaaa   2280
cggttgaatc taacccacaa tccaatctcg ttacttaggg gcttttccgt cattaactca   2340
cccctgccac ccggtttccc tataaattgg aactcaatgc tcccctctaa actcgtatcg   2400
cttcagagtt gagaccaaga cacactcgtt catatatctc tctgctcttc tcttctcttc   2460
tacctctcaa ggtactttc ttctccctct accaaatcct agattccgtg gttcaatttc   2520
ggatcttgca cttctggttt gctttgcctt gcttttttcct caactgggtc catctaggat   2580
ccatgtgaaa ctctactctt tctttaatat ctgcggaata cgcgtttgac tttcagatct   2640
agtcgaaatc atttcataat tgcctttctt tcttttagct tatgagaaat aaaatcacttt   2700 ttttttatt tcaaaataaa ccttgggcct tgtgctgact gagatggggt ttggtgatta   2760
cagaatttta gcgaatttg taattgtact tgtttgtctg tagttttgtt ttgttttctt   2820
gtttctcata cattccttag gcttcaattt tattcgagta taggtcacaa taggaattca   2880
aactttgagc aggggaatta atccccttcct tcaaatccag tttgtttgta tatatgttta   2940
```

```
aaaaatgaaa cttttgcttt aaattctatt ataacttttt ttatggctga aattttttgca   3000 tgtgtctttg ctctctgttg taaatttact gtttaggtac taactctagg cttgttgtgc   3060 agttttttgaa gtataacaac agaagttcct attccgaagt tcctattctc tagaaagtat   3120
aggaacttcc accacacaac acaatggcgg ccaccgcttc cagaaccacc cgattctctt   3180
cttcctcttc acacccacc ttccccaaac gcattactag atccaccctc cctctctctc   3240
atcaaaccct caccaaaccc aaccacgctc tcaaaatcaa atgttccatc tccaaacccc   3300
ccacggcggc gcccttcacc aaggaagcgc cgaccacgga gcccttcgtg tcacggttcg   3360
cctccggcga acctcgcaag ggcgcggaca tccttgtgga ggcgctggag aggcagggcg   3420
tgacgacggt gttcgcgtac cccggcggtg cgtcgatgga gatccaccag gcgctcacgc   3480
gctccgccgc catccgcaac gtgctcccgc gccacgagca gggcggcgtc ttcgccgccg   3540
aaggctacgc gcgttcctcc ggcctccccg gcgtctgcat tgccacctcc ggccccggcg   3600
ccaccaacct cgtgagcggc ctcgccgacg ctttaatgga cagcgtccca gtcgtcgcca   3660
tcaccggcca ggtcgcccgc cggatgatcg gcaccgacgc cttccaagaa accccgatcg   3720
tggaggtgag cagatccatc acgaagcaca actacctcat cctcgacgtc gacgacatcc   3780
cccgcgtcgt cgccgaggct ttcttcgtcg ccacctccgg ccgccccggt ccggtcctca   3840
tcgacattcc caaagacgtt cagcagcaac tcgccgtgcc taattgggac gagcccgtta   3900
acctccccgg ttacctcgcc aggctgccca ggccccccgc cgaggcccaa ttggaacaca   3960
ttgtcagact catcatggag gcccaaaagc ccgttctcta cgtcggcggt ggcagtttga   4020
attccagtgc tgaattgagg cgctttgttg aactcactgg tattcccgtt gctagcactt   4080
taatgggtct tggaactttt cctattggtg atgaatattc ccttcagatg ctgggtatgc   4140
atggtactgt ttatgctaac tatgctgttg acaatagtga tttgttgctt gcctttgggg   4200
taaggtttga tgaccgtgtt actgggaagc ttgaggcttt tgctagtagg gctaagattg   4260
ttcacattga tattgattct gccgagattg gaagaacaa gcaggcgcac gtgtcggttt   4320
gcgcggattt gaagttggcc ttgaagggaa ttaatatgat tttggaggag aaaggagtgg   4380
agggtaagtt tgatcttgga ggttggagag aagagattaa tgtgcagaaa cacaagtttc   4440
cattgggtta caagacattc caggacgcga tttctccgca gcatgctatc gaggttcttg   4500
atgagttgac taatggagat gctattgtta gtactggggt tgggcagcat caaatgtggg   4560
ctgcgcagtt ttacaagtac aagagaccga ggcagtggtt gacctcaggg ggtcttggag   4620
ccatgggttt tggattgcct gcggctattg gtgctgctgt tgctaaccct ggggctgttg   4680
tggttgacat tgatggggat ggtagtttca tcatgaatgt tcaggagttg gccactataa   4740
gagtggagaa tctcccagtt aagatattgt tgttgaacaa tcagcatttg ggtatggtgg   4800
ttcagttgga ggataggttc tacaagtcca atagagctca cacctatctt ggagatccgt   4860
ctagcgagag cgagatattc ccaaacatgc tcaagtttgc tgatgcttgt gggataccgg   4920
cagcgcgagt gacgaagaag gaagagctta gagcggcaat tcagagaatg ttggacaccc   4980 ctggcccta ccttcttgat gtcattgtgc cccatcagga gcatgtgttg ccgatgattc   5040
ccagtaatgg atccttcaag gatgtgataa ctgagggtga tggtagaacg aggtactgat   5100
tgcctagacc aaaatgttcct tgatgcttgt tttgtacaat atatataaga taatgctgtc   5160
ctagttgcag gatttggcct gtggtgagca tcatagtctg tagtagtttt ggtagcaaga   5220 catttattt tcctttttatt taacttacta catgcagtag catctatcta tctctgtagt   5280
```

```
ctgatatctc ctgttgtctg tattgtgccg ttggattttt tgctgtagtg agactgaaaa    5340
tgatgtgcta gtaataatat ttctgttaga aatctaagta gagaatctgt tgaagaagtc    5400
aaaagctaat ggaatcaggt tacatattca atgtttttct ttttttagcg gttggtagac    5460
gtgtagattc aacttctctt ggagctcacc taggcaatca gtaaaatgca tattccttt     5520
ttaacttgcc atttatttac ttttagtgga aattgtgacc aatttgttca tgtagaacgg    5580
atttggacca ttgcgtccac aaaacgtctc ttttgctcga tcttcacaaa gcgataccga    5640
aatccagaga tagttttcaa aagtcagaaa tggcaaagtt ataaatagta aaacagaata    5700
gatgctgtaa tcgacttcaa taacaagtgg catcacgttt ctagttctag acccatcagc    5760
tgggccggcc cagctgatga tcccggtgaa gttcctattc cgaagttcct attctccaga    5820
aagtatagga acttcactag agcttgcggc cgcgcatgct gacttaatca gctaacgcca    5880
ctcgaggggg ggcccggtac cggcgcgccg ttctatagtg tcacctaaat cgtatgtgta    5940
tgatacataa ggttatgtat taattgtagc cgcgttctaa cgacaatatg tccatatggt    6000
gcactctcag tacaatctgc tctgatgccg catagttaag ccagccccga cacccgccaa    6060
cacccgctga cgcgccctga cgggcttgtc tgctcccggc atccgcttac agacaagctg    6120
tgaccgtctc cgggagctgc atgtgtcaga ggttttcacc gtcatcaccg aaacgcgcga    6180
gacgaaaggg cctcgtgata cgcctatttt tataggttaa tgtcatgacc aaaatccctt    6240
aacgtgagtt ttcgttccac tgagcgtcag accccgtaga aaagatcaaa ggatcttctt    6300
gagatccttt ttttctgcgc gtaatctgct gcttgcaaac aaaaaaacca ccgctaccag    6360
cggtggtttg tttgccggat caagagctac caactctttt tccgaaggta actggcttca    6420
gcagagcgca gataccaaat actgtccttc tagtgtagcc gtagttaggc caccacttca    6480
agaactctgt agcaccgcct acatacctcg ctctgctaat cctgttacca gtggctgctg    6540
ccagtggcga taagtcgtgt cttaccgggt tggactcaag acgatagtta ccggataagg    6600
cgcagcggtc gggctgaacg gggggttcgt gcacacagcc cagcttggag cgaacgacct    6660
acaccgaact gagataccta cagcgtgagc attgagaaag cgccacgctt cccgaaggga    6720
gaaaggcgga caggtatccg gtaagcggca gggtcggaac aggagagcgc acgagggagc    6780
ttccagggg  aaacgcctgg tatctttata gtcctgtcgg gtttcgccac ctctgacttg    6840
agcgtcgatt tttgtgatgc tcgtcagggg gcggagcct  atggaaaaac gccagcaacg    6900
cggccttttt acggttcctg gccttttgct ggccttttgc tcacatgttc tttcctgcgt    6960
tatccctga  ttctgtggat aaccgtatta ccgcctttga gtgagctgat accgctcgcc    7020
gcagccgaac gaccgagcgc agcgagtcag tgagcgagga agcggaagag cgcccaatac    7080
gcaaaccgcc tctccccgcg cgttggccga ttcattaatg caggttgatc agatctcgat    7140
cccgcgaaat taatacgact cactataggg agaccacaac ggtttccctc tagaaataat    7200
tttgtttaac tttaagaagg agatataccc atggaaaagc tgaactcac  cgcgacgtct    7260
gtcgagaagt ttctgatcga aaagttcgac agcgtctccg acctgatgca gctctcggag    7320
ggcgaagaat ctcgtgcttt cagcttcgat gtaggagggc gtggatatgt cctgcgggta    7380
aatagctgcg ccgatggttt ctacaaagat cgttatgttt atcggcactt tgcatcggcc    7440
gcgctcccga ttccggaagt gcttgacatt ggggaattca gcgagagcct gacctattgc    7500
atctcccgcc gtgcacaggg tgtcacgttg caagacctgc ctgaaaccga actgcccgct    7560
gttctgcagc cggtcgcgga ggctatggat gcgatcgctg cggccgatct tagccagacg    7620
agcgggttcg gcccattcgg accgcaagga atcggtcaat acactacatg gcgtgatttc    7680
```

```
atatgcgcga ttgctgatcc ccatgtgtat cactggcaaa ctgtgatgga cgacaccgtc      7740
agtgcgtccg tcgcgcaggc tctcgatgag ctgatgcttt gggccgagga ctgccccgaa      7800
gtccggcacc tcgtgcacgc ggatttcggc tccaacaatg tcctgacgga caatggccgc      7860
ataacagcgg tcattgactg gagcgaggcg atgttcgggg attcccaata cgaggtcgcc      7920
aacatcttct tctggaggcc gtggttggct tgtatggagc agcagacgcg ctacttcgag      7980
cggaggcatc cggagcttgc aggatcgccg cggctccggg cgtatatgct ccgcattggt      8040
cttgaccaac tctatcagag cttggttgac ggcaatttcg atgatgcagc ttgggcgcag      8100
ggtcgatgcg acgcaatcgt ccgatccgga gccgggactg tcgggcgtac acaaatcgcc      8160
cgcagaagcg cggccgtctg gaccgatggc tgtgtagaag tactcgccga tagtggaaac      8220
cgacgcccca gcactcgtcc gagggcaaag gaatagtgag gtacagcttg gatcgatccg      8280
gctgctaaca aagcccgaaa ggaagctgag ttggctgctg ccaccgctga gcaataacta      8340
gcataacccc ttggggcctc taaacgggtc ttgaggggtt ttttgctgaa aggaggaact      8400
atatccggat gctcgggcgc gccggtaccc gggtaccgag ctcactagac gcggtgaaat      8460
tacctaatta acaccggtgt tt                                              8482
```

<210> SEQ ID NO 24
<211> LENGTH: 9526
<212> TYPE: DNA
<213> ORGANISM: Artificial sequence
<220> FEATURE:
<223> OTHER INFORMATION: Plasmid, QC650

<400> SEQUENCE: 24

```
ccgggattgt ttccatgaat ccttcaagtc gacgattttt ttattttttta tttttattt        60 tttattttg gtataattcg acgaaacttg ggttcattat ttgagtccaa tgttcagttt       120
acgcgcttaa attagtacta ttctatctta attactttt cttatttcta acattgttga       180
attagctttc ccaatcttct aaaaaaagcg tttccgtgtt atcagttgat gctgcaaaag       240
gaaaccagac gtttcctgtt taggaaagtc gatccataaa gttttcactc cattatttaa       300
tcagtttaat gccgtttaat attttttgtac tgatgtaaaa taattttata ttattatttt      360
aaaagttaat aaatttgaat aattttttac tgtataattc tttttctctt atataattag      420
tcactgcact agaatcagaa cctaattcac ttttggaaac gattaccaaa ataaataaat      480
aaccatgctg acgaaaaatt taaaaatatt gatagtactg cttggttatt ggcaaactaa      540
gttttgatat gtactagcag gagccgagat atttaattta tagcatttgg attaattagt      600
tttgtggtaa gaaataatca attatttatt tatgatggac ataaaagaat aaatagttgt      660
ttatactttt tcacaatttt atcatatttt tattgagtag aattaattat tttgtattat      720
tcaaacaccc tattagtatt gaaaaaaata cttgaaaggg acgaattcgt cactgacttg      780
tggctccttg gtcttaaagt gttggtaatg cgattttaaa tatcaataat aattaaaatg      840 tgaaagaga aaaatattta tactagtatg ttaggtaaaa tcttatcaag ctaatttaag      900
atatactttt atcttatctt gcatatgcga tgtacaaatt aaagaacatt caatatatat      960
taattagaaa aaagttactg ttaaaatttc aaaggtagcg agaggaataa tatggtatca     1020
catggacaat agttatggtg aagagagtga tagactgatg gatgggacaa agacaaaagc     1080
acttccaaaa taagagagta gttcaattca acttaattag taagtaatat gcatattaag     1140
gaagcattgc aattttgcaa attaaaacaa acccatcaca attaatatag catgactcac     1200
```

```
ctaccatcat tatttgtgaa actgatttat cattccttgg ctcactcttt cctaattcta    1260
aagtactccc tctctatata aattctcact caccttagtt ttcttctcat ttcactcact    1320
tgctttcaaa ttctcatttt caaggtgaga gtggactatg actatactat atatctttgt    1380
tttttgtttt tgaaaatcaa acgccgaaga gtcttcttta ttttctcttc tgaaaaaaaa    1440
aaaatcagtg ggaaattaaa tcatgtgttg ctattagcat tttctcttct ttattttgtt    1500
attatatatt gtttgtgatc atccaattga tgcatttaaa tttatgttgg tgttatttgt    1560
gtagctgttt ggtgtaacca tggcccagtc caagcacggc ctgaccaagg agatgaccat    1620
gaagtaccgc atggagggct gcgtggacgg ccacaagttc gtgatcaccg gcgagggcat    1680
cggctacccc ttcaagggca gcaggccat caacctgtgc gtggtggagg gcggcccctt    1740
gcccttcgcc gaggacatct tgtccgccgc cttcatgtac ggcaaccgcg tgttcaccga    1800
gtacccccag gacatcgtcg actacttcaa gaactcctgc cccgccggct acacctggga    1860
ccgctccttc ctgttcgagg acggcgccgt gtgcatctgc aacgccgaca tcaccgtgag    1920
cgtggaggag aactgcatgt accacgagtc caagttctac ggcgtgaact tccccgccga    1980 cggcccccgtg atgaagaaga tgaccgacaa ctgggagccc tcctgcgaga agatcatccc    2040
cgtgcccaag cagggcatct tgaagggcga cgtgagcatg tacctgctgc tgaaggacgg    2100
tggccgcttg cgctgccagt tcgacaccgt gtacaaggcc aagtccgtgc cccgcaagat    2160
gcccgactgg cacttcatcc agcacaagct gaccccgcgag accgcagcg acgccaagaa    2220 ccagaagtgg cacctgaccg agcacgccat cgcctccggc tccgccttgc cctccggact    2280
cagatctcga ctagagtcga acctagactt gtccatcttc tggattggcc aacttaatta    2340
atgtatgaaa taaaggatg cacacatagt gacatgctaa tcactataat gtgggcatca    2400
aagttgtgtg ttatgtgtaa ttactagtta tctgaataaa agagaaagag atcatccata    2460
tttcttatcc taaatgaatg tcacgtgtct ttataattct ttgatgaacc agatgcattt    2520
cattaaccaa atccatatac atataaatat taatcatata taattaatat caattggggtt    2580 agcaaaacaa atctagtcta ggtgtgtttt gcgaattcta gtggccggcc cagctgatat    2640
ccatcacact ggcggccgca ctcgactgaa ttggttccgg cgccagcctg cttttttgta    2700
caaacttgtt tgataaacac tagtaacggc cgccagtgtg ctggaattcg cccttcccaa    2760
gctttgctct agatcaaact cacatccaaa cataacatgg atatcttcct taccaatcat    2820
actaattatt ttgggttaaa tattaatcat tatttttaag atattaatta agaaattaaa    2880
agatttttta aaaaaatgta taaaattata ttattcatga tttttcatac atttgatttt    2940
gataataaat atatttttt taatttctta aaaaatgttg caagacactt attagacata    3000
gtcttgttct gtttacaaaa gcattcatca tttaatacat taaaaaatat ttaatactaa    3060
cagtagaatc ttcttgtgag tggtgtggga gtaggcaacc tggcattgaa acgagagaaa    3120
gagagtcaga accagaagac aaataaaaag tatgcaacaa acaaatcaaa atcaaagggc    3180
aaaggctggg gttggctcaa ttggttgcta cattcaattt tcaactcagt caacggttga    3240
gattcactct gacttcccca atctaagccg cggatgcaaa cggttgaatc taacccacaa    3300
tccaatctcg ttacttaggg gcttttccgt cattaactca cccctgccac ccggtttccc    3360
tataaattgg aactcaatgc tcccctctaa actcgtatcg cttcagagtt gagaccaaga    3420
cacactcgtt catatatctc tctgctcttc tcttctcttc tacctctcaa ggtacttttc    3480
ttctccctct accaaatcct agattccgtg gttcaatttc ggatcttgca cttctggttt    3540
gctttgcctt gcttttttcct caactgggtc catctaggat ccatgtgaaa ctctactctt    3600
```

```
tctttaatat ctgcggaata cgcgtttgac tttcagatct agtcgaaatc atttcataat    3660
tgcctttctt tcttttagct tatgagaaat aaaatcactt ttttttttatt tcaaaataaa    3720 ccttgggcct tgtgctgact gagatggggt ttggtgatta cagaatttta gcgaattttg    3780
taattgtact tgtttgtctg tagttttgtt ttgttttctt gtttctcata cattccttag    3840
gcttcaattt tattcgagta taggtcacaa taggaattca aactttgagc aggggaatta    3900
atcccttcct tcaaatccag tttgtttgta tatatgttta aaaaatgaaa cttttgcttt    3960
aaattctatt ataactttt ttatggctga aattttgca tgtgtctttg ctctctgttg    4020
taaatttact gtttaggtac taactctagg cttgttgtgc agtttttgaa gtataacaac    4080
agaagttcct attccgaagt tcctattctc tagaaagtat aggaacttcc accacacaac    4140
acaatggcgg ccaccgcttc cagaaccacc cgattctctt cttcctcttc acccccacc    4200 ttccccaaac gcattactag atccaccctc cctctctctc atcaaaccct caccaaaccc    4260
aaccacgctc tcaaaatcaa atgttccatc tccaaacccc ccacggcggc gcccttcacc    4320
aaggaagcgc cgaccacgga gcccttcgtg tcacggttcg cctccggcga acctcgcaag    4380
ggcgcggaca tccttgtgga ggcgctggag aggcagggcg tgacgacggt gttcgcgtac    4440
cccggcggtg cgtcgatgga gatccaccag gcgctcacgc gctccgccgc catccgcaac    4500
gtgctcccgc gccacgagca gggcggcgtc ttcgccgccg aaggctacgc gcgttcctcc    4560
ggcctccccg gcgtctgcat tgccacctcc ggccccggcg ccaccaacct cgtgagcggc    4620
ctcgccgacg ctttaatgga cagcgtccca gtcgtcgcca tcaccggcca ggtcgcccgc    4680
cggatgatcg gcaccgacgc cttccaagaa acccgatcg tggaggtgag cagatccatc    4740
acgaagcaca actacctcat cctcgacgtc gacgacatcc cccgcgtcgt cgccgaggct    4800
ttcttcgtcg ccacctccgg ccgccccggt ccggtcctca tcgacattcc caaagacgtt    4860
cagcagcaac tcgccgtgcc taattgggac gagcccgtta acctcccggg ttacctcgcc    4920
aggctgccca ggcccccgc cgaggcccaa ttggaacaca ttgtcagact catcatggag    4980
gcccaaaagc ccgttctcta cgtcggcggt ggcagtttga attccagtgc tgaattgagg    5040
cgctttgttg aactcactgg tattcccgtt gctagcactt taatgggtct tggaactttt    5100
cctattggtg atgaatattc ccttcagatg ctgggtatgc atggtactgt ttatgctaac    5160
tatgctgttg caatagtga tttgttgctt gcctttgggg taaggtttga tgaccgtgtt    5220
actgggaagc ttgaggcttt tgctagtagg gctaagattg ttcacattga tattgattct    5280
gccgagattg gaagaacaa gcaggcgcac gtgtcggttt gcgcggattt gaagttggcc    5340
ttgaagggaa ttaatatgat tttggaggag aaaggagtgg agggtaagtt tgatcttgga    5400
ggttggagag aagagattaa tgtgcagaaa cacaagtttc cattgggtta caagacattc    5460
caggacgcga tttctccgca gcatgctatc gaggttcttg atgagttgac taatggagat    5520
gctattgtta gtactgggt tgggcagcat caaatgtggg ctgcgcagtt ttacaagtac    5580
aagagaccga ggcagtggtt gacctcaggg ggtcttggag ccatgggttt tggattgcct    5640
gcggctattg tgctgctgt tgctaaccct ggggctgttg tggttgacat tgatggggat    5700
ggtagtttca tcatgaatgt tcaggagttg gccactataa gagtggagaa tctcccagtt    5760
aagatattgt tgttgaacaa tcagcatttg ggtatggtgg ttcagttgga ggataggttc    5820
tacaagtcca atagagctca cacctatctt ggagatccgt ctagcgagag cgagatattc    5880
ccaaacatgc tcaagtttgc tgatgcttgt gggataccgg cagcgcgagt gacgaagaag    5940
```

```
gaagagctta gagcggcaat tcagagaatg ttggacaccc ctggcccta ccttcttgat      6000 gtcattgtgc cccatcagga gcatgtgttg ccgatgattc ccagtaatgg atccttcaag      6060
gatgtgataa ctgagggtga tggtagaacg aggtactgat tgcctagacc aaatgttcct      6120
tgatgcttgt tttgtacaat atatataaga taatgctgtc ctagttgcag gatttggcct      6180
gtggtgagca tcatagtctg tagtagtttt ggtagcaaga catttatttt tccttttatt      6240
taacttacta catgcagtag catctatcta tctctgtagt ctgatatctc ctgttgtctg      6300
tattgtgccg ttggattttt tgctgtagtg agactgaaaa tgatgtgcta gtaataatat      6360
ttctgttaga aatctaagta gagaatctgt tgaagaagtc aaaagctaat ggaatcaggt      6420
tacatattca atgttttct ttttttagcg gttggtagac gtgtagattc aacttctctt       6480
ggagctcacc taggcaatca gtaaaatgca tattccttt ttaacttgcc atttatttac       6540
ttttagtgga aattgtgacc aatttgttca tgtagaacgg atttggacca ttgcgtccac      6600
aaaacgtctc ttttgctcga tcttcacaaa gcgataccga aatccagaga tagttttcaa      6660
aagtcagaaa tggcaaagtt ataaatagta aaacagaata gatgctgtaa tcgacttcaa      6720
taacaagtgg catcacgttt ctagttctag acccatcagc tgggccggcc cagctgatga      6780 tccccggtgaa gttcctattc cgaagttcct attctccaga aagtatagga acttcactag     6840
agcttgcggc cgcgcatgct gacttaatca gctaacgcca ctcgaggggg ggcccggtac      6900
cggcgcgccg ttctatagtg tcacctaaat cgtatgtgta tgatacataa ggttatgtat      6960
taattgtagc cgcgttctaa cgacaatatg tccatatggt gcactctcag tacaatctgc      7020
tctgatgccg catagttaag ccagccccga caccgccaa cacccgctga cgcgccctga      7080
cgggcttgtc tgctcccggc atccgcttac agacaagctg tgaccgtctc cgggagctgc      7140
atgtgtcaga ggttttcacc gtcatcaccg aaacgcgcga gacgaaaggg cctcgtgata     7200
cgcctatttt tataggttaa tgtcatgacc aaaatccctt aacgtgagtt tcgttccac      7260 tgagcgtcag accccgtaga aaagatcaaa ggatcttctt gagatccttt ttttctgcgc     7320
gtaatctgct gcttgcaaac aaaaaaacca ccgctaccag cggtggtttg tttgccggat     7380
caagagctac caactctttt tccgaaggta actggcttca gcagagcgca gataccaaat     7440
actgtccttc tagtgtagcc gtagttaggc caccacttca agaactctgt agcaccgcct     7500
acatacctcg ctctgctaat cctgttacca gtggctgctg ccagtggcga taagtcgtgt     7560
cttaccgggt tggactcaag acgatagtta ccggataagg cgcagcggtc gggctgaacg     7620
gggggttcgt gcacacagcc cagcttggag cgaacgacct acaccgaact gagataccta     7680
cagcgtgagc attgagaaag cgccacgctt cccgaaggga gaaaggcgga caggtatccg     7740
gtaagcggca gggtcggaac aggagagcgc acgagggagc ttccaggggg aaacgcctgg     7800
tatctttata gtcctgtcgg gtttcgccac ctctgacttg agcgtcgatt tttgtgatgc     7860
tcgtcagggg ggcggagcct atggaaaaac gccagcaacg cggccttttt acggttcctg     7920
gccttttgct ggccttttgc tcacatgttc tttcctgcgt tatcccctga ttctgtggat      7980
aaccgtatta ccgcctttga gtgagctgat accgctcgcc gcagccgaac gaccgagcgc     8040
agcgagtcag tgagcgagga agcggaagag cgcccaatac gcaaaccgcc tctccccgcg     8100
cgttggccga ttcattaatg caggttgatc agatctcgat cccgcgaaat taatacgact     8160
cactataggg agaccacaac ggtttccctc tagaaataat tttgtttaac tttaagaagg     8220 agatatccc atgaaaagc ctgaactcac cgcgacgtct gtcgagaagt ttctgatcga       8280
aaagttcgac agcgtctccg acctgatgca gctctcggag ggcgaagaat ctcgtgcttt     8340
```

```
cagcttcgat gtaggagggc gtggatatgt cctgcgggta aatagctgcg ccgatggttt    8400
ctacaaagat cgttatgttt atcggcactt tgcatcggcc gcgctcccga ttccggaagt    8460
gcttgacatt ggggaattca gcgagagcct gacctattgc atctcccgcc gtgcacaggg    8520
tgtcacgttg caagacctgc ctgaaaccga actgcccgct gttctgcagc cggtcgcgga    8580
ggctatggat gcgatcgctg cggccgatct tagccagacg agcgggttcg gcccattcgg    8640
accgcaagga atcggtcaat acactacatg gcgtgatttc atatgcgcga ttgctgatcc    8700
ccatgtgtat cactggcaaa ctgtgatgga cgacaccgtc agtgcgtccg tcgcgcaggc    8760
tctcgatgag ctgatgcttt gggccgagga ctgccccgaa gtccggcacc tcgtgcacgc    8820
ggatttcggc tccaacaatg tcctgacgga caatggccgc ataacagcgg tcattgactg    8880
gagcgaggcg atgttcgggg attcccaata cgaggtcgcc aacatcttct tctgagggcc    8940
gtggttggct tgtatggagc agcagacgcg ctacttcgag cggaggcatc cggagcttgc    9000
aggatcgccg cggctcccgg cgtatatgct ccgcattggt cttgaccaac tctatcagag    9060
cttggttgac ggcaatttcg atgatgcagc ttgggcgcag ggtcgatgcg acgcaatcgt    9120
ccgatccgga gccgggactg tcgggcgtac acaaatcgcc cgcagaagcg cggccgtctg    9180
gaccgatggc tgtgtagaag tactcgccga tagtggaaac cgacgcccca gcactcgtcc    9240
gagggcaaag gaatagtgag gtacagcttg atcgatccg gctgctaaca aagcccgaaa    9300
ggaagctgag ttggctgctg ccaccgctga gcaataacta gcataacccc ttggggcctc    9360
taaacgggtc ttgaggggtt ttttgctgaa aggaggaact atatccggat gctcgggcgc    9420
gccggtaccc gggtaccgag ctcactagac gcggtgaaat tacctaatta acaccggtgt    9480
ttatcgaacc actttgtaca agaaagctgg gtctagatat ctcgac              9526

<210> SEQ ID NO 25
<211> LENGTH: 4683
<212> TYPE: DNA
<213> ORGANISM: Artificial sequence
<220> FEATURE:
<223> OTHER INFORMATION: Plasmid, QC641-1

<400> SEQUENCE: 25
ccgggcgttt cctgtttagg aaagtcgatc cataaagttt tcactccatt atttaatcag      60
tttaatgccg tttaatatttt ttgtactgat gtaaataat tttatattat tatttttaaa    120
gttaataaat ttgaataatt ttttactgta taattctttt tctcttatat aattagtcac    180
tgcactagaa tcagaaccta attcattttt ggaaacgatt accaaaataa ataaataacc    240
atgctgacga aaaatttaaa aatattgata gtactgcttg gttattggca aactaagttt    300
tgatatgtac tagcaggagc cgagatattt aatttatagc atttggatta attagttttg    360
tggtaagaaa taatcaatta tttatttatg atggacataa agaataaat agttgtttat    420 acttttcac aattttatca tattttatt gagtagaatt aattatttg tattattcaa    480 acaccctatt agtattgaaa aaaatacttg aaagggacga attcgtcact gacttgtggc    540
tccttggtct taaagtgttg gtaatgcgat tttaaatatc aataataatt aaaatgtgaa    600
aagagaaaaa tatttatact agtatgttag gtaaaatctt atcaagctaa tttaagatat    660 actttttatct tatcttgcat atgcgatgta caaattaaag aacattcaat atatattaat    720
tagaaaaaag ttactgttaa aatttcaaag gtagcgagag gaataatatg gtatcacatg    780
gacaatagtt atggtgaaga gagtgataga ctgatggatg ggacaaagac aaaagcactt    840
```

```
ccaaaataag agagtagttc aattcaactt aattagtaag taatatgcat attaaggaag    900
cattgcaatt ttgcaaatta aaacaaaccc atcacaatta atatagcatg actcacctac    960
catcattatt tgtgaaactg atttatcatt ccttggctca ctctttccta attctaaagt   1020
actccctctc tatataaatt ctcactcacc ttagttttct tctcatttca ctcacttgct   1080
ttcaaattct cattttcaag gtgagagtgg actatgacta tactatatat ctttgttttt   1140 tgttttttgaa aatcaaacgc cgaagagtct tctttatttt ctcttctgaa aaaaaaaaa   1200 tcagtgggaa attaaatcat gtgttgctat tagcattttc tcttctttat tttgttatta   1260
tatattgttt gtgatcatcc aattgatgca tttaaattta tgttggtgtt atttgtgtag   1320
ctgtttggtg taaccatggc ccagtccaag cacggcctga ccaaggagat gaccatgaag   1380
taccgcatgg agggctgcgt ggacggccac aagttcgtga tcaccggcga gggcatcggc   1440
taccccttca agggcaagca ggccatcaac ctgtgcgtgg tggagggcgg ccccttgccc   1500
ttcgccgagg acatcttgtc cgccgccttc atgtacggca accgcgtgtt caccgagtac   1560
ccccaggaca tcgtcgacta cttcaagaac tcctgccccg ccggctacac ctgggaccgc   1620
tccttcctgt tcgaggacgg cgccgtgtgc atctgcaacg ccgacatcac cgtgagcgtg   1680
gaggagaact gcatgtacca ccgagtccaag ttctacggcg tgaacttccc cgccgacggc   1740
cccgtgatga agaagatgac cgacaactgg gagccctcct gcgagaagat catccccgtg   1800
cccaagcagg gcatcttgaa gggcgacgtg agcatgtacc tgctgctgaa ggacggtggc   1860
cgcttgcgct gccagttcga caccgtgtac aaggccaagt ccgtgccccg caagatgccc   1920
gactggcact tcatccagca caagctgacc cgcgaggacc gcagcgacgc caagaaccag   1980
aagtggcacc tgaccgagca cgccatcgcc tccggctccg ccttgccctc cggactcaga   2040
tctcgactag agtcgaacct agacttgtcc atcttctgga ttggccaact taattaatgt   2100
atgaaataaa aggatgcaca catagtgaca tgctaatcac tataatgtgg gcatcaaagt   2160
tgtgtgttat gtgtaattac tagttatctg aataaaagag aaagagatca tccatatttc   2220
ttatcctaaa tgaatgtcac gtgtctttat aattctttga tgaaccagat gcatttcatt   2280
aaccaaatcc atatacatat aaatattaat catatataat taatatcaat tgggttagca   2340
aaacaaatct agtctaggtg tgttttgcga attctagtgg ccggcccagc tgatatccat   2400
cacactggcg gccgcactcg actgaattgg ttccggcgcc agcctgcttt tttgtacaaa   2460
gttggcatta taaaaaagca ttgcttatca atttgttgca acgaacaggt cactatcagt   2520
caaaataaaa tcattatttg gggcccgagc ttaagtaact aactaacagg aagagtttgt   2580
agaaacgcaa aaaggccatc cgtcaggatg gccttctgct tagtttgatg cctggcagtt   2640
tatggcgggc gtcctgcccg ccaccctccg ggccgttgct tcacaacgtt caaatccgct   2700
cccggcggat ttgtcctact caggagagcg ttcaccgaca acaacagat aaaacgaaag   2760 gcccagtctt ccgactgagc ctttcgtttt atttgatgcc tggcagttcc ctactctcgc   2820
ttagtagtta gacgtccccg agatccatgc tagcggtaat acggttatcc acagaatcag   2880
gggataacgc aggaaagaac atgtgagcaa aaggccagca aaaggccagg aaccgtaaaa   2940
aggccgcgtt gctggcgttt ttccataggc tccgcccccc tgacgagcat cacaaaaatc   3000
gacgctcaag tcagaggtgg cgaaacccga caggactata aagataccag gcgtttcccc   3060
ctggaagctc cctcgtgcgc tctcctgttc cgaccctgcc gcttaccgga tacctgtccg   3120
cctttctccc ttcgggaagc gtggcgcttt ctcatagctc acgctgtagg tatctcagtt   3180
cggtgtaggt cgttcgctcc aagctgggct gtgtgcacga accccccgtt cagcccgacc   3240
```

```
gctgcgcctt atccggtaac tatcgtcttg agtccaaccc ggtaagacac gacttatcgc   3300
cactggcagc agccactggt aacaggatta gcagagcgag gtatgtaggc ggtgctacag   3360
agttcttgaa gtggtggcct aactacggct acactagaag aacagtattt ggtatctgcg   3420
ctctgctgaa gccagttacc ttcggaaaaa gagttggtag ctcttgatcc ggcaaacaaa   3480
ccaccgctgg tagcggtggt ttttttgttt gcaagcagca gattacgcgc agaaaaaaag   3540
gatctcaaga agatcctttg atcttttcta cggggtctga cgctcagtgg aacgggccc    3600 aatctgaata atgttacaac caattaacca attctgatta gaaaaactca tcgagcatca   3660
aatgaaactg caatttattc atatcaggat tatcaatacc atattttga aaaagccgtt    3720 tctgtaatga aggagaaaac tcaccgaggc agttccatag gatggcaaga tcctggtatc   3780
ggtctgcgat tccgactcgt ccaacatcaa tacaacctat taatttcccc tcgtcaaaaa   3840
taaggttatc aagtgagaaa tcaccatgag tgacgactga atccggtgag aatggcaaaa   3900
gtttatgcat ttctttccag acttgttcaa caggccagcc attacgctcg tcatcaaaat   3960
cactcgcatc aaccaaaccg ttattcattc gtgattgcgc ctgagcgaga cgaaatacgc   4020
gatcgctgtt aaaaggacaa ttacaaacag gaatcgaatg caaccggcgc aggaacactg   4080
ccagcgcatc aacaatattt tcacctgaat caggatattc ttctaatacc tggaatgctg   4140 ttttccggg gatcgcagtg gtgagtaacc atgcatcatc aggagtacgg ataaaatgct    4200
tgatggtcgg aagaggcata aattccgtca gccagtttag tctgaccatc tcatctgtaa   4260
catcattggc aacgctacct ttgccatgtt cagaaacaa ctctggcgca tcgggcttcc    4320
catacaagcg atagattgtc gcacctgatt gcccgacatt atcgcgagcc catttatacc   4380
catataaatc agcatccatg ttggaattta atcgcggcct cgacgtttcc cgttgaatat   4440
ggctcataac acccccttgta ttactgttta tgtaagcaga cagtttatt gttcatgatg    4500 atatatttt atcttgtgca atgtaacatc agagattttg agacacgggc cagagctgca    4560
gctggatggc aaataatgat tttattttga ctgatagtga cctgttcgtt gcaacaaatt   4620
gataagcaat gctttcttat aatgccaact ttgtacaaga agctgggtc tagatatctc    4680 gac                                                                 4683

<210> SEQ ID NO 26
<211> LENGTH: 9282
<212> TYPE: DNA
<213> ORGANISM: Artificial sequence
<220> FEATURE:
<223> OTHER INFORMATION: Plasmid, QC641-1G

<400> SEQUENCE: 26
ccgggcgttt cctgtttagg aaagtcgatc cataaagttt tcactccatt atttaatcag     60
tttaatgccg tttaatattt ttgtactgat gtaaaataat tttatattat tatttttaaaa   120 gttaataaat ttgaataatt ttttactgta taattctttt tctcttatat aattagtcac    180
tgcactagaa tcagaaccta attcattttt ggaaacgatt accaaaataa ataaataacc    240
atgctgacga aaaatttaaa aatattgata gtactgcttg gttattggca aactaagttt    300
tgatatgtac tagcaggagc cgagatattt aatttatagc atttggatta attagttttg    360
tggtaagaaa taatcaatta tttatttatg atggacataa agaataaat agttgtttat    420 acttttcac aattttatca tatttttatt gagtagaatt aattattttg tattattcaa    480
acaccctatt agtattgaaa aaaatacttg aaagggacga attcgtcact gacttgtggc    540
```

```
tccttggtct taaagtgttg gtaatgcgat tttaaatatc aataataatt aaaatgtgaa      600
aagagaaaaa tatttatact agtatgttag gtaaaatctt atcaagctaa tttaagatat      660
acttttatct tatcttgcat atgcgatgta caaattaaag aacattcaat atatattaat      720
tagaaaaaag ttactgttaa aatttcaaag gtagcgagag gaataatatg gtatcacatg      780
gacaatagtt atggtgaaga gagtgataga ctgatggatg ggacaaagac aaaagcactt      840
ccaaaataag agagtagttc aattcaactt aattagtaag taatatgcat attaaggaag      900
cattgcaatt ttgcaaatta aaacaaaccc atcacaatta atatagcatg actcacctac      960
catcattatt tgtgaaactg atttatcatt ccttggctca ctctttccta attctaaagt     1020
actccctctc tatataaatt ctcactcacc ttagttttct tctcatttca ctcacttgct     1080
ttcaaattct cattttcaag gtgagagtgg actatgacta tactatatat ctttgttttt     1140 tgttttgaa atcaaacgc gaagagtct tctttatttt ctcttctgaa aaaaaaaaa     1200 tcagtgggaa attaaatcat gtgttgctat tagcattttc tcttcttat tttgttatta     1260 tatattgttt gtgatcatcc aattgatgca tttaaattta tgttggtgtt atttgtgtag     1320
ctgtttggtg taaccatggc ccagtccaag cacggcctga ccaaggagat gaccatgaag     1380
taccgcatgg agggctgcgt ggacggccac aagttcgtga tcaccggcga gggcatcggc     1440 tacccttca agggcaagca ggccatcaac ctgtgcgtgg tggagggcgg ccccttgccc     1500
ttcgccgagg acatcttgtc cgccgccttc atgtacggca accgcgtgtt caccgagtac     1560
ccccaggaca tcgtcgacta cttcaagaac tcctgccccg ccggctacac ctgggaccgc     1620
tccttcctgt tcgaggacgg cgccgtgtgc atctgcaacg ccgacatcac cgtgagcgtg     1680
gaggagaact gcatgtacca cgagtccaag ttctacggcg tgaacttccc cgccgacggc     1740
cccgtgatga gaagatgac cgacaactgg gagccctcct gcgagaagat catccccgtg     1800
cccaagcagg gcatcttgaa gggcgacgtg agcatgtacc tgctgctgaa ggacggtggc     1860
cgcttgcgct gccagttcga caccgtgtac aaggccaagt ccgtgccccg caagatgccc     1920
gactggcact tcatccagca caagctgacc cgcgaggacc gcagcgacgc caagaaccag     1980
aagtggcacc tgaccgagca cgccatcgcc tccggctccg ccttgccctc cggactcaga     2040
tctcgactag agtcgaacct agacttgtcc atcttctgga ttggccaact taattaatgt     2100
atgaaataaa aggatgcaca catagtgaca tgctaatcac tataatgtgg gcatcaaagt     2160
tgtgtgttat gtgtaattac tagttatctg aataaaagag aaagagatca tccatatttc     2220
ttatcctaaa tgaatgtcac gtgtctttat aattctttga tgaaccagat gcatttcatt     2280
aaccaaatcc atatacatat aaatattaat catatataat taatatcaat tgggttagca     2340
aaacaaatct agtctaggtg tgttttgcga attctagtgg ccggcccagc tgatatccat     2400
cacactggcg gccgcactcg actgaattgg ttccggcgcc agcctgcttt tttgtacaaa     2460
cttgtttgat aaacactagt aacggccgcc agtgtgctgg aattcgccct tcccaagctt     2520
tgctctagat caaactcaca tccaaacata acatggatat cttccttacc aatcatacta     2580
attattttgg gttaaatatt aatcattatt tttaagatat taattaagaa attaaaagat     2640
tttttaaaaa aatgtatata aattatattat tcatgatttt tcatacattt gattttgata     2700
ataaatatat tttttttaat ttcttaaaaa atgttgcaag acacttatta gacatagtct     2760
tgttctgttt acaaaagcat tcatcattta atacattaaa aatatttaa tactaacagt     2820 agaatcttct tgtgagtggt gtgggagtag gcaacctggc attgaaacga gagaaagaga     2880
gtcagaacca gaagacaaat aaaaagtatg caacaaacaa atcaaaatca aagggcaaag     2940
```

```
gctgggguttg gctcaattgg ttgctacatt caattttcaa ctcagtcaac ggttgagatt    3000
cactctgact tccccaatct aagccgcgga tgcaaacggt tgaatctaac ccacaatcca    3060
atctcgttac ttagggcttt ttccgtcatt aactcacccc tgccacccgg tttccctata    3120
aattggaact caatgctccc ctctaaactc gtatcgcttc agagttgaga ccaagacaca    3180
ctcgttcata tatctctctg ctcttctctt ctcttctacc tctcaaggta cttttcttct    3240
ccctctacca aatcctagat tccgtggttc aatttcggat cttgcacttc tggtttgctt    3300
tgccttgctt tttcctcaac tgggtccatc taggatccat gtgaaactct actctttctt    3360
taatatctgc ggaatacgcg tttgactttc agatctagtc gaaatcattt cataattgcc    3420
tttctttctt ttagcttatg agaaataaaa tcacttttt tttatttcaa ataaaacctt     3480
gggccttgtg ctgactgaga tggggtttgg tgattacaga attttagcga attttgtaat    3540
tgtacttgtt tgtctgtagt tttgttttgt tttcttgttt ctcatacatt ccttaggctt    3600
caattttatt cgagtatagg tcacaatagg aattcaaact ttgagcaggg gaattaatcc    3660
cttccttcaa atccagtttg tttgtatata tgtttaaaaa atgaaacttt tgctttaaat    3720
tctattataa ctttttttat ggctgaaatt tttgcatgtg tctttgctct ctgttgtaaa    3780
tttactgttt aggtactaac tctaggcttg ttgtgcagtt tttgaagtat aacaacagaa    3840
gttcctattc cgaagttcct attctctaga aagtatagga acttccacca cacaacacaa    3900
tggcggccac cgcttccaga accacccgat tctcttcttc ctcttcacac cccaccttcc    3960
ccaaacgcat tactagatcc accctccctc tctctcatca aaccctcacc aaacccaacc    4020
acgctctcaa aatcaaatgt tccatctcca aaccccccac ggcggcgccc ttcaccaagg    4080
aagcgccgac cacggagccc ttcgtgtcac ggttcgcctc cggcgaacct cgcaagggcg    4140
cggacatcct tgtggaggcg ctggagaggc agggcgtgac gacggtgttc gcgtaccccg    4200
gcggtgcgtc gatggagatc caccaggcgc tcacgcgctc cgccgccatc cgcaacgtgc    4260
tcccgcgcca cgagcagggc ggcgtcttcg ccgccgaagg ctacgcgcgt tcctccggcc    4320
tccccggcgt ctgcattgcc acctccggcc ccggcgccac caacctcgtg agcggcctcg    4380
ccgacgcttt aatggacagc gtcccagtcg tcgccatcac cggccaggtc gcccgccgga    4440
tgatcggcac cgacgccttc caagaaaccc cgatcgtgga ggtgagcaga tccatcacga    4500
agcacaacta cctcatcctc gacgtcgacg acatcccccg cgtcgtcgcc gaggctttct    4560
tcgtcgccac ctccggccgc cccggtccgg tcctcatcga cattcccaaa gacgttcagc    4620
agcaactcgc cgtgcctaat tgggacgagc ccgttaacct ccccggttac ctcgccaggc    4680
tgcccaggcc ccccgccgag gcccaattgg aacacattgt cagactcatc atggaggccc    4740
aaaagcccgt tctctacgtc ggcggtgca gtttgaattc cagtgctgaa ttgaggcgct     4800
ttgttgaact cactggtatt cccgttgcta gcactttaat gggtcttgga actttcccta    4860
ttggtgatga atattccctt cagatgctgg gtatgcatgg tactgtttat gctaactatg    4920
ctgttgacaa tagtgatttg ttgcttgcct ttggggtaag gtttgatgac cgtgttactg    4980
ggaagcttga ggcttttgct agtagggcta agattgttca cattgatatt gattctgccg    5040
agattgggaa gaacaagcag gcgcacgtgt cggtttgcgc ggatttgaag ttggccttga    5100
agggaattaa tatgattttg gaggagaaag gagtggaggg taagtttgat cttggaggtt    5160
ggagagaaga gattaatgtg cagaaacaca gtttccatt gggttacaag acattccagg     5220
acgcgatttc tccgcagcat gctatcgagg ttcttgatga gttgactaat ggagatgcta    5280
```

```
ttgttagtac tggggttggg cagcatcaaa tgtgggctgc gcagttttac aagtacaaga    5340
gaccgaggca gtggttgacc tcaggggtc ttggagccat gggttttgga ttgcctgcgg     5400
ctattggtgc tgctgttgct aaccctgggg ctgttgtggt tgacattgat ggggatggta    5460
gtttcatcat gaatgttcag gagttggcca ctataagagt ggagaatctc ccagttaaga    5520
tattgttgtt gaacaatcag catttgggta tggtggttca gttggaggat aggttctaca    5580
agtccaatag agctcacacc tatcttggag atccgtctag cgagagcgag atattcccaa    5640
acatgctcaa gtttgctgat gcttgtggga taccggcagc gcgagtgacg aagaaggaag    5700
agcttagagc ggcaattcag agaatgttgg acacccctgg cccctacctt cttgatgtca    5760
ttgtgcccca tcaggagcat gtgttgccga tgattcccag taatggatcc ttcaaggatg    5820
tgataactga gggtgatggt agaacgaggt actgattgcc tagaccaaat gttccttgat    5880
gcttgttttg tacaatatat ataagataat gctgtcctag ttgcaggatt tggcctgtgg    5940
tgagcatcat agtctgtagt agttttggta gcaagacatt ttattttcct tttatttaac    6000
ttactacatg cagtagcatc tatctatctc tgtagtctga tatctcctgt tgtctgtatt    6060
gtgccgttgg attttttgct gtagtgagac tgaaaatgat gtgctagtaa taatatttct    6120
gttagaaatc taagtagaga atctgttgaa gaagtcaaaa gctaatggaa tcaggttaca    6180
tattcaatgt ttttcttttt ttagcggttg gtagacgtgt agattcaact tctcttggag    6240
ctcacctagg caatcagtaa aatgcatatt cctttttaa cttgccattt atttactttt     6300
agtggaaatt gtgaccaatt tgttcatgta gaacggattt ggaccattgc gtccacaaaa    6360
cgtctctttt gctcgatctt cacaaagcga taccgaaatc cagagatagt tttcaaaagt    6420
cagaaatggc aaagttataa atagtaaaac agaatagatg ctgtaatcga cttcaataac    6480
aagtggcatc acgtttctag ttctagaccc atcagctggg ccggcccagc tgatgatccc    6540
ggtgaagttc ctattccgaa gttcctattc tccagaaagt ataggaactt cactagagct    6600
tgcggccgcg catgctgact taatcagcta acgccactcg agggggggcc cggtaccggc    6660
gcgccgttct atagtgtcac ctaaatcgta tgtgtatgat acataaggtt atgtattaat    6720
tgtagccgcg ttctaacgac aatatgtcca tatggtgcac tctcagtaca atctgctctg    6780
atgccgcata gttaagccag ccccgacacc cgccaacacc cgctgacgcg ccctgacggg    6840
cttgtctgct cccggcatcc gcttacagac aagctgtgac cgtctccggg agctgcatgt    6900
gtcagaggtt ttcaccgtca tcaccgaaac gcgcgagacg aaagggcctc gtgatacgcc    6960 tattttata ggttaatgtc atgaccaaaa tcccttaacg tgagttttcg ttccactgag     7020
cgtcagaccc cgtagaaaag atcaaaggat cttcttgaga tccttttttt ctgcgcgtaa    7080
tctgctgctt gcaaacaaaa aaaccaccgc taccagcggt ggtttgtttg ccggatcaag    7140
agctaccaac tcttttccg aaggtaactg gcttcagcag agcgcagata ccaaatactg     7200
tccttctagt gtagccgtag ttaggccacc acttcaagaa ctctgtagca ccgcctacat    7260
acctcgctct gctaatcctg ttaccagtgg ctgctgccag tggcgataag tcgtgtctta    7320
ccgggttgga ctcaagacga tagttaccgg ataaggcgca gcggtcgggc tgaacggggg    7380
gttcgtgcac acagcccagc ttggagcgaa cgacctacac cgaactgaga tacctacagc    7440
gtgagcattg agaaagcgcc acgcttcccg aagggagaaa ggcggacagg tatccggtaa    7500
gcggcagggt cggaacagga gagcgcacga gggagcttcc agggggaaac gcctggtatc    7560
tttatagtcc tgtcgggttt cgccacctct gacttgagcg tcgattttg tgatgctcgt     7620 caggggggcg gagcctatgg aaaaacgcca gcaacgcggc ctttttacgg ttcctggcct    7680
```

-continued

```
tttgctggcc ttttgctcac atgttctttc ctgcgttatc ccctgattct gtggataacc    7740
gtattaccgc ctttgagtga gctgataccg ctcgccgcag ccgaacgacc gagcgcagcg    7800
agtcagtgag cgaggaagcg gaagagcgcc caatacgcaa accgcctctc cccgcgcgtt    7860
ggccgattca ttaatgcagg ttgatcagat ctcgatcccg cgaaattaat acgactcact    7920
atagggagac cacaacggtt tccctctaga ataattttg tttaacttta agaaggagat    7980
atacccatgg aaaagcctga actcaccgcg acgtctgtcg agaagtttct gatcgaaaag    8040
ttcgacagcg tctccgacct gatgcagctc tcggagggcg aagaatctcg tgctttcagc    8100
ttcgatgtag gagggcgtgg atatgtcctg cgggtaaata gctgcgccga tggtttctac    8160
aaagatcgtt atgtttatcg gcactttgca tcggccgcgc tcccgattcc ggaagtgctt    8220
gacattgggg aattcagcga gagcctgacc tattgcatct cccgccgtgc acagggtgtc    8280
acgttgcaag acctgcctga aaccgaactg cccgctgttc tgcagccggt cgcggaggct    8340
atggatgcga tcgctgcggc cgatcttagc cagacgagcg gttcggccc attcggaccg    8400 caaggaatcg gtcaatacac tacatggcgt gatttcatat gcgcgattgc tgatccccat    8460
gtgtatcact ggcaaaactgt gatggacgac accgtcagtg cgtccgtcgc gcaggctctc    8520
gatgagctga tgctttgggc cgaggactgc cccgaagtcc ggcacctcgt gcacgcggat    8580
ttcggctcca acaatgtcct gacggacaat ggccgcataa cagcggtcat tgactggagc    8640
gaggcgatgt tcggggattc ccaatacgag gtcgccaaca tcttcttctg gaggccgtgg    8700
ttggcttgta tggagcagca gacgcgctac ttcgagcgga ggcatccgga gcttgcagga    8760
tcgccgcggc tccgggcgta tatgctccgc attggtcttg accaactcta tcagagcttg    8820
gttgacggca atttcgatga tgcagcttgg gcgcagggtc gatgcgacgc aatcgtccga    8880
tccggagccg ggactgtcgg gcgtacacaa atcgcccgca gaagcgcggc cgtctggacc    8940
gatggctgtg tagaagtact cgccgatagt ggaaaccgac gccccagcac tcgtccgagg    9000
gcaaaggaat agtgaggtac agcttggatc gatccggctg ctaacaaagc ccgaaaggaa    9060
gctgagttgg ctgctgccac cgctgagcaa taactagcat aacccctgg ggcctctaaa    9120 cgggtcttga ggggttttt gctgaaagga ggaactatat ccggatgctc gggcgcgccg    9180
gtacccgggt accgagctca ctagacgcgg tgaaattacc taattaacac cggtgtttat    9240
cgaaccactt tgtacaagaa agctgggtct agatatctcg ac                      9282
```

<210> SEQ ID NO 27
<211> LENGTH: 22
<212> TYPE: DNA
<213> ORGANISM: Artificial sequence
<220> FEATURE:
<223> OTHER INFORMATION: SAMS forward primer SAMS-76F

<400> SEQUENCE: 27

```
aggcttgttg tgcagttttt ga                                              22
```

<210> SEQ ID NO 28
<211> LENGTH: 22
<212> TYPE: DNA
<213> ORGANISM: Artificial sequence
<220> FEATURE:
<223> OTHER INFORMATION: FAM labeled ALS probe ALS-100T

<400> SEQUENCE: 28

```
ccacacaaca caatggcggc ca                                              22
```

<210> SEQ ID NO 29
<211> LENGTH: 22
<212> TYPE: DNA
<213> ORGANISM: Artificial sequence
<220> FEATURE:
<223> OTHER INFORMATION: ALS reverse primer ALS-163R

<400> SEQUENCE: 29
ggaagaagag aatcgggtgg tt                                              22

<210> SEQ ID NO 30
<211> LENGTH: 24
<212> TYPE: DNA
<213> ORGANISM: Artificial sequence
<220> FEATURE:
<223> OTHER INFORMATION: GFP forward primer GFP-24F

<400> SEQUENCE: 30
gaccaaggag atgaccatga agta                                            24

<210> SEQ ID NO 31
<211> LENGTH: 14
<212> TYPE: DNA
<213> ORGANISM: Artificial sequence
<220> FEATURE:
<223> OTHER INFORMATION: FAM labeled GFP probe GFP-51T

<400> SEQUENCE: 31
catggagggc tgcg                                                       14

<210> SEQ ID NO 32
<211> LENGTH: 20
<212> TYPE: DNA
<213> ORGANISM: Artificial sequence
<220> FEATURE:
<223> OTHER INFORMATION: GFP reverse primer GFP-92R

<400> SEQUENCE: 32
ccggtgatca cgaacttgtg                                                 20

<210> SEQ ID NO 33
<211> LENGTH: 24
<212> TYPE: DNA
<213> ORGANISM: Artificial sequence
<220> FEATURE:
<223> OTHER INFORMATION: HSP forward primer HSP-F1

<400> SEQUENCE: 33
caaacttgac aaagccacaa ctct                                            24

<210> SEQ ID NO 34
<211> LENGTH: 20
<212> TYPE: DNA
<213> ORGANISM: Artificial sequence
<220> FEATURE:
<223> OTHER INFORMATION: VIC labeled HSP probe HSP probe

<400> SEQUENCE: 34
ctctcatctc atataaatac                                                 20

<210> SEQ ID NO 35
<211> LENGTH: 21
<212> TYPE: DNA
<213> ORGANISM: Artificial sequence
<220> FEATURE:
<223> OTHER INFORMATION: HSP reverse primer HSP-R1

<400> SEQUENCE: 35
ggagaaattg gtgtcgtgga a                                            21

<210> SEQ ID NO 36
<211> LENGTH: 100
<212> TYPE: DNA
<213> ORGANISM: Artificial sequence
<220> FEATURE:
<223> OTHER INFORMATION: ATTL1

<400> SEQUENCE: 36
caaataatga ttttattttg actgatagtg acctgttcgt tgcaacaaat tgataagcaa    60 tgcttttta taatgccaac tttgtacaaa aaagcaggct                          100

<210> SEQ ID NO 37
<211> LENGTH: 100
<212> TYPE: DNA
<213> ORGANISM: Artificial sequence
<220> FEATURE:
<223> OTHER INFORMATION: ATTL2

<400> SEQUENCE: 37
caaataatga ttttattttg actgatagtg acctgttcgt tgcaacaaat tgataagcaa    60
tgctttctta taatgccaac tttgtacaag aaagctgggt                         100

<210> SEQ ID NO 38
<211> LENGTH: 125
<212> TYPE: DNA
<213> ORGANISM: Artificial sequence
<220> FEATURE:
<223> OTHER INFORMATION: ATTR1

<400> SEQUENCE: 38
acaagtttgt acaaaaaagc tgaacgagaa acgtaaaatg atataaatat caatatatta    60
aattagattt tgcataaaaa acagactaca taatactgta aaacacaaca tatccagtca   120
ctatg                                                              125

<210> SEQ ID NO 39
<211> LENGTH: 125
<212> TYPE: DNA
<213> ORGANISM: Artificial sequence
<220> FEATURE:
<223> OTHER INFORMATION: ATTR2

<400> SEQUENCE: 39
accactttgt acaagaaagc tgaacgagaa acgtaaaatg atataaatat caatatatta    60
aattagattt tgcataaaaa acagactaca taatactgta aaacacaaca tatccagtca   120
ctatg                                                              125

<210> SEQ ID NO 40
<211> LENGTH: 21
<212> TYPE: DNA
<213> ORGANISM: Artificial sequence
<220> FEATURE:
<223> OTHER INFORMATION: ATTB1

<400> SEQUENCE: 40
caagtttgta caaaaaagca g                                             21

<210> SEQ ID NO 41

-continued

```
<211> LENGTH: 21
<212> TYPE: DNA
<213> ORGANISM: Artificial sequence
<220> FEATURE:
<223> OTHER INFORMATION: ATTB2

<400> SEQUENCE: 41
ccactttgta caagaaagct g                                              21

<210> SEQ ID NO 42
<211> LENGTH: 1267
<212> TYPE: DNA
<213> ORGANISM: Glycine max

<400> SEQUENCE: 42
gtgaaactga tttatcattc cttggctcac tctttcctaa ttctaaagta ctccctctct    60
atataaattc tcactcacct tagttttctt ctcatttcac tcacttgctt tcaaattctc   120
attttcaagc tgtttggtgt aaagatggga caagtgcttg gttgtgttca agtgaagcag   180
tcaactgtag ccgtcaagga atgtttcggg aagtacgatg atgttcttca acctggttgc   240
cattttgtgc catggtgtct tggctgcggt gtggctggtg tcctttctac gcgtgtcatg   300
cagctaagtc ttcgttgtga aactaagaca aaggacaatg tgtttgttaa tgtggttgcc   360
tcaatccaat atcgagcatt ggcagaaaag gcatcagatg cttactacaa actcaccaat   420
accaaagcac agatacaatc ctatgtcttt gatgttatca gagctactgt tccaaagatg   480
gaacttgatg ctgttttttga gcagaagaac acaattgcaa aagcagtgga cgaagaactt   540
gggaaggcta tgtcagcata tgggtacgag atagttcaga ctcttattgt ggatattgtg   600
ccggatgagc atgtgaagaa agccatgaat gagattaatg ctgctgcaag attgagggtg   660
gctacaaacg acaaagctga agcagagaaa ataatgcaga taaagcgagc agaagggggat   720 gcagaatcaa agtacctagc aggccttgga gtttctcgtc agcgccaagc catagttgat   780
gggctaagag acagtgttct agcatttttct ggtaatgtgc ctggaacatc atcaaaggat   840
atcatggaca tggttctcat gactcaatat tttgacacaa tgaaggagat tggtgcatcc   900
tccaaatcca atgctgtttt cattccacat ggacctggtg ctgtgagtga tgttgcttca   960
caagtaagga atggtcttct ccaaggaaat gcaacaacag agtcttgaag acatacacat  1020
atatcatcat accatgattt cctcctccag gcacttgtag tttagctttg caactaaatc  1080
tttatatatg ctactattat gaatcatcca tggcaagttg gcaactaatg ccttctatat  1140
gtatatggtc ttcctaatca accatggcaa cttttcttaat tttatccact attatgaatc  1200
ttcaactttt atgatatctc attaaatata atataattac atacccacgc gtatgcatga  1260
tttcaat                                                            1267

<210> SEQ ID NO 43
<211> LENGTH: 267
<212> TYPE: DNA
<213> ORGANISM: Glycine max

<400> SEQUENCE: 43
cactcacttg ctttcaaatt ctcattttca aggtgagagt ggactatgac tatactatat    60
atctttgttt tttgttttttg aaaatcaaac gccgaagagt cttctttatt ttctcttctg   120
aaaaaaaaaa aatcagtggg aaattaaatc atgtgttgct attagcattt tctcttcttt   180
```

```
attttgttat tatatattgt ttgtgatcat ccaattgatg catttaaatt tatgttggtg        240
ttatttgtgt agctgtttgg tgtaacc                                            267

<210> SEQ ID NO 44
<211> LENGTH: 47
<212> TYPE: DNA
<213> ORGANISM: Glycine max

<400> SEQUENCE: 44
cactcacttg ctttcaaatt ctcattttca agctgtttgg tgtaaag                       47

<210> SEQ ID NO 45
<211> LENGTH: 1559
<212> TYPE: DNA
<213> ORGANISM: Glycine max

<400> SEQUENCE: 45
atacgcattg tttccatgaa tccttcaagt cgacgatttt tttattttt atttttatt         60 ttttattttt ggtataattc gacgaaactt gggttcatta tttgagtcca atgttcagtt        120
tacgcgctta aattagtact attctatctt aattactttt tcttatttct aacattgttg        180
aattagcttt cccaatcttc taaaaaaagc gtttccgtgt tatcagttga tgctgcaaaa        240
ggaaaccaga cgtttcctgt ttaggaaagt cgatccataa agttttcact ccattattta        300
atcagtttaa tgccgtttaa tattttttgta ctgatgtaaa ataattttat attattattt       360
taaaagttaa taaatttgaa taattttttta ctgtataatt cttttctct tgtataatta        420 gtcactgcac tagaatcaga acctaattca cttttggaaa cgattaccaa aataaataaa        480
taaccatgct gacgaaaaat ttaaaaatat tgatagtact gcttggttat tggcaaacta        540
agttttgata tgtactagca ggagccgaga tatttaattt atagcatttg gattaattag        600
ttttgtggta agaaataatc aattatttat ttatgatgga cataaaagaa taaatagttg        660
tttatacttt ttcacaattt tatcatattt ttattgagta gaattaatta ttttgtatta        720
ttcaaacacc ctattagtat tgaaaaaaat acttgaaagg gacgaattcg tcactgactt        780
gtggctcctt ggtcttaaag tgttggtaat gcgattttaa atatcaataa taattaaaat        840
gtgaaaagag aaaaatattt atactagtat gttaggtaaa atcttatcaa gctaatttaa        900
gatatacttt tatcttgcat atgcgatgta caaattaaag aacattcaat atatattaat        960
tagaaaaaag ttactgttaa aatttcaaag gtagcgagag gaataatatg gtatcacatg       1020
gacaatagtt atggtgaaga gagtgataga ctgatggatg ggacaaagac aaaagcactt       1080
ccaaaataag agagtagttc aattcaactt aattagtaag taatatgcat attaaggaag       1140
cattgcaatt ttgcaaatta aaacaaaccc atcacaatta atatagcatg actcacctac       1200
catcattatt tgtgaaactg atttatcatt ccttggctca ctctttccta attctaaagt       1260
actccctctc tatataaatt ctcactcacc ttagttttct tctcatttca ctcacttgct       1320
ttcaaattct cattttcaag gtgagagtgg actatgacta tactatatat ctttgttttt       1380 tgttttgaa atcaaacgc cgaagagtct tctttatttt ctcttctgaa attaaatcat        1440
gtgttgctat tagcatttc tcttcttttat tttgttatta tatattgttt gtgatcatcc       1500
aattgatgca tttaaattta tgttggtgtt atttgtgtag ctgtttggtg taaagatgg        1559
```